US011697817B2

(12) United States Patent
Yukawa et al.

(10) Patent No.: US 11,697,817 B2
(45) Date of Patent: Jul. 11, 2023

(54) **GENUS *HYDROGENOPHILUS* BACTERIUM TRANSFORMANT**

(71) Applicants: Utilization of Carbon Dioxide Institute Co., Ltd., Tokyo (JP); The University of Tokyo, Tokyo (JP)

(72) Inventors: Hideaki Yukawa, Tokyo (JP); Naoto Ohtani, Tokyo (JP); Masaharu Ishii, Tokyo (JP)

(73) Assignees: UTILIZATION OF CARBON DIOXIDE INSTITUTE CO., LTD., Tokyo (JP); THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 17/047,757

(22) PCT Filed: Jun. 25, 2018

(86) PCT No.: PCT/JP2018/024073
§ 371 (c)(1),
(2) Date: Oct. 15, 2020

(87) PCT Pub. No.: WO2019/207812
PCT Pub. Date: Oct. 31, 2019

(65) Prior Publication Data
US 2021/0108215 A1 Apr. 15, 2021

(30) Foreign Application Priority Data
Apr. 27, 2018 (JP) ................. 2018-086100

(51) Int. Cl.
*C12P 7/16* (2006.01)
*C12N 7/04* (2006.01)
*C12N 15/74* (2006.01)
*C12P 7/06* (2006.01)

(52) U.S. Cl.
CPC ............ *C12N 15/74* (2013.01); *C12P 7/06* (2013.01); *C12P 7/16* (2013.01); *C12Y 101/01001* (2013.01); *C12Y 401/01001* (2013.01)

(58) Field of Classification Search
CPC .................. C12N 15/74; C12P 7/16
See application file for complete search history.

(56) References Cited

U.S. PATENT DOCUMENTS

| 5,559,016 | A | 9/1996 | Katsumata et al. | |
| 2004/0072312 | A1 | 4/2004 | Yukawa | |
| 2011/0097775 | A1* | 4/2011 | Green | C12P 7/52 435/160 |
| 2011/0287499 | A1 | 11/2011 | Brown et al. | |
| 2012/0115196 | A1 | 5/2012 | Yukawa et al. | |
| 2014/0273128 | A1 | 9/2014 | Coleman et al. | |

FOREIGN PATENT DOCUMENTS

| JP | H06-277082 A | 10/1994 |
| WO | 01/96573 A1 | 12/2001 |
| WO | 2009/122192 A1 | 10/2009 |
| WO | 2010/113832 A1 | 10/2010 |

OTHER PUBLICATIONS

Chen et al., J Ind Microbiol Biotechnol, 42, 1473-1479, 2015.*
Atsumi et al., "Non-fermentative pathways for synthesis of branched-chain higher alcohols as biofuels," Nature, 451: 86-89 (2008).
Atsumi et al., "Engineering the isobutanol biosynthetic pathway in *Escherichia coli* by comparison of three aldehyde reductase/alcohol dehydrogenase genes," Applied and Environmental Microbiology, 85: 651-657 (2010).
Li et al., "Engineering Bacillus subtilis for isobutanol production by heterologous Ehrlich pathway construction and the biosynthetic 2-ketoisovalerate precursor pathway overexpression," Applied and Environmental Microbiology, 91: 577-589(2011).
Jeon et al., "Isobutanol production from an engineered Shewanella oneidensis MR-1," Bioprocess Biosyst. Eng., 38: 2147-2154(2015).
Atsumi et al., "Direct photsynthetic recycling of carbon dioxide to isobutyraldehyde," Nature Biotechnology, 27 (12): 1177-1180(2009).
Lu et al., "Studies on the production of branched-chain alcohols in engineered Ralstonia eutropha," Applied Microbiology and Biotechnology, 96: 283-297 (2012).
Lin et al., "Isobutanol production at elevated temperatures in thermophilic Geobacillus thermoglucosidasius," Metabolic Engineering, 24:1-8 (2014).
Liu et al., "Coexpression of pyruvate decarboxylase and alcohol dehydrogenase genes in Lactobacillus brevis," FEMS Microbiol. Lett. 274: 291-297 (2007).
Talarico et al., "Construction and expression of an ethanol production operon in Gram-positive bacteria," Microbiology, 151: 4023-4031 (2005).
Deng et al., "Ethanol Synthesis by Genetic Engineering in Cyanobacteria," Applied and Environmental Microbiology, 65 (2): 523-528 (1999).
Luan et al., "Combinatory strategy for characterizing and understanding the ethanol synthesis pathway in cyanobacteria cell factories," Biotechnology for Biofuels, 8: 184 (2015).

(Continued)

*Primary Examiner* — Maryam Monshipouri
(74) *Attorney, Agent, or Firm* — Morgan, Lewis & Bockius LLP

(57) ABSTRACT

A transformant obtained by introducing a DNA of (a1), (a2), or (a3) below, and (b) an alcohol dehydrogenase gene, into a bacterium of the genus *Hydrogenophilus*, can efficiently produce isobutanol utilizing carbon dioxide as a sole carbon source.
(a1) DNA which consists of a base sequence of SEQ ID NO: 1;
(a2) DNA which consists of a base sequence having 90% or more identity with SEQ ID NO: 1, the DNA encoding a polypeptide having 2-keto-acid decarboxylase activity;
(a3) DNA which hybridizes with a DNA consisting of a base sequence complementary to SEQ ID NO: 1 under stringent conditions, and which encodes a polypeptide having 2-keto-acid decarboxylase activity.

19 Claims, No Drawings

Specification includes a Sequence Listing.

(56) References Cited

OTHER PUBLICATIONS

Keller et al., "Ethanol production by the hyperthermophilic archaeon Pyrococcus furiosus by expression of bacterial bifunctional alcohol dehydrogenases," Microbial Biotechnology, 10: 1535-1545 (2017).
Chung et al., "Cellulosic ethanol production via consolidated bioprocessing at 75 degrees Celsius by engineered Caldicellulosiruptor bescii," Biotechnology for Biofuels, 8: 163 (2015).
Wada et al., "Alanine production in an H+-ATPase-and lactate dehydrogenase-defective mutant of Escherichia coli expressing alanine dehydrogenase," Applied Microbiology and Biotechnology, 76: 819-825 (2007).
Lee et al., "Aerobic production of alanine by Escherichia coli aceF IdhA mutants expressing the Bacillus sphaericus alaD gene," Applied Microbiology and Biotechnology, 65: 56-60 (2004).
Uhlenbusch et al., "Expression of an L-Alanine Dehydrogenase Gene in Zymomonas mobilis and Excretion of L-Alanine," Applied and Environmental Microbiology, 57 (5): 1360-1366 (1991).
Hols et al., "Conversion of Lactococcus lactis from homolactic to homoalanine fermentation through metabolic engineering," Nature Biotechnology, 17: 588-592 (1999).
Jojima et al., "Engineering of sugar metabolism of Corynebacterium glutamicum for pdocution of amino acid L-alanine under oxygen deprivation," Applied Microbiology Biotechnology, 87: 159-165 (2010).
Journal of Mitsubishi Research Institute No. 34 1999 (see partial English translation).
Holland-Staley et al., "Aerobic Activity of Escherichia coli Alcohol Dehydrogenase Is Determined by a Single Amino Acid," Journal of Bacteriology, 182 (21): 6049-6054 (2000).
Goto et al., "Isolation and Culture Conditions of Thermophilic Hydrogen Bacteria," Agricultural and Biological Chemistry, 41 (4): 685-690 (1977).
Database GenBank, [online], Accession No. WP_013146672, Multispecies: alanine dehydrogenase [Geobacillus] (2019) (https://www.ncbi.nlm.nih.gov/protein/WP_013146672.1).
International Search Report issued in corresponding International Patent Application No. PCT/JP2018/024073 dated Sep. 11, 2018.
Majidian et al., "Metabolic engineering of microorganisms for biofuel production," Renewable and Sustainable Energy Reviews, 82: 3863-3885 (2018).

* cited by examiner

SEQUENCE LISTING

```
<160> NUMBER OF SEQ ID NOS: 111

<210> SEQ ID NO 1
<211> LENGTH: 1647
<212> TYPE: DNA
<213> ORGANISM: Artificial sequence
<220> FEATURE:
<223> OTHER INFORMATION: DNA coding a 2-keto-acid decarboxylase of
      Lactococcus lactis

<400> SEQUENCE: 1
atgtataccg tcggcgacta cctgctggat cgcctgcacg agctgggcat cgaggagatc      60
ttcggcgtcc cgggcgatta caatctgcag ttcctggatc agatcatctc gcgcaaggac     120
atgaaatggg tgggcaatgc gaacgaactg aacgcctcgt acatggcgga tggctacgcg     180
```

```
cggaccaaga aggccgccgc cttcctgacc accttcggcg tcggcgaact gtcggcggtc    240
aatggcctgg cgggctccta cgcggaaaat ctgcccgtcg tcgagatcgt gggctccccg    300
acgtcgaagg tgcagaacga aggcaagttc gtgcaccaca cgctggccga cggcgacttc    360
aagcacttca tgaaaatgca tgagcccgtc accgccgcgc ggacgctgct gacggccgag    420
aacgccacgg tggaaatcga ccgggtcctg tcggcgctgc tgaaagagcg caagccggtc    480
tatatcaatc tgccggtgga cgtggccgcc gcgaaagcgg aaaagccctc cctgccgctg    540
aaaaaggaga attcgacctc gaatacgagc gaccaggaga tcctgaacaa gatccaggaa    600
agcctgaaaa acgcgaagaa gccgatcgtc atcaccggcc acgaaatcat ctcgttcggc    660
ctggagaaga ccgtctcgca gttcatctcc aagaccaagc tgccgatcac gacgctgaac    720
ttcggcaagt cgtccgtcga cgaagccctg cccagcttcc tgggcatcta acggcaaa     780 ctgtccgagc ccaacctgaa agagttcgtc gagtcggcgg atttcatcct gatgctgggc    840
gtcaagctga ccgatagctc gaccggcgcg ttcacccatc acctgaacga gaacaagatg    900
atctcgctga atatcgacga aggcaaaatc ttcaacgagt cgatccagaa cttcgatttc    960
gaaagcctga tctcctcgct gctggacctg agcgagatcg aatacaaggg caagtatatc   1020
gacaaaaagc aagaagactt cgtcccgagc aacgccctgc tgagccagga ccggctgtgg   1080
caggccgtcg aaaacctgac ccagtcgaat gaaaccatcg tcgcggagca gggcacctcg   1140
ttcttcggcg ccagctcgat cttcctgaag ccgaagtccc acttcatcgg ccagccgctg   1200
tggggctcca tcggctatac cttcccggcg gccctgggca gccagatcgc cgacaaggaa   1260
agccgccatc tgctgttcat cggcgacggc tcgctgcagc tgacggtgca ggaactgggc   1320
ctggccatcc gcgagaagat caaccccatc tgcttcatca tcaataacga cggctacacc   1380
gtggagcggg aaatccacgg ccccaaccag agctacaacg acatcccgat gtggaattac   1440
tcgaaactgc ccgagtcgtt cggcgcgacc gaggaacggg tggtgtccaa gatcgtccgc   1500
accgagaatg agttcgtcag cgtgatgaag gaagcccagg cggaccccga accgcatgtat   1560 tggatcgaac tgatcctggc gaaggaagac gcccccaagg tcctgaagaa gatgggcaag   1620
ctgttcgcgg agcagaacaa gagctaa                                       1647
```

<210> SEQ ID NO 2  
<211> LENGTH: 1011  
<212> TYPE: DNA  
<213> ORGANISM: Klebsiella pneumoniae

<400> SEQUENCE: 2

```
atgaaggcag ctgttgttac ccacgaccat caggttaacg tcacggaaaa aacgctgcgc     60
ccgctggaat acggcgaagc gctgttgaaa atggaatgct gcggcgtgtg tcatactgac    120
ctgcacgtga aaacggcga ttttggcgat aaaaccggcg tcattctcgg ccatgaaggg    180
atcggggtgg tacaaaaagt cggcccgggc gtcacctccc tgaagccggg cgaccgcgcc    240
agcgtggcgt ggttcttcga aggctgcggc cactgcgatt actgtaacag cggcaacgag    300
acgctctgcc gctcggtgaa aaacgccggc tataccgtcg atggcggcat ggcggaagag    360
tgcatcgtca ccgccaacta cgcggtaaaa gttccggacg gctcgactc cgccgccgcc    420 agcagcatca cctgcgcggg cgtcaccacc tacaaagcgg tcaaggtctc ccacatcaaa    480
ccgggccagt ggatcgccat ctacggcctg ggcgggttgg gtaacctcgc gctgcagtat    540
gcgaagaatg tctttaacgc caagtgatc gctatcgacg tcaacgacgg acagctggag    600
ctggcggcct cgatgggcgc cgacctgacc atcaactccc gcaatgaaga tgcggcgaaa    660
```

| | |
|---|---|
| gtgattcagg aaaaaaccgg cggcgcccac gctgcggtag taaccgcggt ggccaaagcg | 720 |
| gcctttaact cggcggtgga tgccgttcgc gccggtggcc gcgtggtcgc ggtgggcctg | 780 |
| ccgccggagg cgatgagcct cgatattccg cgtctggtgc tggacggcat cgaggtggtc | 840 |
| ggttcgctgg tcggcacccg tcaggatctg gtggaagcct tccagtttgc cgccgaaggc | 900 |
| aaagtagtgc cgaaagtcac cctgcgtccg ctggaagata tcaacgctat cttcaaagag | 960 |
| atggagcaag tcagatccg cggccgtatg gttatcgatc tgcgtagcta a | 1011 |

<210> SEQ ID NO 3
<211> LENGTH: 1011
<212> TYPE: DNA
<213> ORGANISM: Geobacillus thermocatenulatus

<400> SEQUENCE: 3

| | |
|---|---|
| atgaaagccg ccgttgttca caaattcaaa caaaaacttc aaattgaaga agtggagaaa | 60 |
| ccaaaactag ggtatggcga agtgcttgtg aaaattgaag cttgtggcgt ctgccatacc | 120 |
| gatttgcatg cggcccatgg agattggcca gtaaaaccga acttccgct tattcctggt | 180 |
| catgaaggag taggaatcgt tgttgaggtc ggcgagggga tgaaatcaat caaaattggc | 240 |
| gatcgtgttg gcattccatg gttatactcg gcatgcggtg aatgtgaata ttgtttaagc | 300 |
| ggtcaagaaa cactttgtcc acatcaatta aatggtggat actctgtcga tggcagttat | 360 |
| gcagaatatt gcaaagcccc ggccgattat gtcgcacgaa ttcctaaaaa tctcgatcct | 420 |
| gtacaagttg ctcctattct tgtgctggga gtcacaacgt ataaagcatt aaaagtttca | 480 |
| aatgccaagc ctggtgaatg ggtcgctatt tatggaatcg ggggattggg ccatattgct | 540 |
| cttcaatatg ccaaagcaat gggattaaat gtcgttgctg ttgatatcag tgatgaaaag | 600 |
| gcagagcttg cagcaaagtt aggagctgat attacaatca atggcctgcg tgaagacccc | 660 |
| gtagcaacaa ttcgtgaaaa agtaggcgga gtgcatgcag ctattagcgt tgctgtaacg | 720 |
| aaaaaagctt tcgaacaagc ctatcaatcc gttcgacgcg gtggttgcct tgtcatcgtt | 780 |
| ggactgcctc acgatgaact accgatccct atttttgaca ctgtattaaa tggcgttaca | 840 |
| ataaaaggtt cgatcgtcgg tacacgaaaa gatatgcaag aagctttaga tttcgccgca | 900 |
| cgcggaaaag ttcgccccat tgtggaagcg gtaccattag aaaaaattaa cgaagtattt | 960 |
| gaacggatgg aaaaaggcca aatcaatggc cgcattgttt aacaatgta a | 1011 |

<210> SEQ ID NO 4
<211> LENGTH: 1023
<212> TYPE: DNA
<213> ORGANISM: Geobacillus thermoglucosidasius

<400> SEQUENCE: 4

| | |
|---|---|
| atgaaagcgg cagttgtcaa cgatttaaa caaaaattag aaattaaaga ggtggaaaaa | 60 |
| ccaaagctaa actacggaga agtgcttgtc aaaattgagg cttgcggcgt ttgccacacc | 120 |
| gatttgcatg cggcgcacgg agactggcca gtcaagccaa aactgccttt gattcccgga | 180 |
| cacgaagggg taggcattgt cgtcgaggtg gcagaagggg taaatcggt taaagtcggc | 240 |
| gaccgtgtcg gcattccatg gctatactcc gcttgcggag aatgtgaata ttgcctaagc | 300 |
| gggcaagaaa cgctctgtcc gcatcaatta aacggtggat attcgccga tggaggatat | 360 |
| gcggaatact gcaaagcgcc tgccaattat gttgcaaaaa ttccggaaca cttggatccg | 420 |
| gtggaagtcg cgccaattct ctgcgcgggt gtaacgacat ataaagcgct aaaggtatct | 480 |

```
aacgccaaac cgggagaatg ggtagccatc tacggaatcg gagggttagg gcatatcgcc    540
cttcaatacg cgaaagcaat gggattaaac gtcgtcgcgg tcgatattag cgacgaaaag    600
atagatctcg ccaaacagtt aggcgctgat attgccatca acggacgaaa agaggatcca    660
gtggaagcca ttcatcaaaa cgttggcgga gtacatgccg ccattagcgt tgccgtaacg    720
aaaaaagcgt tcgaacaagc ctatcaatcc gtaagacgcg gcggatgcct tgttgttgtc    780
ggactgccta atgaagactt gccgattcct attttcaata cggtattaaa cggaatcacg    840
gtgaaaggat cgatcgtcgg cacgagaaaa gatatgcaag aagcgttgga cttcgccgcg    900
aaaggaaaag tgcgcccgat cgtcgaaacc gctccattgg aaaaaatcaa tgaagtattt    960
gagagaatgg aaaaaggaaa aattaacggc cgagtcgttt taaccattgg tgtcaaccgc   1020
taa                                                                 1023

<210> SEQ ID NO 5
<211> LENGTH: 1041
<212> TYPE: DNA
<213> ORGANISM: Geobacillus thermoglucosidasius

<400> SEQUENCE: 5
atgaaagcac ttacatacct agggccagga aaaaagaat taatggaaaa accaaagcca     60
aaaattgaaa ggaaaccga tgcaatcgtc aaaataataa aaacaacgat tgtggaacg    120 gatttgcaca ttctttcagg agatgttcct actgttgaag aagggcggat tttaggacac    180
gaaggcgtcg gaattattga agaagttggt tcggccgtaa agaatttaa aaaaggcgac    240 agagtgttga tttcttgcat tacctcttgt ggaaaatgcg aaaattgcaa gaaagggtta    300
tacgcccatt gcgaagatgg cggctggatc ttgggccact taattgatgg aactcaagca    360
gaatatgtaa gaattccgca cgcagacaac agcctttatc ctattccgga aggcgtggat    420
gaagagactc ttgtcatgct tagtgacatt cttccaacag gatttgaaat cggcgtgttg    480
aacggcaaag ttcagcctgg acaaaccgtc gccattatcg gagctggtcc cgtaggtatg    540
gcagcgctat taacagccca attttattca ccagcagaga tcattatggt tgatttagac    600
gataaccgtt tagaagttgc gaaaaaattt ggcgcgaccc aagtggtgaa tagcgctgat    660
ggcaaggcag tggaaaaaat tatggaatta accggcggga aaggtgtaga cgtcgcgatg    720
gaagccgtcg gaattccggc aacatttgat atttgtcaag aaattgtcaa accaggtggc    780
tatatcgcca atatcggtgt tcatggaaaa agcgtggaat tcacattga aaaattatgg    840 atacgcaaca ttcgttgac aaccggtctt gtcaacacga cttctacgcc gatgttatta    900
aaaacggtgc agtcgaaaaa attgaagccg aacaattaa ttacccatcg tttcgccttt    960
tcagacatta tgaaagcgta tgaagtattt ggaaatgcag caaaagaaaa agcgttaaaa   1020
gtcattattt ccaacagtta a                                            1041

<210> SEQ ID NO 6
<211> LENGTH: 336
<212> TYPE: PRT
<213> ORGANISM: Klebsiella pneumoniae

<400> SEQUENCE: 6

Met Lys Ala Ala Val Val Thr His Asp His Gln Val Asn Val Thr Glu
1               5                   10                  15

Lys Thr Leu Arg Pro Leu Glu Tyr Gly Glu Ala Leu Leu Lys Met Glu
            20                  25                  30

Cys Cys Gly Val Cys His Thr Asp Leu His Val Lys Asn Gly Asp Phe
```

```
            35                  40                  45
Gly Asp Lys Thr Gly Val Ile Leu Gly His Glu Gly Ile Gly Val Val
 50                  55                  60

Gln Lys Val Gly Pro Gly Val Thr Ser Leu Lys Pro Gly Asp Arg Ala
 65                  70                  75                  80

Ser Val Ala Trp Phe Phe Glu Gly Cys Gly His Cys Asp Tyr Cys Asn
                 85                  90                  95

Ser Gly Asn Glu Thr Leu Cys Arg Ser Val Lys Asn Ala Gly Tyr Thr
            100                 105                 110

Val Asp Gly Gly Met Ala Glu Cys Ile Val Thr Ala Asn Tyr Ala
            115                 120                 125

Val Lys Val Pro Asp Gly Leu Asp Ser Ala Ala Ser Ser Ile Thr
130                 135                 140

Cys Ala Gly Val Thr Thr Tyr Lys Ala Val Lys Val Ser His Ile Lys
145                 150                 155                 160

Pro Gly Gln Trp Ile Ala Ile Tyr Gly Leu Gly Gly Leu Gly Asn Leu
                165                 170                 175

Ala Leu Gln Tyr Ala Lys Asn Val Phe Asn Ala Lys Val Ile Ala Ile
            180                 185                 190

Asp Val Asn Asp Gly Gln Leu Glu Leu Ala Ala Ser Met Gly Ala Asp
            195                 200                 205

Leu Thr Ile Asn Ser Arg Asn Glu Asp Ala Ala Lys Val Ile Gln Glu
210                 215                 220

Lys Thr Gly Gly Ala His Ala Ala Val Val Thr Ala Val Ala Lys Ala
225                 230                 235                 240

Ala Phe Asn Ser Ala Val Asp Ala Val Arg Ala Gly Gly Arg Val Val
                245                 250                 255

Ala Val Gly Leu Pro Pro Glu Ala Met Ser Leu Asp Ile Pro Arg Leu
            260                 265                 270

Val Leu Asp Gly Ile Glu Val Val Gly Ser Leu Val Gly Thr Arg Gln
            275                 280                 285

Asp Leu Val Glu Ala Phe Gln Phe Ala Ala Glu Gly Lys Val Val Pro
290                 295                 300

Lys Val Thr Leu Arg Pro Leu Glu Asp Ile Asn Ala Ile Phe Lys Glu
305                 310                 315                 320

Met Glu Gln Gly Gln Ile Arg Gly Arg Met Val Ile Asp Leu Arg Ser
                325                 330                 335

<210> SEQ ID NO 7
<211> LENGTH: 336
<212> TYPE: PRT
<213> ORGANISM: Geobacillus thermocatenulatus

<400> SEQUENCE: 7

Met Lys Ala Ala Val Val His Lys Phe Lys Gln Lys Leu Gln Ile Glu
  1               5                  10                  15

Glu Val Glu Lys Pro Lys Leu Gly Tyr Gly Glu Val Leu Val Lys Ile
             20                  25                  30

Glu Ala Cys Gly Val Cys His Thr Asp Leu His Ala Ala His Gly Asp
         35                  40                  45

Trp Pro Val Lys Pro Lys Leu Pro Leu Ile Pro Gly His Glu Gly Val
 50                  55                  60

Gly Ile Val Val Glu Val Gly Glu Gly Val Lys Ser Ile Lys Ile Gly
 65                  70                  75                  80
```

```
Asp Arg Val Gly Ile Pro Trp Leu Tyr Ser Ala Cys Gly Glu Cys Glu
                85                  90                  95

Tyr Cys Leu Ser Gly Gln Glu Thr Leu Cys Pro His Gln Leu Asn Gly
            100                 105                 110

Gly Tyr Ser Val Asp Gly Ser Tyr Ala Glu Tyr Cys Lys Ala Pro Ala
        115                 120                 125

Asp Tyr Val Ala Arg Ile Pro Lys Asn Leu Asp Pro Val Gln Val Ala
    130                 135                 140

Pro Ile Leu Cys Ala Gly Val Thr Thr Tyr Lys Ala Leu Lys Val Ser
145                 150                 155                 160

Asn Ala Lys Pro Gly Glu Trp Val Ala Ile Tyr Gly Ile Gly Gly Leu
                165                 170                 175

Gly His Ile Ala Leu Gln Tyr Ala Lys Ala Met Gly Leu Asn Val Val
            180                 185                 190

Ala Val Asp Ile Ser Asp Glu Lys Ala Glu Leu Ala Ala Lys Leu Gly
        195                 200                 205

Ala Asp Ile Thr Ile Asn Gly Leu Arg Glu Asp Pro Val Ala Thr Ile
    210                 215                 220

Arg Glu Lys Val Gly Gly Val His Ala Ala Ile Ser Val Ala Val Thr
225                 230                 235                 240

Lys Lys Ala Phe Glu Gln Ala Tyr Gln Ser Val Arg Arg Gly Gly Cys
                245                 250                 255

Leu Val Ile Val Gly Leu Pro His Asp Glu Leu Pro Ile Pro Ile Phe
            260                 265                 270

Asp Thr Val Leu Asn Gly Val Thr Ile Lys Gly Ser Ile Val Gly Thr
        275                 280                 285

Arg Lys Asp Met Gln Glu Ala Leu Asp Phe Ala Ala Arg Gly Lys Val
    290                 295                 300

Arg Pro Ile Val Glu Ala Val Pro Leu Glu Lys Ile Asn Glu Val Phe
305                 310                 315                 320

Glu Arg Met Glu Lys Gly Gln Ile Asn Gly Arg Ile Val Leu Thr Met
                325                 330                 335

<210> SEQ ID NO 8
<211> LENGTH: 340
<212> TYPE: PRT
<213> ORGANISM: Geobacillus thermoglucosidasius

<400> SEQUENCE: 8

Met Lys Ala Ala Val Val Asn Asp Phe Lys Gln Lys Leu Glu Ile Lys
1               5                   10                  15

Glu Val Glu Lys Pro Lys Leu Asn Tyr Gly Glu Val Leu Val Lys Ile
            20                  25                  30

Glu Ala Cys Gly Val Cys His Thr Asp Leu His Ala Ala His Gly Asp
        35                  40                  45

Trp Pro Val Lys Pro Lys Leu Pro Leu Ile Pro Gly His Glu Gly Val
    50                  55                  60

Gly Ile Val Val Glu Val Ala Glu Gly Val Lys Ser Val Lys Val Gly
65                  70                  75                  80

Asp Arg Val Gly Ile Pro Trp Leu Tyr Ser Ala Cys Gly Glu Cys Glu
                85                  90                  95

Tyr Cys Leu Ser Gly Gln Glu Thr Leu Cys Pro His Gln Leu Asn Gly
            100                 105                 110

Gly Tyr Ser Ala Asp Gly Gly Tyr Ala Glu Tyr Cys Lys Ala Pro Ala
        115                 120                 125
```

Asn Tyr Val Ala Lys Ile Pro Glu His Leu Asp Pro Val Glu Val Ala
            130                 135                 140

Pro Ile Leu Cys Ala Gly Val Thr Thr Tyr Lys Ala Leu Lys Val Ser
145                 150                 155                 160

Asn Ala Lys Pro Gly Glu Trp Val Ala Ile Tyr Gly Ile Gly Gly Leu
                165                 170                 175

Gly His Ile Ala Leu Gln Tyr Ala Lys Ala Met Gly Leu Asn Val Val
            180                 185                 190

Ala Val Asp Ile Ser Asp Glu Lys Ile Asp Leu Ala Lys Gln Leu Gly
            195                 200                 205

Ala Asp Ile Ala Ile Asn Gly Arg Lys Glu Asp Pro Val Glu Ala Ile
210                 215                 220

His Gln Asn Val Gly Gly Val His Ala Ala Ile Ser Val Ala Val Thr
225                 230                 235                 240

Lys Lys Ala Phe Glu Gln Ala Tyr Gln Ser Val Arg Arg Gly Gly Cys
                245                 250                 255

Leu Val Val Gly Leu Pro Asn Glu Asp Leu Pro Ile Pro Ile Phe
                260                 265                 270

Asn Thr Val Leu Asn Gly Ile Thr Val Lys Gly Ser Ile Val Gly Thr
            275                 280                 285

Arg Lys Asp Met Gln Glu Ala Leu Asp Phe Ala Ala Lys Gly Lys Val
290                 295                 300

Arg Pro Ile Val Glu Thr Ala Pro Leu Glu Lys Ile Asn Glu Val Phe
305                 310                 315                 320

Glu Arg Met Glu Lys Gly Lys Ile Asn Gly Arg Val Val Leu Thr Ile
                325                 330                 335

Gly Val Asn Arg
            340

<210> SEQ ID NO 9
<211> LENGTH: 346
<212> TYPE: PRT
<213> ORGANISM: Geobacillus thermoglucosidasius

<400> SEQUENCE: 9

Met Lys Ala Leu Thr Tyr Leu Gly Pro Gly Lys Lys Glu Leu Met Glu
1               5                   10                  15

Lys Pro Lys Pro Lys Ile Glu Lys Glu Thr Asp Ala Ile Val Lys Ile
                20                  25                  30

Ile Lys Thr Thr Ile Cys Gly Thr Asp Leu His Ile Leu Ser Gly Asp
            35                  40                  45

Val Pro Thr Val Glu Glu Gly Arg Ile Leu Gly His Glu Gly Val Gly
50                  55                  60

Ile Ile Glu Glu Val Gly Ser Ala Val Lys Asn Phe Lys Lys Gly Asp
65                  70                  75                  80

Arg Val Leu Ile Ser Cys Ile Ser Cys Gly Lys Cys Glu Asn Cys
                85                  90                  95

Lys Lys Gly Leu Tyr Ala His Cys Glu Asp Gly Gly Trp Ile Leu Gly
                100                 105                 110

His Leu Ile Asp Gly Thr Gln Ala Glu Tyr Val Arg Ile Pro His Ala
            115                 120                 125

Asp Asn Ser Leu Tyr Pro Ile Pro Glu Gly Val Asp Glu Glu Thr Leu
            130                 135                 140

Val Met Leu Ser Asp Ile Leu Pro Thr Gly Phe Glu Ile Gly Val Leu

```
                145                 150                 155                 160
Asn Gly Lys Val Gln Pro Gly Gln Thr Val Ala Ile Ile Gly Ala Gly
                165                 170                 175

Pro Val Gly Met Ala Ala Leu Leu Thr Ala Gln Phe Tyr Ser Pro Ala
            180                 185                 190

Glu Ile Ile Met Val Asp Leu Asp Asp Asn Arg Leu Glu Val Ala Lys
        195                 200                 205

Lys Phe Gly Ala Thr Gln Val Val Asn Ser Ala Asp Gly Lys Ala Val
    210                 215                 220

Glu Lys Ile Met Glu Leu Thr Gly Gly Lys Gly Val Asp Val Ala Met
225                 230                 235                 240

Glu Ala Val Gly Ile Pro Ala Thr Phe Asp Ile Cys Gln Glu Ile Val
                245                 250                 255

Lys Pro Gly Gly Tyr Ile Ala Asn Ile Gly Val His Gly Lys Ser Val
            260                 265                 270

Glu Phe His Ile Glu Lys Leu Trp Ile Arg Asn Ile Thr Leu Thr Thr
        275                 280                 285

Gly Leu Val Asn Thr Thr Ser Thr Pro Met Leu Leu Lys Thr Val Gln
    290                 295                 300

Ser Lys Lys Leu Lys Pro Glu Gln Leu Ile Thr His Arg Phe Ala Phe
305                 310                 315                 320

Ser Asp Ile Met Lys Ala Tyr Glu Val Phe Gly Asn Ala Ala Lys Glu
                325                 330                 335

Lys Ala Leu Lys Val Ile Ile Ser Asn Ser
            340                 345
```

<210> SEQ ID NO 10
<211> LENGTH: 1692
<212> TYPE: DNA
<213> ORGANISM: Gluconobacter oxydans

<400> SEQUENCE: 10

```
atgacttata ctgtcggaca ttatcttgcc gaacgactga cacagatcgg cctgaagcat      60
catttcgccg ttgccggcga ctacaacctc gttctgctcg accagctgat cgaacagggc     120
ggcacgaagc agatctatga ctgcaacgag ctgaactgca gcttcgccgc cgaaggttat     180
gcccgcgcca acggtgcagc cgctgccgtc atcaccttca gcgtcggcgc catctccgcc     240
atgaacggcc tcggcggcgc ctatgccgag aacctgccga tcctcgtgat ttcgggcgct     300
ccgaactcca cgatcacgg ttcgggccac gtcctgcacc acgcgatcgg cacgacggac     360
tacagctacc agatggaaat ggcgaagcac gttacctgtg ccgccgaaag catcacctct     420
gctgaaaccg ccccggccaa gatcgaccac gtcatccgca cgatgctgcg tgagaagaag     480
ccggcctatc tcgaaatcgc ctgcaacatc tcggccgcac cctgcgtccg tccgggcccg     540
gtctcgtccc tgcacgccca tccgcgtccg acgaagccac gctgaaggc cgctctggac     600
gagagcctga gcttcctcaa caaggccaac aaggtcgcca tcctggtcgg caccaagctg     660
cgcgcagccg aagccctcaa ggaaacggtc gaactggctg acaagctcgg ttgccccgtt     720
acggtcatgg ccgctgcaaa gagctacttc cccgagacgc accccggctt ccgtggcgtg     780
tactggggcg acgtcagcag cccgggcgcc caggaaatca tcgaaggcgc cgatgccgtc     840
atctgcctgg caccagtctg gaatgactac tcctcgggcg gctggaagag cgttgtccgt     900
ggcgaaaagg tcctcgaggt cgatcccaac cgcgtcaccg tcaacggcaa gaccttcgaa     960
ggcttccgcc tgaaggaatt cgtcaaggcc ctgaccgaga aggctccgaa gaagtccgca    1020
```

```
gccctgaccg cgaatacaa gcccgtcatg ctgcctaagg ccgacccgtc caagccgctg    1080
tccaacgacg aaatgacccg ccagatcaac gaactggtcg acggcaacac cacgctcttc    1140
gccgagaccg cgactcatg gttcaacgcc gtgcgtatgc accttcccga aggtgcgaag    1200
gtcgagacgc aaatgcagtg gggtcacatc ggctggtccg ttccgtccat gttcggcaac    1260
gccaccgctt cgccggagcg caagcacgtc ctgatggtcg gtgacggttc cttccagctg    1320
acggcgcagg aagtggccca gatggtccgc tacgaactgc cggtcatcat cttcctggtg    1380
aacaaccacg gctacgtcat cgaaatcgcc atccatgacg cccgtacaa ctacatccag    1440 aactgggact acgcagctct gatgcagtgc ttcaaccagg cgtcccggg cgaggaaagc    1500 ggcaagtacg gtctcggcct gcatgccacg accggtgcag aactggccga agccatcgcc    1560
aaggccaaga gaacacccg cggcccgacg ctcatcgagt gcaagcttga tcgtacggac    1620
tgcaccaaga ccctcgtgga gtggggcaag gctgttgccg ccgcaaactc ccgcaagccc    1680
cagagcgtct aa                                                       1692

<210> SEQ ID NO 11
<211> LENGTH: 563
<212> TYPE: PRT
<213> ORGANISM: Gluconobacter oxydans

<400> SEQUENCE: 11

Met Thr Tyr Thr Val Gly His Tyr Leu Ala Glu Arg Leu Thr Gln Ile
1               5                   10                  15

Gly Leu Lys His His Phe Ala Val Ala Gly Asp Tyr Asn Leu Val Leu
            20                  25                  30

Leu Asp Gln Leu Ile Glu Gln Gly Gly Thr Lys Gln Ile Tyr Asp Cys
        35                  40                  45

Asn Glu Leu Asn Cys Ser Phe Ala Ala Glu Gly Tyr Ala Arg Ala Asn
    50                  55                  60

Gly Ala Ala Ala Val Ile Thr Phe Ser Val Gly Ala Ile Ser Ala
65                  70                  75                  80

Met Asn Gly Leu Gly Gly Ala Tyr Ala Glu Asn Leu Pro Ile Leu Val
                85                  90                  95

Ile Ser Gly Ala Pro Asn Ser Asn Asp His Gly Ser Gly His Val Leu
            100                 105                 110

His His Thr Ile Gly Thr Thr Asp Tyr Ser Tyr Gln Met Glu Met Ala
        115                 120                 125

Lys His Val Thr Cys Ala Ala Glu Ser Ile Thr Ser Ala Glu Thr Ala
    130                 135                 140

Pro Ala Lys Ile Asp His Val Ile Arg Thr Met Leu Arg Glu Lys Lys
145                 150                 155                 160

Pro Ala Tyr Leu Glu Ile Ala Cys Asn Ile Ser Ala Ala Pro Cys Val
                165                 170                 175

Arg Pro Gly Pro Val Ser Ser Leu His Ala His Pro Arg Pro Asp Glu
            180                 185                 190

Ala Ser Leu Lys Ala Ala Leu Asp Glu Ser Leu Ser Phe Leu Asn Lys
        195                 200                 205

Ala Asn Lys Val Ala Ile Leu Val Gly Thr Lys Leu Arg Ala Ala Glu
    210                 215                 220

Ala Leu Lys Glu Thr Val Glu Leu Ala Asp Lys Leu Gly Cys Pro Val
225                 230                 235                 240

Thr Val Met Ala Ala Ala Lys Ser Tyr Phe Pro Glu Thr His Pro Gly
```

```
                          245                 250                 255
Phe Arg Gly Val Tyr Trp Gly Asp Val Ser Ser Pro Gly Ala Gln Glu
                260                 265                 270
Ile Ile Glu Gly Ala Asp Ala Val Ile Cys Leu Ala Pro Val Trp Asn
            275                 280                 285
Asp Tyr Ser Ser Gly Gly Trp Lys Ser Val Val Arg Gly Glu Lys Val
        290                 295                 300
Leu Glu Val Asp Pro Asn Arg Val Thr Val Asn Gly Lys Thr Phe Glu
305                 310                 315                 320
Gly Phe Arg Leu Lys Glu Phe Val Lys Ala Leu Thr Glu Lys Ala Pro
                325                 330                 335
Lys Lys Ser Ala Ala Leu Thr Gly Glu Tyr Lys Pro Val Met Leu Pro
                340                 345                 350
Lys Ala Asp Pro Ser Lys Pro Leu Ser Asn Asp Glu Met Thr Arg Gln
            355                 360                 365
Ile Asn Glu Leu Val Asp Gly Asn Thr Thr Leu Phe Ala Glu Thr Gly
        370                 375                 380
Asp Ser Trp Phe Asn Ala Val Arg Met His Leu Pro Glu Gly Ala Lys
385                 390                 395                 400
Val Glu Thr Glu Met Gln Trp Gly His Ile Gly Trp Ser Val Pro Ser
                405                 410                 415
Met Phe Gly Asn Ala Thr Ala Ser Pro Glu Arg Lys His Val Leu Met
                420                 425                 430
Val Gly Asp Gly Ser Phe Gln Leu Thr Ala Gln Glu Val Ala Gln Met
            435                 440                 445
Val Arg Tyr Glu Leu Pro Val Ile Ile Phe Leu Val Asn Asn His Gly
        450                 455                 460
Tyr Val Ile Glu Ile Ala Ile His Asp Gly Pro Tyr Asn Tyr Ile Gln
465                 470                 475                 480
Asn Trp Asp Tyr Ala Ala Leu Met Gln Cys Phe Asn Gln Gly Val Pro
                485                 490                 495
Gly Glu Glu Ser Gly Lys Tyr Gly Leu Gly Leu His Ala Thr Thr Gly
                500                 505                 510
Ala Glu Leu Ala Glu Ala Ile Ala Lys Ala Lys Asn Thr Arg Gly
            515                 520                 525
Pro Thr Leu Ile Glu Cys Lys Leu Asp Arg Thr Asp Cys Thr Lys Thr
        530                 535                 540
Leu Val Glu Trp Gly Lys Ala Val Ala Ala Asn Ser Arg Lys Pro
545                 550                 555                 560
Gln Ser Val

<210> SEQ ID NO 12
<211> LENGTH: 2676
<212> TYPE: DNA
<213> ORGANISM: Escherichia coli

<400> SEQUENCE: 12
atggctgtta ctaatgtcgc tgaacttaac gcactcgtag agcgtgtaaa aaaagcccag     60
cgtgaatatg ccagtttcac tcaagagcaa gtagacaaaa tcttccgcgc cgccgctctg    120
gctgctgcag atgctcgaat cccactcgcg aaaatggccg ttgccgaatc cggcatgggt    180
atcgtcgaag ataaagtgat caaaaaccac tttgcttctg aatatatcta caacgcctat    240
aaagatgaaa aaacctgtgg tgttctgtct gaagacgaca cttttggtac catcactatc    300
```

```
gctgaaccaa tcggtattat tgcggtatc gttccgacca ctaacccgac ttcaactgct    360
atcttcaaat cgctgatcag tctgaagacc cgtaacgcca ttatcttctc cccgcacccg    420
cgtgcaaaag atgccaccaa caaagcggct gatatcgttc tgcaggctgc tatcgctgcc    480
ggtgctccga agatctgat cggctggatc gatcaacctt ctgttgaact gtctaacgca    540
ctgatgcacc acccagacat caacctgatc ctcgcgactg gtggtccggg catggttaaa    600
gccgcataca gctccggtaa accagctatc ggtgtaggcg cgggcaacac tccagttgtt    660
atcgatgaaa ctgctgatat caaacgtgca gttgcatctg tactgatgtc caaaaccttc    720
gacaacggcg taatctgtgc ttctgaacag tctgttgttg ttgttgactc tgtttatgac    780
gctgtacgtg aacgttttgc aacccacggc ggctatctgt tgcagggtaa agagctgaaa    840
gctgttcagg atgttatcct gaaaaacggt gcgctgaacg cggctatcgt tggtcagcca    900
gcctataaaa ttgctgaact ggcaggcttc tctgtaccag aaaacaccaa gattctgatc    960
ggtgaagtga ccgttgttga tgaaagcgaa ccgttcgcac atgaaaaact gtccccgact   1020
ctggcaatgt accgcgctaa agatttcgaa gacgcggtag aaaaagcaga gaaactggtt   1080
gctatgggcg gtatcggtca tacctcttgc ctgtacactg accaggataa ccaaccggct   1140
cgcgtttctt acttcggtca gaaaatgaaa acggcgcgta tcctgattaa caccccagcg   1200
tctcagggtg gtatcggtga cctgtataac ttcaaactcg caccttccct gactctgggt   1260
tgtggttctt ggggtggtaa ctccatctct gaaaacgttg gtccgaaaca cctgatcaac   1320
aagaaaaccg ttgctaagcg agctgaaaac atgttgtggc acaaacttcc gaaatctatc   1380
tacttccgcc gtggctccct gccaatcgcg ctggatgaag tgattactga tggccacaaa   1440
cgtgcgctca tcgtgactga ccgcttcctg ttcaacaatg gttatgctga tcagatcact   1500
tccgtactga aagcagcagg cgttgaaact gaagtcttct tcgaagtaga agcggacccg   1560
accctgagca tcgttcgtaa aggtgcagaa ctggcaaact ccttcaaacc agacgtgatt   1620
atcgcgctgg gtggtggttc cccgatggac gccgcgaaga tcatgtgggt tatgtacgaa   1680
catccggaaa ctcacttcga agagctggcg ctgcgcttta tggatatccg taaacgtatc   1740
tacaagttcc cgaaaatggg cgtgaaagcg aaaatgatcg ctgtcaccac cacttctggt   1800
acaggttctg aagtcactcc gtttgcggtt gtaactgacg acgctactgg tcagaaatat   1860
ccgctggcag actatgcgct gactccggat atggcgattg tcgacgccaa cctggttatg   1920
gacatgccga gtccctgtg tgctttcggt ggtctggacg cagtaactca cgccatggaa   1980
gcttatgttt ctgtactggc atctgagttc tctgatggtc aggctctgca ggcactgaaa   2040
ctgctgaaag aatatctgcc agcgtcctac cacgaagggt ctaaaaatcc ggtagcgcgt   2100
gaacgtgttc acagtgcagc gactatcgcg ggtatcgcgt ttgcgaacgc cttcctgggt   2160
gtatgtcact caatggcgca caaactgggt tcccagttcc atattccgca cggtctggca   2220
aacgccctgc tgatttgtaa cgttattcgc tacaatgcga acgacaaccc gaccaagcag   2280
actgcattca gccagtatga ccgtccgcag gctcgccgtc gttatgctga aattgccgac   2340
cacttgggtc tgagcgcacc gggcgaccgt actgctgcta agatcgagaa actgctggca   2400
tggctgaaaa cgctgaaagc tgaactgggt attccgaaat ctatccgtga agctggcgtt   2460
caggaagcag acttcctggc gaacgtggat aaactgtctg aagatgcatt cgatgaccag   2520
tgcaccggcg ctaacccgcg ttacccgctg atctccgagc tgaaacagat tctgctggat   2580
acctactacg tcgtgattta tgtagaaggt gaaactgcag cgaagaaaga agctgctccg   2640
gctaaagctg agaaaaaagc gaaaaaatcc gcttaa                            2676
```

<210> SEQ ID NO 13
<211> LENGTH: 2622
<212> TYPE: DNA
<213> ORGANISM: Clostridium thermocellum

<400> SEQUENCE: 13

| | | |
|---|---|---|
| atgacgaaaa tagcgaataa atacgaagtt attgataatg ttgaaaagct tgaaaaggct | 60 |
| ttgaaacgtt taagagaagc tcaaagtgtt tatgcaacct atacacagga gcaggttgac | 120 |
| aaaattttct ttgaggcggc aatggcggcc aataaaatga attcctct tgccaaaatg | 180 |
| gctgtggagg aaacaggcat gggagtggtt gaagacaagg ttatcaaaaa ccactatgct | 240 |
| tctgagtata tctataatgc gtacaaaaac actaaaacct gcggtgttat tgaagaggac | 300 |
| cctgctttcg gtattaaaaa aatagcagag ccttttgggg ttattgcggc ggttatacct | 360 |
| actacgaatc cgacatcgac agcaatcttt aagactctta ttgcattaaa gacgagaaat | 420 |
| gcaattatta taagcccaca ccccagggca aaaaactcaa cgatagaagc ggcgaaaatt | 480 |
| gttttggagg cggccgttaa agccggtgct ccggaaggca tcattggctg gattgatgtg | 540 |
| ccgagccttg aacttaccaa cctggtaatg agagaagcag atgtgattct cgcaacaggc | 600 |
| ggtcccggac tggttaaagc agcttactct tcgggcaaac cggctattgg tgtcggagcg | 660 |
| ggcaatactc ctgcaattat tgatgattcg gccgacattg tcttggcagt gaactcaata | 720 |
| atacattcaa aactttcga caacggtatg atttgtgctt cagagcaatc ggtcattgtt | 780 |
| ctggacgggg tatataaaga ggtaaaaaaa gaatttgaaa aaagaggatg ctatttctta | 840 |
| aatgaagatg aaactgaaaa ggtaagaaaa acaattataa taaacggtgc gttaaatgcc | 900 |
| aagatagtag gtcagaaagc tcacacaatt gcaaaccttg caggttttga ggtacccgag | 960 |
| actacaaaaa ttctgatagg cgaagttacc agcgtggata tttccgaaga atttgcccac | 1020 |
| gaaaagttgt gcccggtact ggcaatgtac agggcaaagg attttgacga tgcccttgat | 1080 |
| aaagcagaaa ggttggtagc tgacggtgga tttggccata cttcgtcact ttatatagat | 1140 |
| acggtaacac agaaagagaa acttcagaaa ttctctgaaa ggatgaaaac ctgccgtata | 1200 |
| ttggttaata cgccgtcatc ccagggaggt atcggtgacc tttacaactt caagcttgct | 1260 |
| ccgtctctca ccctcggctg cggttcctgg ggaggaaatt cagtttccga caatgtggga | 1320 |
| gtcaagcatt tgttaaacat taaaacagtt gccgagagga gagagaacat gctctggttc | 1380 |
| agaacacctg aaaagattta tataaaaaga ggttgtctgc ctgttgcatt ggatgagctt | 1440 |
| aaaaatgtaa tgggtaaaaa gaaagcattt attgtaacgg ataacttcct gtacaataac | 1500 |
| ggctacacca agccgattac ggataagctg gatgaaatgg gaattgtgca caagaccttc | 1560 |
| tttgatgtgt ctccagaccc atcccttgca tctgccaaag ccggtgcggc agaaatgctg | 1620 |
| gctttccagc ctgacaccat aattgcggtc ggcggcggat ctgccatgga cgcggccaaa | 1680 |
| atcatgtggg tgatgtatga acatccggaa gttgacttta tggacatggc aatgagattt | 1740 |
| atggatataa gaaagagagt ttacaccttc ccgaagatgg gacagaaggc atactttatc | 1800 |
| gcaattccga cttccgcggg tacaggttca gaagtgacac cttttgcggt tattactgat | 1860 |
| gaaaaaacag gaattaaata ccctctggcc gactatgaat gttgccgga catggctatt | 1920 |
| gtagatgccg atatgatgat gaatgctcca aagggactta ccgcagcttc cggtatagac | 1980 |
| gcattgaccc acgctctgga agcctatgtt tcaatgcttg cgaccgacta tacggatagc | 2040 |
| cttgcccttc gtgcaataaa gatgatattt gaatatctcc cgagagccta tgaaaacggt | 2100 |

-continued

```
gcaagtgacc cggttgcaag agagaaaatg gccaatgccg caacaatagc cggaatggct    2160
tttgccaatg ccttttggg tgtatgccat tcaatggcgc acaaactggg tgcttttat    2220 cacctgcccc acggtgttgc caatgcactt atgataaacg aagtaatcag attcaactca    2280
tccgaggctc cgaccaagat gggtactttc ccgcagtatg accatccgcg cacgctggaa    2340
aggtatgcag aaattgccga ttatatcgga cttaagggca agaataacga agaaaaagtt    2400
gaaaacttga ttaaagctat tgatgagctt aagaaaaagg tgggcatcag gaagaccatc    2460
aaagattatg acatagatga aaaggaattt ttggacagac tggacgaaat ggtggaacag    2520
gcttttgacg accagtgcac aggtacaaat ccaagatacc cgcttatgaa tgaaatcagg    2580
caaatgtatc tgaacgctta ttacggaggt gcgaagaaat aa                      2622
```

<210> SEQ ID NO 14
<211> LENGTH: 891
<212> TYPE: PRT
<213> ORGANISM: Escherichia coli

<400> SEQUENCE: 14

```
Met Ala Val Thr Asn Val Ala Glu Leu Asn Ala Leu Val Glu Arg Val
1               5                   10                  15

Lys Lys Ala Gln Arg Glu Tyr Ala Ser Phe Thr Gln Glu Gln Val Asp
            20                  25                  30

Lys Ile Phe Arg Ala Ala Ala Leu Ala Ala Ala Asp Ala Arg Ile Pro
        35                  40                  45

Leu Ala Lys Met Ala Val Ala Glu Ser Gly Met Gly Ile Val Glu Asp
    50                  55                  60

Lys Val Ile Lys Asn His Phe Ala Ser Glu Tyr Ile Tyr Asn Ala Tyr
65                  70                  75                  80

Lys Asp Glu Lys Thr Cys Gly Val Leu Ser Asp Asp Thr Phe Gly
                85                  90                  95

Thr Ile Thr Ile Ala Glu Pro Ile Gly Ile Ile Cys Gly Ile Val Pro
            100                 105                 110

Thr Thr Asn Pro Thr Ser Thr Ala Ile Phe Lys Ser Leu Ile Ser Leu
        115                 120                 125

Lys Thr Arg Asn Ala Ile Ile Phe Ser Pro His Pro Arg Ala Lys Asp
    130                 135                 140

Ala Thr Asn Lys Ala Ala Asp Ile Val Leu Gln Ala Ala Ile Ala Ala
145                 150                 155                 160

Gly Ala Pro Lys Asp Leu Ile Gly Trp Ile Asp Gln Pro Ser Val Glu
                165                 170                 175

Leu Ser Asn Ala Leu Met His His Pro Asp Ile Asn Leu Ile Leu Ala
            180                 185                 190

Thr Gly Gly Pro Gly Met Val Lys Ala Ala Tyr Ser Ser Gly Lys Pro
        195                 200                 205

Ala Ile Gly Val Gly Ala Gly Asn Thr Pro Val Val Ile Asp Glu Thr
    210                 215                 220

Ala Asp Ile Lys Arg Ala Val Ala Ser Val Leu Met Ser Lys Thr Phe
225                 230                 235                 240

Asp Asn Gly Val Ile Cys Ala Ser Glu Gln Ser Val Val Val Asp
                245                 250                 255

Ser Val Tyr Asp Ala Val Arg Glu Arg Phe Ala Thr His Gly Gly Tyr
            260                 265                 270

Leu Leu Gln Gly Lys Glu Leu Lys Ala Val Gln Asp Val Ile Leu Lys
        275                 280                 285
```

-continued

Asn Gly Ala Leu Asn Ala Ala Ile Val Gly Gln Pro Ala Tyr Lys Ile
            290                 295                 300

Ala Glu Leu Ala Gly Phe Ser Val Pro Glu Asn Thr Lys Ile Leu Ile
305                 310                 315                 320

Gly Glu Val Thr Val Asp Glu Ser Glu Pro Phe Ala His Glu Lys
                325                 330                 335

Leu Ser Pro Thr Leu Ala Met Tyr Arg Ala Lys Asp Phe Glu Asp Ala
                340                 345                 350

Val Glu Lys Ala Glu Lys Leu Val Ala Met Gly Gly Ile Gly His Thr
            355                 360                 365

Ser Cys Leu Tyr Thr Asp Gln Asp Asn Gln Pro Ala Arg Val Ser Tyr
370                 375                 380

Phe Gly Gln Lys Met Lys Thr Ala Arg Ile Leu Ile Asn Thr Pro Ala
385                 390                 395                 400

Ser Gln Gly Gly Ile Gly Asp Leu Tyr Asn Phe Lys Leu Ala Pro Ser
                405                 410                 415

Leu Thr Leu Gly Cys Gly Ser Trp Gly Gly Asn Ser Ile Ser Glu Asn
                420                 425                 430

Val Gly Pro Lys His Leu Ile Asn Lys Lys Thr Val Ala Lys Arg Ala
            435                 440                 445

Glu Asn Met Leu Trp His Lys Leu Pro Lys Ser Ile Tyr Phe Arg Arg
450                 455                 460

Gly Ser Leu Pro Ile Ala Leu Asp Glu Val Ile Thr Asp Gly His Lys
465                 470                 475                 480

Arg Ala Leu Ile Val Thr Asp Arg Phe Leu Phe Asn Asn Gly Tyr Ala
                485                 490                 495

Asp Gln Ile Thr Ser Val Leu Lys Ala Ala Gly Val Glu Thr Glu Val
                500                 505                 510

Phe Phe Glu Val Glu Ala Asp Pro Thr Leu Ser Ile Val Arg Lys Gly
            515                 520                 525

Ala Glu Leu Ala Asn Ser Phe Lys Pro Asp Val Ile Ala Leu Gly
            530                 535                 540

Gly Gly Ser Pro Met Asp Ala Ala Lys Ile Met Trp Val Met Tyr Glu
545                 550                 555                 560

His Pro Glu Thr His Phe Glu Glu Leu Ala Leu Arg Phe Met Asp Ile
                565                 570                 575

Arg Lys Arg Ile Tyr Lys Phe Pro Lys Met Gly Val Lys Ala Lys Met
                580                 585                 590

Ile Ala Val Thr Thr Thr Ser Gly Thr Gly Ser Glu Val Thr Pro Phe
            595                 600                 605

Ala Val Val Thr Asp Asp Ala Thr Gly Gln Lys Tyr Pro Leu Ala Asp
            610                 615                 620

Tyr Ala Leu Thr Pro Asp Met Ala Ile Val Asp Ala Asn Leu Val Met
625                 630                 635                 640

Asp Met Pro Lys Ser Leu Cys Ala Phe Gly Gly Leu Asp Ala Val Thr
                645                 650                 655

His Ala Met Glu Ala Tyr Val Ser Val Leu Ala Ser Glu Phe Ser Asp
                660                 665                 670

Gly Gln Ala Leu Gln Ala Leu Lys Leu Leu Lys Glu Tyr Leu Pro Ala
            675                 680                 685

Ser Tyr His Glu Gly Ser Lys Asn Pro Val Ala Arg Glu Arg Val His
            690                 695                 700

```
Ser Ala Ala Thr Ile Ala Gly Ile Ala Phe Ala Asn Ala Phe Leu Gly
705                 710                 715                 720

Val Cys His Ser Met Ala His Lys Leu Gly Ser Gln Phe His Ile Pro
                725                 730                 735

His Gly Leu Ala Asn Ala Leu Leu Ile Cys Asn Val Ile Arg Tyr Asn
            740                 745                 750

Ala Asn Asp Asn Pro Thr Lys Gln Thr Ala Phe Ser Gln Tyr Asp Arg
        755                 760                 765

Pro Gln Ala Arg Arg Tyr Ala Glu Ile Ala Asp His Leu Gly Leu
    770                 775                 780

Ser Ala Pro Gly Asp Arg Thr Ala Ala Lys Ile Glu Lys Leu Leu Ala
785                 790                 795                 800

Trp Leu Glu Thr Leu Lys Ala Glu Leu Gly Ile Pro Lys Ser Ile Arg
                805                 810                 815

Glu Ala Gly Val Gln Glu Ala Asp Phe Leu Ala Asn Val Asp Lys Leu
            820                 825                 830

Ser Glu Asp Ala Phe Asp Gln Cys Thr Gly Ala Asn Pro Arg Tyr
        835                 840                 845

Pro Leu Ile Ser Glu Leu Lys Gln Ile Leu Leu Asp Thr Tyr Tyr Gly
    850                 855                 860

Arg Asp Tyr Val Glu Gly Glu Thr Ala Ala Lys Lys Glu Ala Ala Pro
865                 870                 875                 880

Ala Lys Ala Glu Lys Lys Ala Lys Lys Ser Ala
                885                 890

<210> SEQ ID NO 15
<211> LENGTH: 873
<212> TYPE: PRT
<213> ORGANISM: Clostridium thermocellum

<400> SEQUENCE: 15

Met Thr Lys Ile Ala Asn Lys Tyr Glu Val Ile Asp Asn Val Glu Lys
1               5                   10                  15

Leu Glu Lys Ala Leu Lys Arg Leu Arg Glu Ala Gln Ser Val Tyr Ala
                20                  25                  30

Thr Tyr Thr Gln Glu Gln Val Asp Lys Ile Phe Phe Glu Ala Ala Met
            35                  40                  45

Ala Ala Asn Lys Met Arg Ile Pro Leu Ala Lys Met Ala Val Glu Glu
        50                  55                  60

Thr Gly Met Gly Val Val Glu Asp Lys Val Ile Lys Asn His Tyr Ala
65                  70                  75                  80

Ser Glu Tyr Ile Tyr Asn Ala Tyr Lys Asn Thr Lys Thr Cys Gly Val
                85                  90                  95

Ile Glu Glu Asp Pro Ala Phe Gly Ile Lys Lys Ile Ala Glu Pro Leu
            100                 105                 110

Gly Val Ile Ala Ala Val Ile Pro Thr Thr Asn Pro Thr Ser Thr Ala
        115                 120                 125

Ile Phe Lys Thr Leu Ile Ala Leu Lys Thr Arg Asn Ala Ile Ile Ile
        130                 135                 140

Ser Pro His Pro Arg Ala Lys Asn Ser Thr Ile Glu Ala Ala Lys Ile
145                 150                 155                 160

Val Leu Glu Ala Ala Val Lys Ala Gly Ala Pro Glu Gly Ile Ile Gly
                165                 170                 175

Trp Ile Asp Val Pro Ser Leu Glu Leu Thr Asn Leu Val Met Arg Glu
            180                 185                 190
```

```
Ala Asp Val Ile Leu Ala Thr Gly Gly Pro Gly Leu Lys Ala Ala
        195                 200                 205

Tyr Ser Ser Gly Lys Pro Ala Ile Gly Val Gly Ala Gly Asn Thr Pro
        210                 215                 220

Ala Ile Ile Asp Asp Ser Ala Asp Ile Val Leu Ala Val Asn Ser Ile
225                 230                 235                 240

Ile His Ser Lys Thr Phe Asp Asn Gly Met Ile Cys Ala Ser Glu Gln
                245                 250                 255

Ser Val Ile Val Leu Asp Gly Val Tyr Lys Glu Val Lys Lys Glu Phe
                260                 265                 270

Glu Lys Arg Gly Cys Tyr Phe Leu Asn Glu Asp Glu Thr Glu Lys Val
        275                 280                 285

Arg Lys Thr Ile Ile Ile Asn Gly Ala Leu Asn Ala Lys Ile Val Gly
        290                 295                 300

Gln Lys Ala His Thr Ile Ala Asn Leu Ala Gly Phe Glu Val Pro Glu
305                 310                 315                 320

Thr Thr Lys Ile Leu Ile Gly Glu Val Thr Ser Val Asp Ile Ser Glu
                325                 330                 335

Glu Phe Ala His Glu Lys Leu Cys Pro Val Leu Ala Met Tyr Arg Ala
                340                 345                 350

Lys Asp Phe Asp Asp Ala Leu Asp Lys Ala Glu Arg Leu Val Ala Asp
        355                 360                 365

Gly Gly Phe Gly His Thr Ser Ser Leu Tyr Ile Asp Thr Val Thr Gln
        370                 375                 380

Lys Glu Lys Leu Gln Lys Phe Ser Glu Arg Met Lys Thr Cys Arg Ile
385                 390                 395                 400

Leu Val Asn Thr Pro Ser Ser Gln Gly Gly Ile Gly Asp Leu Tyr Asn
                405                 410                 415

Phe Lys Leu Ala Pro Ser Leu Thr Leu Gly Cys Gly Ser Trp Gly Gly
                420                 425                 430

Asn Ser Val Ser Asp Asn Val Gly Val Lys His Leu Leu Asn Ile Lys
        435                 440                 445

Thr Val Ala Glu Arg Arg Glu Asn Met Leu Trp Phe Arg Thr Pro Glu
        450                 455                 460

Lys Ile Tyr Ile Lys Arg Gly Cys Leu Pro Val Ala Leu Asp Glu Leu
465                 470                 475                 480

Lys Asn Val Met Gly Lys Lys Ala Phe Ile Val Thr Asp Asn Phe
                485                 490                 495

Leu Tyr Asn Asn Gly Tyr Thr Lys Pro Ile Thr Asp Lys Leu Asp Glu
                500                 505                 510

Met Gly Ile Val His Lys Thr Phe Phe Asp Val Ser Pro Asp Pro Ser
        515                 520                 525

Leu Ala Ser Ala Lys Ala Gly Ala Ala Glu Met Leu Ala Phe Gln Pro
        530                 535                 540

Asp Thr Ile Ile Ala Val Gly Gly Gly Ser Ala Met Asp Ala Ala Lys
545                 550                 555                 560

Ile Met Trp Val Met Tyr Glu His Pro Glu Val Asp Phe Met Asp Met
                565                 570                 575

Ala Met Arg Phe Met Asp Ile Arg Lys Arg Val Tyr Thr Phe Pro Lys
        580                 585                 590

Met Gly Gln Lys Ala Tyr Phe Ile Ala Ile Pro Thr Ser Ala Gly Thr
        595                 600                 605
```

Gly Ser Glu Val Thr Pro Phe Ala Val Ile Thr Asp Glu Lys Thr Gly
610             615                 620

Ile Lys Tyr Pro Leu Ala Asp Tyr Glu Leu Leu Pro Asp Met Ala Ile
625             630                 635                 640

Val Asp Ala Asp Met Met Met Asn Ala Pro Lys Gly Leu Thr Ala Ala
                645                 650                 655

Ser Gly Ile Asp Ala Leu Thr His Ala Leu Glu Ala Tyr Val Ser Met
            660                 665                 670

Leu Ala Thr Asp Tyr Thr Asp Ser Leu Ala Leu Arg Ala Ile Lys Met
            675                 680                 685

Ile Phe Glu Tyr Leu Pro Arg Ala Tyr Glu Asn Gly Ala Ser Asp Pro
690             695                 700

Val Ala Arg Glu Lys Met Ala Asn Ala Ala Thr Ile Ala Gly Met Ala
705             710                 715                 720

Phe Ala Asn Ala Phe Leu Gly Val Cys His Ser Met Ala His Lys Leu
                725                 730                 735

Gly Ala Phe Tyr His Leu Pro His Gly Val Ala Asn Ala Leu Met Ile
            740                 745                 750

Asn Glu Val Ile Arg Phe Asn Ser Ser Glu Ala Pro Thr Lys Met Gly
            755                 760                 765

Thr Phe Pro Gln Tyr Asp His Pro Arg Thr Leu Glu Arg Tyr Ala Glu
770             775                 780

Ile Ala Asp Tyr Ile Gly Leu Lys Gly Lys Asn Asn Glu Glu Lys Val
785             790                 795                 800

Glu Asn Leu Ile Lys Ala Ile Asp Glu Leu Lys Glu Lys Val Gly Ile
                805                 810                 815

Arg Lys Thr Ile Lys Asp Tyr Asp Ile Asp Glu Lys Glu Phe Leu Asp
            820                 825                 830

Arg Leu Asp Glu Met Val Glu Gln Ala Phe Asp Asp Gln Cys Thr Gly
            835                 840                 845

Thr Asn Pro Arg Tyr Pro Leu Met Asn Glu Ile Arg Gln Met Tyr Leu
        850                 855                 860

Asn Ala Tyr Tyr Gly Gly Ala Lys Lys
865                 870

<210> SEQ ID NO 16
<211> LENGTH: 891
<212> TYPE: PRT
<213> ORGANISM: Artificial sequence
<220> FEATURE:
<223> OTHER INFORMATION: mutant of Escherichia coli aldehyde-alcohol
      dehydrogenase

<400> SEQUENCE: 16

Met Ala Val Thr Asn Val Ala Glu Leu Asn Ala Leu Val Glu Arg Val
1               5                   10                  15

Lys Lys Ala Gln Arg Glu Tyr Ala Ser Phe Thr Gln Glu Gln Val Asp
            20                  25                  30

Lys Ile Phe Arg Ala Ala Ala Leu Ala Ala Asp Ala Arg Ile Pro
        35                  40                  45

Leu Ala Lys Met Ala Val Ala Glu Ser Gly Met Gly Ile Val Glu Asp
50              55                  60

Lys Val Ile Lys Asn His Phe Ala Ser Glu Tyr Ile Tyr Asn Ala Tyr
65              70                  75                  80

Lys Asp Glu Lys Thr Cys Gly Val Leu Ser Glu Asp Asp Thr Phe Gly
                85                  90                  95

-continued

Thr Ile Thr Ile Ala Glu Pro Ile Gly Ile Cys Gly Ile Val Pro
             100                 105                 110

Thr Thr Asn Pro Thr Ser Thr Ala Ile Phe Lys Ser Leu Ile Ser Leu
             115                 120                 125

Lys Thr Arg Asn Ala Ile Ile Phe Ser Pro His Pro Arg Ala Lys Asp
             130                 135                 140

Ala Thr Asn Lys Ala Ala Asp Ile Val Leu Gln Ala Ala Ile Ala Ala
145                 150                 155                 160

Gly Ala Pro Lys Asp Leu Ile Gly Trp Ile Asp Gln Pro Ser Val Glu
             165                 170                 175

Leu Ser Asn Ala Leu Met His His Pro Asp Ile Asn Leu Ile Leu Ala
             180                 185                 190

Thr Gly Gly Pro Gly Met Val Lys Ala Ala Tyr Ser Ser Gly Lys Pro
             195                 200                 205

Ala Ile Gly Val Gly Ala Gly Asn Thr Pro Val Val Ile Asp Glu Thr
             210                 215                 220

Ala Asp Ile Lys Arg Ala Val Ala Ser Val Leu Met Ser Lys Thr Phe
225                 230                 235                 240

Asp Asn Gly Val Ile Cys Ala Ser Glu Gln Ser Val Val Val Asp
             245                 250                 255

Ser Val Tyr Asp Ala Val Arg Glu Arg Phe Ala Thr His Gly Gly Tyr
             260                 265                 270

Leu Leu Gln Gly Lys Glu Leu Lys Ala Val Gln Asp Val Ile Leu Lys
             275                 280                 285

Asn Gly Ala Leu Asn Ala Ala Ile Val Gly Gln Pro Ala Tyr Lys Ile
             290                 295                 300

Ala Glu Leu Ala Gly Phe Ser Val Pro Glu Asn Thr Lys Ile Leu Ile
305                 310                 315                 320

Gly Glu Val Thr Val Val Asp Glu Ser Glu Pro Phe Ala His Glu Lys
             325                 330                 335

Leu Ser Pro Thr Leu Ala Met Tyr Arg Ala Lys Asp Phe Glu Asp Ala
             340                 345                 350

Val Glu Lys Ala Glu Lys Leu Val Ala Met Gly Gly Ile Gly His Thr
             355                 360                 365

Ser Cys Leu Tyr Thr Asp Gln Asp Asn Gln Pro Ala Arg Val Ser Tyr
             370                 375                 380

Phe Gly Gln Lys Met Lys Thr Ala Arg Ile Leu Ile Asn Thr Pro Ala
385                 390                 395                 400

Ser Gln Gly Gly Ile Gly Asp Leu Tyr Asn Phe Lys Leu Ala Pro Ser
             405                 410                 415

Leu Thr Leu Gly Cys Gly Ser Trp Gly Gly Asn Ser Ile Ser Glu Asn
             420                 425                 430

Val Gly Pro Lys His Leu Ile Asn Lys Lys Thr Val Ala Lys Arg Ala
             435                 440                 445

Glu Asn Met Leu Trp His Lys Leu Pro Lys Ser Ile Tyr Phe Arg Arg
             450                 455                 460

Gly Ser Leu Pro Ile Ala Leu Asp Glu Val Ile Thr Asp Gly His Lys
465                 470                 475                 480

Arg Ala Leu Ile Val Thr Asp Arg Phe Leu Phe Asn Asn Gly Tyr Ala
             485                 490                 495

Asp Gln Ile Thr Ser Val Leu Lys Ala Ala Gly Val Glu Thr Glu Val
             500                 505                 510

```
Phe Phe Glu Val Glu Ala Asp Pro Thr Leu Ser Ile Val Arg Lys Gly
            515                 520                 525

Ala Glu Leu Ala Asn Ser Phe Lys Pro Asp Val Ile Ala Leu Gly
530                 535                 540

Gly Gly Ser Pro Met Asp Ala Ala Lys Ile Met Trp Val Met Tyr Glu
545                 550                 555                 560

His Pro Glu Thr His Phe Glu Lys Leu Ala Leu Arg Phe Met Asp Ile
                565                 570                 575

Arg Lys Arg Ile Tyr Lys Phe Pro Lys Met Gly Val Lys Ala Lys Met
            580                 585                 590

Ile Ala Val Thr Thr Thr Ser Gly Thr Gly Ser Glu Val Thr Pro Phe
            595                 600                 605

Ala Val Val Thr Asp Asp Ala Thr Gly Gln Lys Tyr Pro Leu Ala Asp
            610                 615                 620

Tyr Ala Leu Thr Pro Asp Met Ala Ile Val Asp Ala Asn Leu Val Met
625                 630                 635                 640

Asp Met Pro Lys Ser Leu Cys Ala Phe Gly Gly Leu Asp Ala Val Thr
                645                 650                 655

His Ala Met Glu Ala Tyr Val Ser Val Leu Ala Ser Glu Phe Ser Asp
            660                 665                 670

Gly Gln Ala Leu Gln Ala Leu Lys Leu Leu Lys Glu Tyr Leu Pro Ala
            675                 680                 685

Ser Tyr His Glu Gly Ser Lys Asn Pro Val Ala Arg Glu Arg Val His
            690                 695                 700

Ser Ala Ala Thr Ile Ala Gly Ile Ala Phe Ala Asn Ala Phe Leu Gly
705                 710                 715                 720

Val Cys His Ser Met Ala His Lys Leu Gly Ser Gln Phe His Ile Pro
                725                 730                 735

His Gly Leu Ala Asn Ala Leu Leu Ile Cys Asn Val Ile Arg Tyr Asn
            740                 745                 750

Ala Asn Asp Asn Pro Thr Lys Gln Thr Ala Phe Ser Gln Tyr Asp Arg
            755                 760                 765

Pro Gln Ala Arg Arg Arg Tyr Ala Glu Ile Ala Asp His Leu Gly Leu
            770                 775                 780

Ser Ala Pro Gly Asp Arg Thr Ala Ala Lys Ile Glu Lys Leu Leu Ala
785                 790                 795                 800

Trp Leu Glu Thr Leu Lys Ala Glu Leu Gly Ile Pro Lys Ser Ile Arg
                805                 810                 815

Glu Ala Gly Val Gln Glu Ala Asp Phe Leu Ala Asn Val Asp Lys Leu
            820                 825                 830

Ser Glu Asp Ala Phe Asp Asp Gln Cys Thr Gly Ala Asn Pro Arg Tyr
            835                 840                 845

Pro Leu Ile Ser Glu Leu Lys Gln Ile Leu Leu Asp Thr Tyr Tyr Gly
            850                 855                 860

Arg Asp Tyr Val Glu Gly Glu Thr Ala Ala Lys Lys Glu Ala Ala Pro
865                 870                 875                 880

Ala Lys Ala Glu Lys Lys Ala Lys Lys Ser Ala
                885                 890

<210> SEQ ID NO 17
<211> LENGTH: 891
<212> TYPE: PRT
<213> ORGANISM: Artificial sequence
<220> FEATURE:
<223> OTHER INFORMATION: mutant of Escherichia coli aldehyde-alcohol
``` dehydrogenase

<400> SEQUENCE: 17

```
Met Ala Val Thr Asn Val Ala Glu Leu Asn Ala Leu Val Glu Arg Val
1               5                   10                  15

Lys Lys Ala Gln Arg Glu Tyr Ala Ser Phe Thr Gln Glu Gln Val Asp
            20                  25                  30

Lys Ile Phe Arg Ala Ala Leu Ala Ala Ala Asp Ala Arg Ile Pro
        35                  40                  45

Leu Ala Lys Met Ala Val Ala Glu Ser Gly Met Gly Ile Val Glu Asp
    50                  55                  60

Lys Val Ile Lys Asn His Phe Ala Ser Glu Tyr Ile Tyr Asn Ala Tyr
65                  70                  75                  80

Lys Asp Glu Lys Thr Cys Gly Val Leu Ser Glu Asp Thr Phe Gly
                85                  90                  95

Thr Ile Thr Ile Ala Glu Pro Ile Gly Ile Ile Cys Gly Ile Val Pro
            100                 105                 110

Thr Thr Asn Pro Thr Ser Thr Ala Ile Phe Lys Ser Leu Ile Ser Leu
            115                 120                 125

Lys Thr Arg Asn Ala Ile Ile Phe Ser Pro His Pro Arg Ala Lys Asp
130                 135                 140

Ala Thr Asn Lys Ala Ala Asp Ile Val Leu Gln Ala Ala Ile Ala Ala
145                 150                 155                 160

Gly Ala Pro Lys Asp Leu Ile Gly Trp Ile Asp Gln Pro Ser Val Glu
                165                 170                 175

Leu Ser Asn Ala Leu Met His His Pro Asp Ile Asn Leu Ile Leu Ala
            180                 185                 190

Thr Gly Gly Pro Gly Met Val Lys Ala Ala Tyr Ser Ser Gly Lys Pro
        195                 200                 205

Ala Ile Gly Val Gly Ala Gly Asn Thr Pro Val Val Ile Asp Glu Thr
    210                 215                 220

Ala Asp Ile Lys Arg Ala Val Ala Ser Val Leu Met Ser Lys Thr Phe
225                 230                 235                 240

Asp Asn Gly Val Ile Cys Ala Ser Glu Gln Ser Val Val Val Asp
                245                 250                 255

Ser Val Tyr Asp Ala Val Arg Glu Arg Phe Ala Thr His Gly Gly Tyr
            260                 265                 270

Leu Leu Gln Gly Lys Glu Leu Lys Ala Val Gln Asp Val Ile Leu Lys
        275                 280                 285

Asn Gly Ala Leu Asn Ala Ala Ile Val Gly Gln Pro Ala Tyr Lys Ile
    290                 295                 300

Ala Glu Leu Ala Gly Phe Ser Val Pro Glu Asn Thr Lys Ile Leu Ile
305                 310                 315                 320

Gly Glu Val Thr Val Val Asp Glu Ser Glu Pro Phe Ala His Glu Lys
                325                 330                 335

Leu Ser Pro Thr Leu Ala Met Tyr Arg Ala Lys Asp Phe Glu Asp Ala
            340                 345                 350

Val Glu Lys Ala Glu Lys Leu Val Ala Met Gly Gly Ile Gly His Thr
        355                 360                 365

Ser Cys Leu Tyr Thr Asp Gln Asp Asn Gln Pro Ala Arg Val Ser Tyr
    370                 375                 380

Phe Gly Gln Lys Met Lys Thr Ala Arg Ile Leu Ile Asn Thr Pro Ala
385                 390                 395                 400
```

-continued

Ser Gln Gly Gly Ile Gly Asp Leu Tyr Asn Phe Lys Leu Ala Pro Ser
            405                 410                 415

Leu Thr Leu Gly Cys Gly Ser Trp Gly Gly Asn Ser Ile Ser Glu Asn
        420                 425                 430

Val Gly Pro Lys His Leu Ile Asn Lys Lys Thr Val Ala Lys Arg Ala
        435                 440                 445

Glu Asn Met Leu Trp His Lys Leu Pro Lys Ser Ile Tyr Phe Arg Arg
450                 455                 460

Gly Ser Leu Pro Ile Ala Leu Asp Glu Val Ile Thr Asp Gly His Lys
465                 470                 475                 480

Arg Ala Leu Ile Val Thr Asp Arg Phe Leu Phe Asn Asn Gly Tyr Ala
                485                 490                 495

Asp Gln Ile Thr Ser Val Leu Lys Ala Ala Gly Val Glu Thr Glu Val
            500                 505                 510

Phe Phe Glu Val Glu Ala Asp Pro Thr Leu Ser Ile Val Arg Lys Gly
        515                 520                 525

Ala Glu Leu Ala Asn Ser Phe Lys Pro Asp Val Ile Ile Ala Leu Gly
        530                 535                 540

Gly Gly Ser Pro Met Asp Ala Ala Lys Ile Met Trp Val Met Tyr Glu
545                 550                 555                 560

His Pro Glu Thr His Phe Glu Ala Leu Ala Leu Arg Phe Met Asp Ile
                565                 570                 575

Arg Lys Arg Ile Tyr Lys Phe Pro Lys Met Gly Val Lys Ala Lys Met
                580                 585                 590

Ile Ala Val Thr Thr Thr Ser Gly Thr Gly Ser Glu Val Thr Pro Phe
        595                 600                 605

Ala Val Val Thr Asp Asp Ala Thr Gly Gln Lys Tyr Pro Leu Ala Asp
        610                 615                 620

Tyr Ala Leu Thr Pro Asp Met Ala Ile Val Asp Ala Asn Leu Val Met
625                 630                 635                 640

Asp Met Pro Lys Ser Leu Cys Ala Phe Gly Gly Leu Asp Ala Val Thr
                645                 650                 655

His Ala Met Glu Ala Tyr Val Ser Val Leu Ala Ser Glu Phe Ser Asp
                660                 665                 670

Gly Gln Ala Leu Gln Ala Leu Lys Leu Leu Lys Glu Tyr Leu Pro Ala
            675                 680                 685

Ser Tyr His Glu Gly Ser Lys Asn Pro Val Ala Arg Glu Arg Val His
        690                 695                 700

Ser Ala Ala Thr Ile Ala Gly Ile Ala Phe Ala Asn Ala Phe Leu Gly
705                 710                 715                 720

Val Cys His Ser Met Ala His Lys Leu Gly Ser Gln Phe His Ile Pro
                725                 730                 735

His Gly Leu Ala Asn Ala Leu Leu Ile Cys Asn Val Ile Arg Tyr Asn
            740                 745                 750

Ala Asn Asp Asn Pro Thr Lys Gln Thr Ala Phe Ser Gln Tyr Asp Arg
        755                 760                 765

Pro Gln Ala Arg Arg Arg Tyr Ala Glu Ile Ala Asp His Leu Gly Leu
        770                 775                 780

Ser Ala Pro Gly Asp Arg Thr Ala Ala Lys Ile Glu Lys Leu Leu Ala
785                 790                 795                 800

Trp Leu Glu Thr Leu Lys Ala Glu Leu Gly Ile Pro Lys Ser Ile Arg
                805                 810                 815

Glu Ala Gly Val Gln Glu Ala Asp Phe Leu Ala Asn Val Asp Lys Leu

```
                    820                 825                 830
Ser Glu Asp Ala Phe Asp Gln Cys Thr Gly Ala Asn Pro Arg Tyr
                835                 840                 845

Pro Leu Ile Ser Glu Leu Lys Gln Ile Leu Leu Asp Thr Tyr Tyr Gly
            850                 855                 860

Arg Asp Tyr Val Glu Gly Glu Thr Ala Ala Lys Glu Ala Ala Pro
865                 870                 875                 880

Ala Lys Ala Glu Lys Lys Ala Lys Lys Ser Ala
                885                 890
```

<210> SEQ ID NO 18
<211> LENGTH: 891
<212> TYPE: PRT
<213> ORGANISM: Artificial sequence
<220> FEATURE:
<223> OTHER INFORMATION: mutant of Escherichia coli aldehyde-alcohol dehydrogenase

<400> SEQUENCE: 18

```
Met Ala Val Thr Asn Val Ala Glu Leu Asn Ala Leu Val Glu Arg Val
1               5                   10                  15

Lys Lys Ala Gln Arg Glu Tyr Ala Ser Phe Thr Gln Glu Gln Val Asp
            20                  25                  30

Lys Ile Phe Arg Ala Ala Ala Leu Ala Ala Ala Asp Ala Arg Ile Pro
        35                  40                  45

Leu Ala Lys Met Ala Val Ala Glu Ser Gly Met Gly Ile Val Glu Asp
    50                  55                  60

Lys Val Ile Lys Asn His Phe Ala Ser Glu Tyr Ile Tyr Asn Ala Tyr
65                  70                  75                  80

Lys Asp Glu Lys Thr Cys Gly Val Leu Ser Glu Asp Asp Thr Phe Gly
                85                  90                  95

Thr Ile Thr Ile Ala Glu Pro Ile Gly Ile Ile Cys Gly Ile Val Pro
            100                 105                 110

Thr Thr Asn Pro Thr Ser Thr Ala Ile Phe Lys Ser Leu Ile Ser Leu
        115                 120                 125

Lys Thr Arg Asn Ala Ile Ile Phe Ser Pro His Pro Arg Ala Lys Asp
    130                 135                 140

Ala Thr Asn Lys Ala Ala Asp Ile Val Leu Gln Ala Ala Ile Ala Ala
145                 150                 155                 160

Gly Ala Pro Lys Asp Leu Ile Gly Trp Ile Asp Gln Pro Ser Val Glu
                165                 170                 175

Leu Ser Asn Ala Leu Met His His Pro Asp Ile Asn Leu Ile Leu Ala
            180                 185                 190

Thr Gly Gly Pro Gly Met Val Lys Ala Ala Tyr Ser Ser Gly Lys Pro
        195                 200                 205

Ala Ile Gly Val Gly Ala Gly Asn Thr Pro Val Val Ile Asp Glu Thr
    210                 215                 220

Ala Asp Ile Lys Arg Ala Val Ala Ser Val Leu Met Ser Lys Thr Phe
225                 230                 235                 240

Asp Asn Gly Val Ile Cys Ala Ser Glu Gln Ser Val Val Val Val Asp
                245                 250                 255

Ser Val Tyr Asp Ala Val Arg Glu Arg Phe Ala Thr His Gly Gly Tyr
            260                 265                 270

Leu Leu Gln Gly Lys Glu Leu Lys Ala Val Gln Asp Val Ile Leu Lys
        275                 280                 285
```

-continued

Asn Gly Ala Leu Asn Ala Ala Ile Val Gly Gln Pro Ala Tyr Lys Ile
290                 295                 300

Ala Glu Leu Ala Gly Phe Ser Val Pro Glu Asn Thr Lys Ile Leu Ile
305                 310                 315                 320

Gly Glu Val Thr Val Asp Glu Ser Glu Pro Phe Ala His Glu Lys
            325                 330                 335

Leu Ser Pro Thr Leu Ala Met Tyr Arg Ala Lys Asp Phe Glu Asp Ala
            340                 345                 350

Val Glu Lys Ala Glu Lys Leu Ala Met Gly Gly Ile Gly His Thr
            355                 360                 365

Ser Cys Leu Tyr Thr Asp Gln Asp Asn Gln Pro Ala Arg Val Ser Tyr
370                 375                 380

Phe Gly Gln Lys Met Lys Thr Ala Arg Ile Leu Ile Asn Thr Pro Ala
385                 390                 395                 400

Ser Gln Gly Gly Ile Gly Asp Leu Tyr Asn Phe Lys Leu Ala Pro Ser
                405                 410                 415

Leu Thr Leu Gly Cys Gly Ser Trp Gly Gly Asn Ser Ile Ser Glu Asn
            420                 425                 430

Val Gly Pro Lys His Leu Ile Asn Lys Lys Thr Val Ala Lys Arg Ala
            435                 440                 445

Glu Asn Met Leu Trp His Lys Leu Pro Lys Ser Ile Tyr Phe Arg Arg
450                 455                 460

Gly Ser Leu Pro Ile Ala Leu Asp Glu Val Ile Thr Asp Gly His Lys
465                 470                 475                 480

Arg Ala Leu Ile Val Thr Asp Arg Phe Leu Phe Asn Asn Gly Tyr Ala
                485                 490                 495

Asp Gln Ile Thr Ser Val Leu Lys Ala Ala Gly Val Glu Thr Glu Val
            500                 505                 510

Phe Phe Glu Val Glu Ala Asp Pro Thr Leu Ser Ile Val Arg Lys Gly
            515                 520                 525

Ala Glu Leu Ala Asn Ser Phe Lys Pro Asp Val Ile Ile Ala Leu Gly
            530                 535                 540

Gly Gly Ser Pro Met Asp Ala Ala Lys Ile Met Trp Val Met Tyr Glu
545                 550                 555                 560

His Pro Glu Thr His Phe Glu Leu Leu Ala Leu Arg Phe Met Asp Ile
                565                 570                 575

Arg Lys Arg Ile Tyr Lys Phe Pro Lys Met Gly Val Lys Ala Lys Met
            580                 585                 590

Ile Ala Val Thr Thr Ser Gly Thr Gly Ser Glu Val Thr Pro Phe
            595                 600                 605

Ala Val Val Thr Asp Asp Ala Thr Gly Gln Lys Tyr Pro Leu Ala Asp
610                 615                 620

Tyr Ala Leu Thr Pro Asp Met Ala Ile Val Asp Ala Asn Leu Val Met
625                 630                 635                 640

Asp Met Pro Lys Ser Leu Cys Ala Phe Gly Gly Leu Asp Ala Val Thr
                645                 650                 655

His Ala Met Glu Ala Tyr Val Ser Val Leu Ala Ser Glu Phe Ser Asp
            660                 665                 670

Gly Gln Ala Leu Gln Ala Leu Lys Leu Leu Lys Glu Tyr Leu Pro Ala
            675                 680                 685

Ser Tyr His Glu Gly Ser Lys Asn Pro Val Ala Arg Glu Arg Val His
690                 695                 700

Ser Ala Ala Thr Ile Ala Gly Ile Ala Phe Ala Asn Ala Phe Leu Gly

```
                705                 710                 715                 720
Val Cys His Ser Met Ala His Lys Leu Gly Ser Gln Phe His Ile Pro
                    725                 730                 735

His Gly Leu Ala Asn Ala Leu Leu Ile Cys Asn Val Ile Arg Tyr Asn
                740                 745                 750

Ala Asn Asp Asn Pro Thr Lys Gln Thr Ala Phe Ser Gln Tyr Asp Arg
                755                 760                 765

Pro Gln Ala Arg Arg Tyr Ala Glu Ile Ala Asp His Leu Gly Leu
            770                 775                 780

Ser Ala Pro Gly Asp Arg Thr Ala Ala Lys Ile Glu Lys Leu Leu Ala
785                 790                 795                 800

Trp Leu Glu Thr Leu Lys Ala Glu Leu Gly Ile Pro Lys Ser Ile Arg
                805                 810                 815

Glu Ala Gly Val Gln Glu Ala Asp Phe Leu Ala Asn Val Asp Lys Leu
                820                 825                 830

Ser Glu Asp Ala Phe Asp Asp Gln Cys Thr Gly Ala Asn Pro Arg Tyr
                835                 840                 845

Pro Leu Ile Ser Glu Leu Lys Gln Ile Leu Leu Asp Thr Tyr Tyr Gly
            850                 855                 860

Arg Asp Tyr Val Glu Gly Glu Thr Ala Ala Lys Lys Glu Ala Ala Pro
865                 870                 875                 880

Ala Lys Ala Glu Lys Lys Ala Lys Lys Ser Ala
                885                 890

<210> SEQ ID NO 19
<211> LENGTH: 891
<212> TYPE: PRT
<213> ORGANISM: Artificial sequence
<220> FEATURE:
<223> OTHER INFORMATION: mutant of Escherichia coli aldehyde-alcohol
      dehydrogenase

<400> SEQUENCE: 19

Met Ala Val Thr Asn Val Ala Glu Leu Asn Ala Leu Val Glu Arg Val
1               5                   10                  15

Lys Lys Ala Gln Arg Glu Tyr Ala Ser Phe Thr Gln Glu Gln Val Asp
                20                  25                  30

Lys Ile Phe Arg Ala Ala Ala Leu Ala Ala Ala Asp Ala Arg Ile Pro
            35                  40                  45

Leu Ala Lys Met Ala Val Ala Glu Ser Gly Met Gly Ile Val Glu Asp
        50                  55                  60

Lys Val Ile Lys Asn His Phe Ala Ser Glu Tyr Ile Tyr Asn Ala Tyr
65                  70                  75                  80

Lys Asp Glu Lys Thr Cys Gly Val Leu Ser Glu Asp Asp Thr Phe Gly
                85                  90                  95

Thr Ile Thr Ile Ala Glu Pro Ile Gly Ile Ile Cys Gly Ile Val Pro
            100                 105                 110

Thr Thr Asn Pro Thr Ser Thr Ala Ile Phe Lys Ser Leu Ile Ser Leu
        115                 120                 125

Lys Thr Arg Asn Ala Ile Ile Phe Ser Pro His Pro Arg Ala Lys Asp
    130                 135                 140

Ala Thr Asn Lys Ala Ala Asp Ile Val Leu Gln Ala Ala Ile Ala Ala
145                 150                 155                 160

Gly Ala Pro Lys Asp Leu Ile Gly Trp Ile Asp Gln Pro Ser Val Glu
                165                 170                 175
```

-continued

Leu Ser Asn Ala Leu Met His His Pro Asp Ile Asn Leu Ile Leu Ala
            180                 185                 190
Thr Gly Gly Pro Gly Met Val Lys Ala Ala Tyr Ser Ser Gly Lys Pro
        195                 200                 205
Ala Ile Gly Val Gly Ala Gly Asn Thr Pro Val Val Ile Asp Glu Thr
    210                 215                 220
Ala Asp Ile Lys Arg Ala Val Ala Ser Val Leu Met Ser Lys Thr Phe
225                 230                 235                 240
Asp Asn Gly Val Ile Cys Ala Ser Glu Gln Ser Val Val Val Val Asp
                245                 250                 255
Ser Val Tyr Asp Ala Val Arg Glu Arg Phe Ala Thr His Gly Gly Tyr
            260                 265                 270
Leu Leu Gln Gly Lys Glu Leu Lys Ala Val Gln Asp Val Ile Leu Lys
        275                 280                 285
Asn Gly Ala Leu Asn Ala Ala Ile Val Gly Gln Pro Ala Tyr Lys Ile
    290                 295                 300
Ala Glu Leu Ala Gly Phe Ser Val Pro Glu Asn Thr Lys Ile Leu Ile
305                 310                 315                 320
Gly Glu Val Thr Val Val Asp Glu Ser Glu Pro Phe Ala His Glu Lys
                325                 330                 335
Leu Ser Pro Thr Leu Ala Met Tyr Arg Ala Lys Asp Phe Glu Asp Ala
            340                 345                 350
Val Glu Lys Ala Glu Lys Leu Val Ala Met Gly Gly Ile Gly His Thr
        355                 360                 365
Ser Cys Leu Tyr Thr Asp Gln Asp Asn Gln Pro Ala Arg Val Ser Tyr
    370                 375                 380
Phe Gly Gln Lys Met Lys Thr Ala Arg Ile Leu Ile Asn Thr Pro Ala
385                 390                 395                 400
Ser Gln Gly Gly Ile Gly Asp Leu Tyr Asn Phe Lys Leu Ala Pro Ser
                405                 410                 415
Leu Thr Leu Gly Cys Gly Ser Trp Gly Gly Asn Ser Ile Ser Glu Asn
            420                 425                 430
Val Gly Pro Lys His Leu Ile Asn Lys Lys Thr Val Ala Lys Arg Ala
        435                 440                 445
Glu Asn Met Leu Trp His Lys Leu Pro Lys Ser Ile Tyr Phe Arg Arg
    450                 455                 460
Gly Ser Leu Pro Ile Ala Leu Asp Glu Val Ile Thr Asp Gly His Lys
465                 470                 475                 480
Arg Ala Leu Ile Val Thr Asp Arg Phe Leu Phe Asn Asn Gly Tyr Ala
                485                 490                 495
Asp Gln Ile Thr Ser Val Leu Lys Ala Ala Gly Val Glu Thr Glu Val
            500                 505                 510
Phe Phe Glu Val Glu Ala Asp Pro Thr Leu Ser Ile Val Arg Lys Gly
        515                 520                 525
Ala Glu Leu Ala Asn Ser Phe Lys Pro Asp Val Ile Ile Ala Leu Gly
    530                 535                 540
Gly Gly Ser Pro Met Asp Ala Ala Lys Ile Met Trp Val Met Tyr Glu
545                 550                 555                 560
His Pro Glu Thr His Phe Glu Asn Leu Ala Leu Arg Phe Met Asp Ile
                565                 570                 575
Arg Lys Arg Ile Tyr Lys Phe Pro Lys Met Gly Val Lys Ala Lys Met
            580                 585                 590
Ile Ala Val Thr Thr Thr Ser Gly Thr Gly Ser Glu Val Thr Pro Phe

```
                595                 600                 605
Ala Val Val Thr Asp Asp Ala Thr Gly Gln Lys Tyr Pro Leu Ala Asp
                610                 615                 620

Tyr Ala Leu Thr Pro Asp Met Ala Ile Val Asp Ala Asn Leu Val Met
625                 630                 635                 640

Asp Met Pro Lys Ser Leu Cys Ala Phe Gly Leu Asp Ala Val Thr
                645                 650                 655

His Ala Met Glu Ala Tyr Val Ser Val Leu Ala Ser Glu Phe Ser Asp
                660                 665                 670

Gly Gln Ala Leu Gln Ala Leu Lys Leu Leu Lys Glu Tyr Leu Pro Ala
                675                 680                 685

Ser Tyr His Glu Gly Ser Lys Asn Pro Val Ala Arg Glu Arg Val His
                690                 695                 700

Ser Ala Ala Thr Ile Ala Gly Ile Ala Phe Ala Asn Ala Phe Leu Gly
705                 710                 715                 720

Val Cys His Ser Met Ala His Lys Leu Gly Ser Gln Phe His Ile Pro
                725                 730                 735

His Gly Leu Ala Asn Ala Leu Leu Ile Cys Asn Val Ile Arg Tyr Asn
                740                 745                 750

Ala Asn Asp Asn Pro Thr Lys Gln Thr Ala Phe Ser Gln Tyr Asp Arg
                755                 760                 765

Pro Gln Ala Arg Arg Arg Tyr Ala Glu Ile Ala Asp His Leu Gly Leu
                770                 775                 780

Ser Ala Pro Gly Asp Arg Thr Ala Ala Lys Ile Glu Lys Leu Leu Ala
785                 790                 795                 800

Trp Leu Glu Thr Leu Lys Ala Glu Leu Gly Ile Pro Lys Ser Ile Arg
                805                 810                 815

Glu Ala Gly Val Gln Glu Ala Asp Phe Leu Ala Asn Val Asp Lys Leu
                820                 825                 830

Ser Glu Asp Ala Phe Asp Asp Gln Cys Thr Gly Ala Asn Pro Arg Tyr
                835                 840                 845

Pro Leu Ile Ser Glu Leu Lys Gln Ile Leu Leu Asp Thr Tyr Tyr Gly
                850                 855                 860

Arg Asp Tyr Val Glu Gly Glu Thr Ala Ala Lys Lys Glu Ala Ala Pro
865                 870                 875                 880

Ala Lys Ala Glu Lys Lys Ala Lys Lys Ser Ala
                885                 890

<210> SEQ ID NO 20
<211> LENGTH: 891
<212> TYPE: PRT
<213> ORGANISM: Artificial sequence
<220> FEATURE:
<223> OTHER INFORMATION: mutant of Escherichia coli aldehyde-alcohol
      dehydrogenase

<400> SEQUENCE: 20

Met Ala Val Thr Asn Val Ala Glu Leu Asn Ala Leu Val Glu Arg Val
1               5                   10                  15

Lys Lys Ala Gln Arg Glu Tyr Ala Ser Phe Thr Gln Glu Gln Val Asp
                20                  25                  30

Lys Ile Phe Arg Ala Ala Ala Leu Ala Ala Ala Asp Ala Arg Ile Pro
                35                  40                  45

Leu Ala Lys Met Ala Val Ala Glu Ser Gly Met Gly Ile Val Glu Asp
                50                  55                  60
```

```
Lys Val Ile Lys Asn His Phe Ala Ser Glu Tyr Ile Tyr Asn Ala Tyr
 65                  70                  75                  80

Lys Asp Glu Lys Thr Cys Gly Val Leu Ser Glu Asp Thr Phe Gly
             85                  90                  95

Thr Ile Thr Ile Ala Glu Pro Ile Gly Ile Ile Cys Gly Ile Val Pro
             100                 105                 110

Thr Thr Asn Pro Thr Ser Thr Ala Ile Phe Lys Ser Leu Ile Ser Leu
             115                 120                 125

Lys Thr Arg Asn Ala Ile Ile Phe Ser Pro His Pro Arg Ala Lys Asp
         130                 135                 140

Ala Thr Asn Lys Ala Ala Asp Ile Val Leu Gln Ala Ala Ile Ala Ala
145                 150                 155                 160

Gly Ala Pro Lys Asp Leu Ile Gly Trp Ile Asp Gln Pro Ser Val Glu
             165                 170                 175

Leu Ser Asn Ala Leu Met His His Pro Asp Ile Asn Leu Ile Leu Ala
             180                 185                 190

Thr Gly Gly Pro Gly Met Val Lys Ala Ala Tyr Ser Ser Gly Lys Pro
         195                 200                 205

Ala Ile Gly Val Gly Ala Gly Asn Thr Pro Val Val Ile Asp Glu Thr
         210                 215                 220

Ala Asp Ile Lys Arg Ala Val Ala Ser Val Leu Met Ser Lys Thr Phe
225                 230                 235                 240

Asp Asn Gly Val Ile Cys Ala Ser Glu Gln Ser Val Val Val Asp
             245                 250                 255

Ser Val Tyr Asp Ala Val Arg Glu Arg Phe Ala Thr His Gly Gly Tyr
             260                 265                 270

Leu Leu Gln Gly Lys Glu Leu Lys Ala Val Gln Asp Val Ile Leu Lys
         275                 280                 285

Asn Gly Ala Leu Asn Ala Ala Ile Val Gly Gln Pro Ala Tyr Lys Ile
         290                 295                 300

Ala Glu Leu Ala Gly Phe Ser Val Pro Glu Asn Thr Lys Ile Leu Ile
305                 310                 315                 320

Gly Glu Val Thr Val Val Asp Glu Ser Glu Pro Phe Ala His Glu Lys
             325                 330                 335

Leu Ser Pro Thr Leu Ala Met Tyr Arg Ala Lys Asp Phe Glu Asp Ala
             340                 345                 350

Val Glu Lys Ala Glu Lys Leu Val Ala Met Gly Gly Ile Gly His Thr
         355                 360                 365

Ser Cys Leu Tyr Thr Asp Gln Asp Asn Gln Pro Ala Arg Val Ser Tyr
         370                 375                 380

Phe Gly Gln Lys Met Lys Thr Ala Arg Ile Leu Ile Asn Thr Pro Ala
385                 390                 395                 400

Ser Gln Gly Gly Ile Gly Asp Leu Tyr Asn Phe Lys Leu Ala Pro Ser
             405                 410                 415

Leu Thr Leu Gly Cys Gly Ser Trp Gly Gly Asn Ser Ile Ser Glu Asn
             420                 425                 430

Val Gly Pro Lys His Leu Ile Asn Lys Lys Thr Val Ala Lys Arg Ala
         435                 440                 445

Glu Asn Met Leu Trp His Lys Leu Pro Lys Ser Ile Tyr Phe Arg Arg
         450                 455                 460

Gly Ser Leu Pro Ile Ala Leu Asp Glu Val Ile Thr Asp Gly His Lys
465                 470                 475                 480

Arg Ala Leu Ile Val Thr Asp Arg Phe Leu Phe Asn Asn Gly Tyr Ala
```

```
                    485                 490                 495
Asp Gln Ile Thr Ser Val Leu Lys Ala Ala Gly Val Glu Thr Glu Val
                500                 505                 510

Phe Phe Glu Val Glu Ala Asp Pro Thr Leu Ser Ile Val Arg Lys Gly
            515                 520                 525

Ala Glu Leu Ala Asn Ser Phe Lys Pro Asp Val Ile Ile Ala Leu Gly
        530                 535                 540

Gly Gly Ser Pro Met Asp Ala Ala Lys Ile Met Trp Val Met Tyr Glu
545                 550                 555                 560

His Pro Glu Thr His Phe Glu Gly Leu Ala Leu Arg Phe Met Asp Ile
                565                 570                 575

Arg Lys Arg Ile Tyr Lys Phe Pro Lys Met Gly Val Lys Ala Lys Met
            580                 585                 590

Ile Ala Val Thr Thr Thr Ser Gly Thr Gly Ser Glu Val Thr Pro Phe
        595                 600                 605

Ala Val Val Thr Asp Asp Ala Thr Gly Gln Lys Tyr Pro Leu Ala Asp
    610                 615                 620

Tyr Ala Leu Thr Pro Asp Met Ala Ile Val Asp Ala Asn Leu Val Met
625                 630                 635                 640

Asp Met Pro Lys Ser Leu Cys Ala Phe Gly Gly Leu Asp Ala Val Thr
                645                 650                 655

His Ala Met Glu Ala Tyr Val Ser Val Leu Ala Ser Glu Phe Ser Asp
            660                 665                 670

Gly Gln Ala Leu Gln Ala Leu Lys Leu Leu Lys Glu Tyr Leu Pro Ala
        675                 680                 685

Ser Tyr His Glu Gly Ser Lys Asn Pro Val Ala Arg Glu Arg Val His
    690                 695                 700

Ser Ala Ala Thr Ile Ala Gly Ile Ala Phe Ala Asn Ala Phe Leu Gly
705                 710                 715                 720

Val Cys His Ser Met Ala His Lys Leu Gly Ser Gln Phe His Ile Pro
                725                 730                 735

His Gly Leu Ala Asn Ala Leu Leu Ile Cys Asn Val Ile Arg Tyr Asn
            740                 745                 750

Ala Asn Asp Asn Pro Thr Lys Gln Thr Ala Phe Ser Gln Tyr Asp Arg
        755                 760                 765

Pro Gln Ala Arg Arg Arg Tyr Ala Glu Ile Ala Asp His Leu Gly Leu
    770                 775                 780

Ser Ala Pro Gly Asp Arg Thr Ala Ala Lys Ile Glu Lys Leu Leu Ala
785                 790                 795                 800

Trp Leu Glu Thr Leu Lys Ala Glu Leu Gly Ile Pro Lys Ser Ile Arg
                805                 810                 815

Glu Ala Gly Val Gln Glu Ala Asp Phe Leu Ala Asn Val Asp Lys Leu
            820                 825                 830

Ser Glu Asp Ala Phe Asp Asp Gln Cys Thr Gly Ala Asn Pro Arg Tyr
        835                 840                 845

Pro Leu Ile Ser Glu Leu Lys Gln Ile Leu Leu Asp Thr Tyr Tyr Gly
    850                 855                 860

Arg Asp Tyr Val Glu Gly Glu Thr Ala Ala Lys Lys Glu Ala Ala Pro
865                 870                 875                 880

Ala Lys Ala Glu Lys Lys Ala Lys Lys Ser Ala
                885                 890

<210> SEQ ID NO 21
```

<211> LENGTH: 891
<212> TYPE: PRT
<213> ORGANISM: Artificial sequence
<220> FEATURE:
<223> OTHER INFORMATION: mutant of Escherichia coli aldehyde-alcohol
     dehydrogenase

<400> SEQUENCE: 21

Met Ala Val Thr Asn Val Ala Glu Leu Asn Ala Leu Val Glu Arg Val
1               5                   10                  15

Lys Lys Ala Gln Arg Glu Tyr Ala Ser Phe Thr Gln Glu Gln Val Asp
            20                  25                  30

Lys Ile Phe Arg Ala Ala Leu Ala Ala Asp Ala Arg Ile Pro
        35                  40                  45

Leu Ala Lys Met Ala Val Ala Glu Ser Gly Met Gly Ile Val Glu Asp
    50                  55                  60

Lys Val Ile Lys Asn His Phe Ala Ser Glu Tyr Ile Tyr Asn Ala Tyr
65                  70                  75                  80

Lys Asp Glu Lys Thr Cys Gly Val Leu Ser Glu Asp Thr Phe Gly
                85                  90                  95

Thr Ile Thr Ile Ala Glu Pro Ile Gly Ile Ile Cys Gly Ile Val Pro
            100                 105                 110

Thr Thr Asn Pro Thr Ser Thr Ala Ile Phe Lys Ser Leu Ile Ser Leu
        115                 120                 125

Lys Thr Arg Asn Ala Ile Ile Phe Ser Pro His Pro Arg Ala Lys Asp
    130                 135                 140

Ala Thr Asn Lys Ala Ala Asp Ile Val Leu Gln Ala Ala Ile Ala Ala
145                 150                 155                 160

Gly Ala Pro Lys Asp Leu Ile Gly Trp Ile Asp Gln Pro Ser Val Glu
                165                 170                 175

Leu Ser Asn Ala Leu Met His His Pro Asp Ile Asn Leu Ile Leu Ala
            180                 185                 190

Thr Gly Gly Pro Gly Met Val Lys Ala Ala Tyr Ser Ser Gly Lys Pro
        195                 200                 205

Ala Ile Gly Val Gly Ala Gly Asn Thr Pro Val Val Ile Asp Glu Thr
    210                 215                 220

Ala Asp Ile Lys Arg Ala Val Ala Ser Val Leu Met Ser Lys Thr Phe
225                 230                 235                 240

Asp Asn Gly Val Ile Cys Ala Ser Glu Gln Ser Val Val Val Asp
                245                 250                 255

Ser Val Tyr Asp Ala Val Arg Glu Arg Phe Ala Thr His Gly Gly Tyr
            260                 265                 270

Leu Leu Gln Gly Lys Glu Leu Lys Ala Val Gln Asp Val Ile Leu Lys
        275                 280                 285

Asn Gly Ala Leu Asn Ala Ala Ile Val Gly Gln Pro Ala Tyr Lys Ile
    290                 295                 300

Ala Glu Leu Ala Gly Phe Ser Val Pro Glu Asn Thr Lys Ile Leu Ile
305                 310                 315                 320

Gly Glu Val Thr Val Val Asp Glu Ser Glu Pro Phe Ala His Glu Lys
                325                 330                 335

Leu Ser Pro Thr Leu Ala Met Tyr Arg Ala Lys Asp Phe Glu Asp Ala
            340                 345                 350

Val Glu Lys Ala Glu Lys Leu Val Ala Met Gly Gly Ile Gly His Thr
        355                 360                 365

Ser Cys Leu Tyr Thr Asp Gln Asp Asn Gln Pro Ala Arg Val Ser Tyr

```
                370                 375                 380
Phe Gly Gln Lys Met Lys Thr Ala Arg Ile Leu Ile Asn Thr Pro Ala
385                 390                 395                 400

Ser Gln Gly Gly Ile Gly Asp Leu Tyr Asn Phe Lys Leu Ala Pro Ser
            405                 410                 415

Leu Thr Leu Gly Cys Gly Ser Trp Gly Asn Ser Ile Ser Glu Asn
            420                 425                 430

Val Gly Pro Lys His Leu Ile Asn Lys Lys Thr Val Ala Lys Arg Ala
            435                 440                 445

Glu Asn Met Leu Trp His Lys Leu Pro Lys Ser Ile Tyr Phe Arg Arg
            450                 455                 460

Gly Ser Leu Pro Ile Ala Leu Asp Glu Val Ile Thr Asp Gly His Lys
465                 470                 475                 480

Arg Ala Leu Ile Val Thr Asp Arg Phe Leu Phe Asn Asn Gly Tyr Ala
                485                 490                 495

Asp Gln Ile Thr Ser Val Leu Lys Ala Ala Gly Val Glu Thr Glu Val
                500                 505                 510

Phe Phe Glu Val Glu Ala Asp Pro Thr Leu Ser Ile Val Arg Lys Gly
                515                 520                 525

Ala Glu Leu Ala Asn Ser Phe Lys Pro Asp Val Ile Ala Leu Gly
            530                 535                 540

Gly Gly Ser Pro Met Asp Ala Ala Lys Ile Met Trp Val Met Tyr Glu
545                 550                 555                 560

His Pro Glu Thr His Phe Glu Ser Leu Ala Leu Arg Phe Met Asp Ile
                565                 570                 575

Arg Lys Arg Ile Tyr Lys Phe Pro Lys Met Gly Val Lys Ala Lys Met
                580                 585                 590

Ile Ala Val Thr Thr Thr Ser Gly Thr Gly Ser Glu Val Thr Pro Phe
                595                 600                 605

Ala Val Val Thr Asp Asp Ala Thr Gly Gln Lys Tyr Pro Leu Ala Asp
                610                 615                 620

Tyr Ala Leu Thr Pro Asp Met Ala Ile Val Asp Ala Asn Leu Val Met
625                 630                 635                 640

Asp Met Pro Lys Ser Leu Cys Ala Phe Gly Gly Leu Asp Ala Val Thr
                645                 650                 655

His Ala Met Glu Ala Tyr Val Ser Val Leu Ala Ser Glu Phe Ser Asp
                660                 665                 670

Gly Gln Ala Leu Gln Ala Leu Lys Leu Leu Lys Glu Tyr Leu Pro Ala
            675                 680                 685

Ser Tyr His Glu Gly Ser Lys Asn Pro Val Ala Arg Glu Arg Val His
            690                 695                 700

Ser Ala Ala Thr Ile Ala Gly Ile Ala Phe Ala Asn Ala Phe Leu Gly
705                 710                 715                 720

Val Cys His Ser Met Ala His Lys Leu Gly Ser Gln Phe His Ile Pro
                725                 730                 735

His Gly Leu Ala Asn Ala Leu Leu Ile Cys Asn Val Ile Arg Tyr Asn
            740                 745                 750

Ala Asn Asp Asn Pro Thr Lys Gln Thr Ala Phe Ser Gln Tyr Asp Arg
            755                 760                 765

Pro Gln Ala Arg Arg Tyr Ala Glu Ile Ala Asp His Leu Gly Leu
        770                 775                 780

Ser Ala Pro Gly Asp Arg Thr Ala Ala Lys Ile Glu Lys Leu Leu Ala
785                 790                 795                 800
```

```
Trp Leu Glu Thr Leu Lys Ala Glu Leu Gly Ile Pro Lys Ser Ile Arg
                805                 810                 815

Glu Ala Gly Val Gln Glu Ala Asp Phe Leu Ala Asn Val Asp Lys Leu
            820                 825                 830

Ser Glu Asp Ala Phe Asp Asp Gln Cys Thr Gly Ala Asn Pro Arg Tyr
        835                 840                 845

Pro Leu Ile Ser Glu Leu Lys Gln Ile Leu Leu Asp Thr Tyr Tyr Gly
    850                 855                 860

Arg Asp Tyr Val Glu Gly Glu Thr Ala Ala Lys Lys Glu Ala Ala Pro
865                 870                 875                 880

Ala Lys Ala Glu Lys Ala Lys Lys Ser Ala
                885                 890

<210> SEQ ID NO 22
<211> LENGTH: 891
<212> TYPE: PRT
<213> ORGANISM: Artificial sequence
<220> FEATURE:
<223> OTHER INFORMATION: mutant of Escherichia coli aldehyde-alcohol
      dehydrogenase

<400> SEQUENCE: 22

Met Ala Val Thr Asn Val Ala Glu Leu Asn Ala Leu Val Glu Arg Val
1               5                   10                  15

Lys Lys Ala Gln Arg Glu Tyr Ala Ser Phe Thr Gln Glu Gln Val Asp
                20                  25                  30

Lys Ile Phe Arg Ala Ala Ala Leu Ala Ala Ala Asp Ala Arg Ile Pro
            35                  40                  45

Leu Ala Lys Met Ala Val Ala Glu Ser Gly Met Gly Ile Val Glu Asp
    50                  55                  60

Lys Val Ile Lys Asn His Phe Ala Ser Glu Tyr Ile Tyr Asn Ala Tyr
65                  70                  75                  80

Lys Asp Glu Lys Thr Cys Gly Val Leu Ser Asp Asp Thr Phe Gly
                85                  90                  95

Thr Ile Thr Ile Ala Glu Pro Ile Gly Ile Ile Cys Gly Ile Val Pro
            100                 105                 110

Thr Thr Asn Pro Thr Ser Thr Ala Ile Phe Lys Ser Leu Ile Ser Leu
    115                 120                 125

Lys Thr Arg Asn Ala Ile Ile Phe Ser Pro His Pro Arg Ala Lys Asp
                130                 135                 140

Ala Thr Asn Lys Ala Ala Asp Ile Val Leu Gln Ala Ala Ile Ala Ala
145                 150                 155                 160

Gly Ala Pro Lys Asp Leu Ile Gly Trp Ile Asp Gln Pro Ser Val Glu
                165                 170                 175

Leu Ser Asn Ala Leu Met His His Pro Asp Ile Asn Leu Ile Leu Ala
            180                 185                 190

Thr Gly Gly Pro Gly Met Val Lys Ala Ala Tyr Ser Ser Gly Lys Pro
    195                 200                 205

Ala Ile Gly Val Gly Ala Gly Asn Thr Pro Val Val Ile Asp Glu Thr
    210                 215                 220

Ala Asp Ile Lys Arg Ala Val Ala Ser Val Leu Met Ser Lys Thr Phe
225                 230                 235                 240

Asp Asn Gly Val Ile Cys Ala Ser Glu Gln Ser Val Val Val Asp
                245                 250                 255

Ser Val Tyr Asp Ala Val Arg Glu Arg Phe Ala Thr His Gly Gly Tyr
```

```
                    260                 265                 270
Leu Leu Gln Gly Lys Glu Leu Lys Ala Val Gln Asp Val Ile Leu Lys
                275                 280                 285

Asn Gly Ala Leu Asn Ala Ala Ile Val Gly Gln Pro Ala Tyr Lys Ile
            290                 295                 300

Ala Glu Leu Ala Gly Phe Ser Val Pro Glu Asn Thr Lys Ile Leu Ile
305                 310                 315                 320

Gly Glu Val Thr Val Val Asp Glu Ser Glu Pro Phe Ala His Glu Lys
                325                 330                 335

Leu Ser Pro Thr Leu Ala Met Tyr Arg Ala Lys Asp Phe Glu Asp Ala
            340                 345                 350

Val Glu Lys Ala Glu Lys Leu Val Ala Met Gly Gly Ile Gly His Thr
            355                 360                 365

Ser Cys Leu Tyr Thr Asp Gln Asp Asn Gln Pro Ala Arg Val Ser Tyr
            370                 375                 380

Phe Gly Gln Lys Met Lys Thr Ala Arg Ile Leu Ile Asn Thr Pro Ala
385                 390                 395                 400

Ser Gln Gly Gly Ile Gly Asp Leu Tyr Asn Phe Lys Leu Ala Pro Ser
                405                 410                 415

Leu Thr Leu Gly Cys Gly Ser Trp Gly Gly Asn Ser Ile Ser Glu Asn
            420                 425                 430

Val Gly Pro Lys His Leu Ile Asn Lys Lys Thr Val Ala Lys Arg Ala
            435                 440                 445

Glu Asn Met Leu Trp His Lys Leu Pro Lys Ser Ile Tyr Phe Arg Arg
            450                 455                 460

Gly Ser Leu Pro Ile Ala Leu Asp Glu Val Ile Thr Asp Gly His Lys
465                 470                 475                 480

Arg Ala Leu Ile Val Thr Asp Arg Phe Leu Phe Asn Asn Gly Tyr Ala
                485                 490                 495

Asp Gln Ile Thr Ser Val Leu Lys Ala Ala Gly Val Glu Thr Glu Val
            500                 505                 510

Phe Phe Glu Val Glu Ala Asp Pro Thr Leu Ser Ile Val Arg Lys Gly
            515                 520                 525

Ala Glu Leu Ala Asn Ser Phe Lys Pro Asp Val Ile Ile Ala Leu Gly
            530                 535                 540

Gly Gly Ser Pro Met Asp Ala Ala Lys Ile Met Trp Val Met Tyr Glu
545                 550                 555                 560

His Pro Glu Thr His Phe Glu Arg Leu Ala Leu Arg Phe Met Asp Ile
                565                 570                 575

Arg Lys Arg Ile Tyr Lys Phe Pro Lys Met Gly Val Lys Ala Lys Met
            580                 585                 590

Ile Ala Val Thr Thr Thr Ser Gly Thr Gly Ser Glu Val Thr Pro Phe
            595                 600                 605

Ala Val Val Thr Asp Asp Ala Thr Gly Gln Lys Tyr Pro Leu Ala Asp
            610                 615                 620

Tyr Ala Leu Thr Pro Asp Met Ala Ile Val Asp Ala Asn Leu Val Met
625                 630                 635                 640

Asp Met Pro Lys Ser Leu Cys Ala Phe Gly Gly Leu Asp Ala Val Thr
                645                 650                 655

His Ala Met Glu Ala Tyr Val Ser Val Leu Ala Ser Glu Phe Ser Asp
            660                 665                 670

Gly Gln Ala Leu Gln Ala Leu Lys Leu Leu Lys Glu Tyr Leu Pro Ala
            675                 680                 685
```

```
Ser Tyr His Glu Gly Ser Lys Asn Pro Val Ala Arg Glu Arg Val His
    690                 695                 700

Ser Ala Ala Thr Ile Ala Gly Ile Ala Phe Ala Asn Ala Phe Leu Gly
705                 710                 715                 720

Val Cys His Ser Met Ala His Lys Leu Gly Ser Gln Phe His Ile Pro
                725                 730                 735

His Gly Leu Ala Asn Ala Leu Leu Ile Cys Asn Val Ile Arg Tyr Asn
                740                 745                 750

Ala Asn Asp Asn Pro Thr Lys Gln Thr Ala Phe Ser Gln Tyr Asp Arg
            755                 760                 765

Pro Gln Ala Arg Arg Tyr Ala Glu Ile Ala Asp His Leu Gly Leu
    770                 775                 780

Ser Ala Pro Gly Asp Arg Thr Ala Ala Lys Ile Glu Lys Leu Leu Ala
785                 790                 795                 800

Trp Leu Glu Thr Leu Lys Ala Glu Leu Gly Ile Pro Lys Ser Ile Arg
                805                 810                 815

Glu Ala Gly Val Gln Glu Ala Asp Phe Leu Ala Asn Val Asp Lys Leu
                820                 825                 830

Ser Glu Asp Ala Phe Asp Asp Gln Cys Thr Gly Ala Asn Pro Arg Tyr
            835                 840                 845

Pro Leu Ile Ser Glu Leu Lys Gln Ile Leu Leu Asp Thr Tyr Tyr Gly
    850                 855                 860

Arg Asp Tyr Val Glu Gly Glu Thr Ala Ala Lys Lys Glu Ala Ala Pro
865                 870                 875                 880

Ala Lys Ala Glu Lys Lys Ala Lys Lys Ser Ala
                885                 890

<210> SEQ ID NO 23
<211> LENGTH: 891
<212> TYPE: PRT
<213> ORGANISM: Artificial sequence
<220> FEATURE:
<223> OTHER INFORMATION: mutant of Escherichia coli aldehyde-alcohol
      dehydrogenase

<400> SEQUENCE: 23

Met Ala Val Thr Asn Val Ala Glu Leu Asn Ala Leu Val Glu Arg Val
1               5                   10                  15

Lys Lys Ala Gln Arg Glu Tyr Ala Ser Phe Thr Gln Glu Gln Val Asp
                20                  25                  30

Lys Ile Phe Arg Ala Ala Ala Leu Ala Ala Ala Asp Ala Arg Ile Pro
            35                  40                  45

Leu Ala Lys Met Ala Val Ala Glu Ser Gly Met Gly Ile Val Glu Asp
    50                  55                  60

Lys Val Ile Lys Asn His Phe Ala Ser Glu Tyr Ile Tyr Asn Ala Tyr
65                  70                  75                  80

Lys Asp Glu Lys Thr Cys Gly Val Leu Ser Asp Asp Thr Phe Gly
                85                  90                  95

Thr Ile Thr Ile Ala Glu Pro Ile Gly Ile Ile Cys Gly Ile Val Pro
            100                 105                 110

Thr Thr Asn Pro Thr Ser Thr Ala Ile Phe Lys Ser Leu Ile Ser Leu
    115                 120                 125

Lys Thr Arg Asn Ala Ile Ile Phe Ser Pro His Pro Arg Ala Lys Asp
    130                 135                 140

Ala Thr Asn Lys Ala Ala Asp Ile Val Leu Gln Ala Ala Ile Ala Ala
```

```
            145                 150                 155                 160
Gly Ala Pro Lys Asp Leu Ile Gly Trp Ile Asp Gln Pro Ser Val Glu
                    165                 170                 175
Leu Ser Asn Ala Leu Met His His Pro Asp Ile Asn Leu Ile Leu Ala
            180                 185                 190
Thr Gly Gly Pro Gly Met Val Lys Ala Ala Tyr Ser Ser Gly Lys Pro
        195                 200                 205
Ala Ile Gly Val Gly Ala Gly Asn Thr Pro Val Val Ile Asp Glu Thr
    210                 215                 220
Ala Asp Ile Lys Arg Ala Val Ala Ser Val Leu Met Ser Lys Thr Phe
225                 230                 235                 240
Asp Asn Gly Val Ile Cys Ala Ser Glu Gln Ser Val Val Val Val Asp
                245                 250                 255
Ser Val Tyr Asp Ala Val Arg Glu Arg Phe Ala Thr His Gly Gly Tyr
            260                 265                 270
Leu Leu Gln Gly Lys Glu Leu Lys Ala Val Gln Asp Val Ile Leu Lys
        275                 280                 285
Asn Gly Ala Leu Asn Ala Ala Ile Val Gly Gln Pro Ala Tyr Lys Ile
    290                 295                 300
Ala Glu Leu Ala Gly Phe Ser Val Pro Glu Asn Thr Lys Ile Leu Ile
305                 310                 315                 320
Gly Glu Val Thr Val Val Asp Glu Ser Glu Pro Phe Ala His Glu Lys
                325                 330                 335
Leu Ser Pro Thr Leu Ala Met Tyr Arg Ala Lys Asp Phe Glu Asp Ala
            340                 345                 350
Val Glu Lys Ala Glu Lys Leu Val Ala Met Gly Gly Ile Gly His Thr
        355                 360                 365
Ser Cys Leu Tyr Thr Asp Gln Asp Asn Gln Pro Ala Arg Val Ser Tyr
    370                 375                 380
Phe Gly Gln Lys Met Lys Thr Ala Arg Ile Leu Ile Asn Thr Pro Ala
385                 390                 395                 400
Ser Gln Gly Gly Ile Gly Asp Leu Tyr Asn Phe Lys Leu Ala Pro Ser
                405                 410                 415
Leu Thr Leu Gly Cys Gly Ser Trp Gly Gly Asn Ser Ile Ser Glu Asn
            420                 425                 430
Val Gly Pro Lys His Leu Ile Asn Lys Lys Thr Val Ala Lys Arg Ala
        435                 440                 445
Glu Asn Met Leu Trp His Lys Leu Pro Lys Ser Ile Tyr Phe Arg Arg
    450                 455                 460
Gly Ser Leu Pro Ile Ala Leu Asp Glu Val Ile Thr Asp Gly His Lys
465                 470                 475                 480
Arg Ala Leu Ile Val Thr Asp Arg Phe Leu Phe Asn Asn Gly Tyr Ala
                485                 490                 495
Asp Gln Ile Thr Ser Val Leu Lys Ala Ala Gly Val Glu Thr Glu Val
            500                 505                 510
Phe Phe Glu Val Glu Ala Asp Pro Thr Leu Ser Ile Val Arg Lys Gly
        515                 520                 525
Ala Glu Leu Ala Asn Ser Phe Lys Pro Asp Val Ile Ile Ala Leu Gly
    530                 535                 540
Gly Gly Ser Pro Met Asp Ala Ala Lys Ile Met Trp Val Met Tyr Glu
545                 550                 555                 560
His Pro Glu Thr His Phe Glu His Leu Ala Leu Arg Phe Met Asp Ile
                565                 570                 575
```

```
Arg Lys Arg Ile Tyr Lys Phe Pro Lys Met Gly Val Lys Ala Lys Met
            580                 585                 590

Ile Ala Val Thr Thr Thr Ser Gly Thr Gly Ser Glu Val Thr Pro Phe
            595                 600                 605

Ala Val Val Thr Asp Asp Ala Thr Gly Gln Lys Tyr Pro Leu Ala Asp
610                 615                 620

Tyr Ala Leu Thr Pro Asp Met Ala Ile Val Asp Ala Asn Leu Val Met
625                 630                 635                 640

Asp Met Pro Lys Ser Leu Cys Ala Phe Gly Leu Asp Ala Val Thr
                645                 650                 655

His Ala Met Glu Ala Tyr Val Ser Val Leu Ala Ser Glu Phe Ser Asp
            660                 665                 670

Gly Gln Ala Leu Gln Ala Leu Lys Leu Leu Lys Glu Tyr Leu Pro Ala
            675                 680                 685

Ser Tyr His Glu Gly Ser Lys Asn Pro Val Ala Arg Glu Arg Val His
            690                 695                 700

Ser Ala Ala Thr Ile Ala Gly Ile Ala Phe Ala Asn Ala Phe Leu Gly
705                 710                 715                 720

Val Cys His Ser Met Ala His Lys Leu Gly Ser Gln Phe His Ile Pro
                725                 730                 735

His Gly Leu Ala Asn Ala Leu Leu Ile Cys Asn Val Ile Arg Tyr Asn
            740                 745                 750

Ala Asn Asp Asn Pro Thr Lys Gln Thr Ala Phe Ser Gln Tyr Asp Arg
            755                 760                 765

Pro Gln Ala Arg Arg Tyr Ala Glu Ile Ala Asp His Leu Gly Leu
770                 775                 780

Ser Ala Pro Gly Asp Arg Thr Ala Ala Lys Ile Glu Lys Leu Leu Ala
785                 790                 795                 800

Trp Leu Glu Thr Leu Lys Ala Glu Leu Gly Ile Pro Lys Ser Ile Arg
                805                 810                 815

Glu Ala Gly Val Gln Glu Ala Asp Phe Leu Ala Asn Val Asp Lys Leu
            820                 825                 830

Ser Glu Asp Ala Phe Asp Gln Cys Thr Gly Ala Asn Pro Arg Tyr
            835                 840                 845

Pro Leu Ile Ser Glu Leu Lys Gln Ile Leu Leu Asp Thr Tyr Tyr Gly
            850                 855                 860

Arg Asp Tyr Val Glu Gly Glu Thr Ala Lys Lys Glu Ala Ala Pro
865                 870                 875                 880

Ala Lys Ala Glu Lys Lys Ala Lys Lys Ser Ala
            885                 890

<210> SEQ ID NO 24
<211> LENGTH: 873
<212> TYPE: PRT
<213> ORGANISM: Artificial sequence
<220> FEATURE:
<223> OTHER INFORMATION: mutant of Clostridium thermocellum aldehyde-
      alcohol dehydrogenase

<400> SEQUENCE: 24

Met Thr Lys Ile Ala Asn Lys Tyr Glu Val Ile Asp Asn Val Glu Lys
1               5                   10                  15

Leu Glu Lys Ala Leu Lys Arg Leu Arg Glu Ala Gln Ser Val Tyr Ala
            20                  25                  30

Thr Tyr Thr Gln Glu Gln Val Asp Lys Ile Phe Phe Glu Ala Ala Met
```

-continued

```
                35                  40                  45
Ala Ala Asn Lys Met Arg Ile Pro Leu Ala Lys Met Ala Val Glu Glu
                50                  55                  60
Thr Gly Met Gly Val Val Glu Asp Lys Val Ile Lys Asn His Tyr Ala
 65                  70                  75                  80
Ser Glu Tyr Ile Tyr Asn Ala Tyr Lys Asn Thr Lys Thr Cys Gly Val
                    85                  90                  95
Ile Glu Glu Asp Pro Ala Phe Gly Ile Lys Lys Ile Ala Glu Pro Leu
                100                 105                 110
Gly Val Ile Ala Ala Val Ile Pro Thr Thr Asn Pro Thr Ser Thr Ala
                115                 120                 125
Ile Phe Lys Thr Leu Ile Ala Leu Lys Thr Arg Asn Ala Ile Ile Ile
                130                 135                 140
Ser Pro His Pro Arg Ala Lys Asn Ser Thr Ile Glu Ala Ala Lys Ile
145                 150                 155                 160
Val Leu Glu Ala Val Lys Ala Gly Ala Pro Glu Gly Ile Ile Gly
                    165                 170                 175
Trp Ile Asp Val Pro Ser Leu Glu Leu Thr Asn Leu Val Met Arg Glu
                180                 185                 190
Ala Asp Val Ile Leu Ala Thr Gly Gly Pro Gly Leu Val Lys Ala Ala
                195                 200                 205
Tyr Ser Ser Gly Lys Pro Ala Ile Gly Val Gly Ala Gly Asn Thr Pro
                210                 215                 220
Ala Ile Ile Asp Asp Ser Ala Asp Ile Val Leu Ala Val Asn Ser Ile
225                 230                 235                 240
Ile His Ser Lys Thr Phe Asp Asn Gly Met Ile Cys Ala Ser Glu Gln
                    245                 250                 255
Ser Val Ile Val Leu Asp Gly Val Tyr Lys Glu Val Lys Lys Glu Phe
                260                 265                 270
Glu Lys Arg Gly Cys Tyr Phe Leu Asn Glu Asp Glu Thr Glu Lys Val
                275                 280                 285
Arg Lys Thr Ile Ile Ile Asn Gly Ala Leu Asn Ala Lys Ile Val Gly
                290                 295                 300
Gln Lys Ala His Thr Ile Ala Asn Leu Ala Gly Phe Glu Val Pro Glu
305                 310                 315                 320
Thr Thr Lys Ile Leu Ile Gly Glu Val Thr Ser Val Asp Ile Ser Glu
                    325                 330                 335
Glu Phe Ala His Glu Lys Leu Cys Pro Val Leu Ala Met Tyr Arg Ala
                340                 345                 350
Lys Asp Phe Asp Asp Ala Leu Asp Lys Ala Glu Arg Leu Val Ala Asp
                355                 360                 365
Gly Gly Phe Gly His Thr Ser Ser Leu Tyr Ile Asp Thr Val Thr Gln
                370                 375                 380
Lys Glu Lys Leu Gln Lys Phe Ser Glu Arg Met Lys Thr Cys Arg Ile
385                 390                 395                 400
Leu Val Asn Thr Pro Ser Ser Gln Gly Gly Ile Gly Asp Leu Tyr Asn
                    405                 410                 415
Phe Lys Leu Ala Pro Ser Leu Thr Leu Gly Cys Gly Ser Trp Gly Gly
                420                 425                 430
Asn Ser Val Ser Asp Asn Val Gly Val Lys His Leu Leu Asn Ile Lys
                435                 440                 445
Thr Val Ala Glu Arg Arg Glu Asn Met Leu Trp Phe Arg Thr Pro Glu
                450                 455                 460
```

Lys Ile Tyr Ile Lys Arg Gly Cys Leu Pro Val Ala Leu Asp Glu Leu
465                 470                 475                 480

Lys Asn Val Met Gly Lys Lys Ala Phe Ile Val Thr Asp Asn Phe
            485                 490                 495

Leu Tyr Asn Asn Gly Tyr Thr Lys Pro Ile Thr Asp Lys Leu Asp Glu
            500                 505                 510

Met Gly Ile Val His Lys Thr Phe Phe Asp Val Ser Pro Asp Pro Ser
            515                 520                 525

Leu Ala Ser Ala Lys Ala Gly Ala Ala Glu Met Leu Ala Phe Gln Pro
530                 535                 540

Asp Thr Ile Ile Ala Val Gly Gly Ser Ala Met Asp Ala Ala Lys
545                 550                 555                 560

Ile Met Trp Val Met Tyr Glu His Pro Glu Val Asp Phe Met Asn Met
                565                 570                 575

Ala Met Arg Phe Met Asp Ile Arg Lys Arg Val Tyr Thr Phe Pro Lys
            580                 585                 590

Met Gly Gln Lys Ala Tyr Phe Ile Ala Ile Pro Thr Ser Ala Gly Thr
            595                 600                 605

Gly Ser Glu Val Thr Pro Phe Ala Val Ile Thr Asp Glu Lys Thr Gly
610                 615                 620

Ile Lys Tyr Pro Leu Ala Asp Tyr Glu Leu Leu Pro Asp Met Ala Ile
625                 630                 635                 640

Val Asp Ala Asp Met Met Met Asn Ala Pro Lys Gly Leu Thr Ala Ala
                645                 650                 655

Ser Gly Ile Asp Ala Leu Thr His Ala Leu Glu Ala Tyr Val Ser Met
            660                 665                 670

Leu Ala Thr Asp Tyr Thr Asp Ser Leu Ala Leu Arg Ala Ile Lys Met
            675                 680                 685

Ile Phe Glu Tyr Leu Pro Arg Ala Tyr Glu Asn Gly Ala Ser Asp Pro
690                 695                 700

Val Ala Arg Glu Lys Met Ala Asn Ala Ala Thr Ile Ala Gly Met Ala
705                 710                 715                 720

Phe Ala Asn Ala Phe Leu Gly Val Cys His Ser Met Ala His Lys Leu
                725                 730                 735

Gly Ala Phe Tyr His Leu Pro His Gly Val Ala Asn Ala Leu Met Ile
            740                 745                 750

Asn Glu Val Ile Arg Phe Asn Ser Ser Glu Ala Pro Thr Lys Met Gly
            755                 760                 765

Thr Phe Pro Gln Tyr Asp His Pro Arg Thr Leu Glu Arg Tyr Ala Glu
            770                 775                 780

Ile Ala Asp Tyr Ile Gly Leu Lys Gly Lys Asn Asn Glu Glu Lys Val
785                 790                 795                 800

Glu Asn Leu Ile Lys Ala Ile Asp Glu Leu Lys Glu Lys Val Gly Ile
                805                 810                 815

Arg Lys Thr Ile Lys Asp Tyr Asp Ile Asp Glu Lys Glu Phe Leu Asp
            820                 825                 830

Arg Leu Asp Glu Met Val Glu Gln Ala Phe Asp Asp Gln Cys Thr Gly
            835                 840                 845

Thr Asn Pro Arg Tyr Pro Leu Met Asn Glu Ile Arg Gln Met Tyr Leu
            850                 855                 860

Asn Ala Tyr Tyr Gly Gly Ala Lys Lys
865                 870

<210> SEQ ID NO 25
<211> LENGTH: 2676
<212> TYPE: DNA
<213> ORGANISM: Artificial sequence
<220> FEATURE:
<223> OTHER INFORMATION: mutant of Escherichia coli aldehyde-alcohol dehydrogenase gene

<400> SEQUENCE: 25

| | | | | | |
|---|---|---|---|---|---|
| atggctgtta | ctaatgtcgc | tgaacttaac | gcactcgtag | agcgtgtaaa | aaaagcccag | 60 |
| cgtgaatatg | ccagtttcac | tcaagagcaa | gtagacaaaa | tcttccgcgc | cgccgctctg | 120 |
| gctgctgcag | atgctcgaat | cccactcgcg | aaaatggccg | ttgccgaatc | cggcatgggt | 180 |
| atcgtcgaag | ataaagtgat | caaaaaccac | tttgcttctg | aatatatcta | caacgcctat | 240 |
| aaagatgaaa | aaacctgtgg | tgttctgtct | gaagacgaca | cttttggtac | catcactatc | 300 |
| gctgaaccaa | tcggtattat | ttgcggtatc | gttccgacca | ctaacccgac | ttcaactgct | 360 |
| atcttcaaat | cgctgatcag | tctgaagacc | cgtaacgcca | ttatcttctc | cccgcacccg | 420 |
| cgtgcaaaag | atgccaccaa | caaagcggct | gatatcgttc | tgcaggctgc | tatcgctgcc | 480 |
| ggtgctccga | agatctgatc | ggctggatc | gatcaacctt | ctgttgaact | gtctaacgca | 540 |
| ctgatgcacc | acccagacat | caacctgatc | ctcgcgactg | gtggtccggg | catggttaaa | 600 |
| gccgcataca | gctccggtaa | accagctatc | ggtgtaggcg | cgggcaacac | tccagttgtt | 660 |
| atcgatgaaa | ctgctgatat | caaacgtgca | gttgcatctg | tactgatgtc | caaaaccttc | 720 |
| gacaacggcg | taatctgtgc | ttctgaacag | tctgttgttg | ttgttgactc | tgtttatgac | 780 |
| gctgtacgtg | aacgttttgc | aacccacggc | ggctatctgt | gcagggtaa | agagctgaaa | 840 |
| gctgttcagg | atgttatcct | gaaaaacggt | gcgctgaacg | cggctatcgt | tggtcagcca | 900 |
| gcctataaaa | ttgctgaact | ggcaggcttc | tctgtaccag | aaaacaccaa | gattctgatc | 960 |
| ggtgaagtga | ccgttgttga | tgaaagcgaa | ccgttcgcac | atgaaaaact | gtccccgact | 1020 |
| ctggcaatgt | accgcgctaa | agatttcgaa | gacgcggtag | aaaaagcaga | gaaactggtt | 1080 |
| gctatgggcg | gtatcggtca | tacctcttgc | ctgtacactg | accaggataa | ccaaccggct | 1140 |
| cgcgtttctt | acttcggtca | gaaatgaaa | acggcgcgta | cctgattaa | cacccagcg | 1200 |
| tctcagggtg | gtatcggtga | cctgtataac | ttcaaactcg | caccttccct | gactctgggt | 1260 |
| tgtggttctt | ggggtggtaa | ctccatctct | gaaaacgttg | gtccgaaaca | cctgatcaac | 1320 |
| aagaaaaccg | ttgctaagcg | agctgaaaac | atgttgtggc | acaaacttcc | gaaatctatc | 1380 |
| tacttccgcc | gtggctccct | gccaatcgcg | ctggatgaag | tgattactga | tggccacaaa | 1440 |
| cgtgcgctca | tcgtgactga | ccgcttcctg | ttcaacaatg | ttatgctga | tcagatcact | 1500 |
| tccgtactga | aagcagcagg | cgttgaaact | gaagtcttct | tcgaagtaga | agcggacccg | 1560 |
| accctgagca | tcgttcgtaa | aggtgcagaa | ctggcaaact | ccttcaaacc | agacgtgatt | 1620 |
| atcgcgctgg | tggtggttc | cccgatggac | gccgcgaaga | tcatgtgggt | tatgtacgaa | 1680 |
| catccggaaa | ctcacttcga | aaagctggcg | ctgcgcttta | tggatatccg | taacgtatc | 1740 |
| tacaagttcc | cgaaaatggg | cgtgaaagcg | aaaatgatcg | ctgtcaccac | cacttctggt | 1800 |
| acaggttctg | aagtcactcc | gtttgcggtt | gtaactgacg | acgctactgg | tcagaaatat | 1860 |
| ccgctggcag | actatgcgct | gactccggat | atggcgattg | tcgacgccaa | cctggttatg | 1920 |
| gacatgccga | gtccctgtg | tgctttcggt | ggtctggacg | cagtaactca | cgccatggaa | 1980 |
| gcttatgttt | ctgtactggc | atctgagttc | tctgatggtc | aggctctgca | ggcactgaaa | 2040 |

```
ctgctgaaag aatatctgcc agcgtcctac cacgaagggt ctaaaaatcc ggtagcgcgt   2100
gaacgtgttc acagtgcagc gactatcgcg ggtatcgcgt ttgcgaacgc cttcctgggt   2160
gtatgtcact caatggcgca caaactgggt tcccagttcc atattccgca cggtctggca   2220
aacgccctgc tgatttgtaa cgttattcgc tacaatgcga acgacaaccc gaccaagcag   2280
actgcattca gccagtatga ccgtccgcag gctcgccgtc gttatgctga aattgccgac   2340
cacttgggtc tgagcgcacc gggcgaccgt actgctgcta agatcgagaa actgctggca   2400
tggctggaaa cgctgaaagc tgaactgggt attccgaaat ctatccgtga agctggcgtt   2460
caggaagcag acttcctggc gaacgtggat aaactgtctg aagatgcatt cgatgaccag   2520
tgcaccggcg ctaacccgcg ttacccgctg atctccgagc tgaaacagat tctgctggat   2580
acctactacg gtcgtgatta tgtagaaggt gaaactgcag cgaagaaaga agctgctccg   2640
gctaaagctg agaaaaaagc gaaaaaatcc gcttaa                              2676

<210> SEQ ID NO 26
<211> LENGTH: 2676
<212> TYPE: DNA
<213> ORGANISM: Artificial sequence
<220> FEATURE:
<223> OTHER INFORMATION: mutant of Escherichia coli aldehyde-alcohol
      dehydrogenase gene

<400> SEQUENCE: 26
atggctgtta ctaatgtcgc tgaacttaac gcactcgtag agcgtgtaaa aaaagcccag    60
cgtgaatatg ccagtttcac tcaagagcaa gtagacaaaa tcttccgcgc cgccgctctg   120
gctgctgcag atgctcgaat cccactcgcg aaaatggccg ttgccgaatc cggcatgggt   180
atcgtcgaag ataaagtgat caaaaaccac tttgcttctg aatatatcta caacgcctat   240
aaagatgaaa aacctgtggg tgttctgtct gaagacgaca cttttggtac catcactatc   300
gctgaaccaa tcggtattat ttgcggtatc gttccgacca ctaacccgac ttcaactgct   360
atcttcaaat cgctgatcag tctgaagacc cgtaacgcca ttatcttctc cccgcacccg   420
cgtgcaaaag atgccaccaa caaagcggct gatatcgttc tgcaggctgc tatcgctgcc   480
ggtgctccga agatctgat cggctggatc gatcaacctt ctgttgaact gtctaacgca   540
ctgatgcacc acccagacat caacctgatc ctcgcgactg gtggtccggg catggttaaa   600
gccgcataca gctccggtaa accagctatc ggtgtaggcg cgggcaacac tccagttgtt   660
atcgatgaaa ctgctgatat caaacgtgca gttgcatctg tactgatgtc caaaaccttc   720
gacaacggcg taatcgtgtg cttctgaacag tctgttgttg ttgttgactc tgtttatgac   780
gctgtacgtg aacgttttgc aacccacggc ggctatctgt tgcagggtaa agagctgaaa   840
gctgttcagg atgttatcct gaaaaacggt gcgctgaacg cggctatcgt tggtcagcca   900
gcctataaaa ttgctgaact ggcaggcttc tctgtaccag aaaacaccaa gattctgatc   960
ggtgaagtga ccgttgttga tgaaagcgaa ccgttcgcac atgaaaaact gtccccgact   1020
ctggcaatgt accgcgctaa agatttcgaa gacgcggtag aaaaagcaga gaaactggtt   1080
gctatgggcg gtatcggtca tacctcttgc ctgtacactg accaggataa ccaaccggct   1140
cgcgtttctt acttcggtca gaaatgaaa acggcgcgta cctgattaa cacccccagcg   1200 tctcagggtg gtatcggtga cctgtataac ttcaaactcg caccttccct gactctgggt   1260
tgtggttctt ggggtggtaa ctccatctct gaaacgttg gtccgaaaca cctgatcaac   1320
aagaaaaccg ttgctaagcg agctgaaaac atgttgtggc acaaacttcc gaaatctatc   1380
```

```
tacttccgcc gtggctccct gccaatcgcg ctggatgaag tgattactga tggccacaaa    1440
cgtgcgctca tcgtgactga ccgcttcctg ttcaacaatg gttatgctga tcagatcact    1500
tccgtactga aagcagcagg cgttgaaact gaagtcttct tcgaagtaga agcggacccg    1560
accctgagca tcgttcgtaa aggtgcagaa ctggcaaact ccttcaaacc agacgtgatt    1620
atcgcgctgg tggtggttc  cccgatggac gccgcgaaga tcatgtgggt tatgtacgaa    1680
catccggaaa ctcacttcga aaaactggcg ctgcgcttta tggatatccg taaacgtatc    1740
tacaagttcc cgaaaatggg cgtgaaagcg aaaatgatcg ctgtcaccac cacttctggt    1800
acaggttctg aagtcactcc gtttgcggtt gtaactgacg acgctactgg tcagaaatat    1860
ccgctggcag actatgcgct gactccggat atggcgattg tcgacgccaa cctggttatg    1920
gacatgccga gtccctgtg  tgctttcggt ggtctggacg cagtaactca cgccatggaa    1980
gcttatgttt ctgtactggc atctgagttc tctgatggtc aggctctgca ggcactgaaa    2040
ctgctgaaag aatatctgcc agcgtcctac cacgaagggt ctaaaaatcc ggtagcgcgt    2100
gaacgtgttc acagtgcagc gactatcgcg ggtatcgcgt tgcgaacgc  cttcctgggt    2160 gtatgtcact caatggcgca caaactgggt tcccagttcc atattccgca cggtctggca    2220
aacgccctgc tgatttgtaa cgttattcgc tacaatgcga acgacaaccc gaccaagcag    2280
actgcattca gccagtatga ccgtccgcag gctcgccgtc gttatgctga aattgccgac    2340
cacttgggtc tgagcgcacc gggcgaccgt actgctgcta gatcgagaa  actgctggca    2400 tggctggaaa cgctgaaagc tgaactgggt attccgaaat ctatccgtga agctggcgtt    2460
caggaagcag acttcctggc gaacgtggat aaactgtctg aagatgcatt cgatgaccag    2520
tgcaccggcg ctaacccgcg ttacccgctg atctccgagc tgaaacagat tctgctggat    2580
acctactacg tcgtgatta  tgtagaaggt gaaactgcag cgaagaaaga agctgctccg    2640
gctaaagctg agaaaaaagc gaaaaaatcc gcttaa                              2676
```

<210> SEQ ID NO 27
<211> LENGTH: 2622
<212> TYPE: DNA
<213> ORGANISM: Artificial sequence
<220> FEATURE:
<223> OTHER INFORMATION: mutant of Clostridium thermocellum aldehyde-
    alcohol dehydrogenase gene

<400> SEQUENCE: 27

```
atgacgaaaa tagcgaataa atacgaagtt attgataatg ttgaaaagct tgaaaaggct     60
ttgaaacgtt taagagaagc tcaaagtgtt tatgcaacct atacacagga gcaggttgac    120
aaaattttct ttgaggcggc aatggcggcc aataaaatga aattcctct  tgccaaaatg    180 gctgtggagg aaacaggcat gggagtggtt gaagacaagg ttatcaaaaa ccactatgct    240
tctgagtata tctataatgc gtacaaaaac actaaaacct gcggtgttat tgaagaggac    300
cctgctttcg gtattaaaaa aatagcagag cctttggggg ttattgcggc ggttatacct    360
actacgaatc cgacatcgac agcaatcttt aagactctta ttgcattaaa gacgagaaat    420
gcaattatta taagcccaca ccccagggca aaaaactcaa cgatagaagc ggcgaaaatt    480
gttttggagg cggccgttaa agccggtgct ccggaaggca tcattggctg gattgatgtg    540
ccgagccttg aacttaccaa cctggtaatg agagaagcag atgtgattct cgcaacaggc    600
ggtcccggac tggttaaagc agcttactct tcgggcaaac cggctattgg tgtcggagcg    660
ggcaatactc ctgcaattat tgatgattcg gccgacattg tcttggcagt gaactcaata    720
```

```
atacattcaa aaactttcga caacggtatg atttgtgctt cagagcaatc ggtcattgtt      780
ctggacgggg tatataaaga ggtaaaaaaa gaatttgaaa aaagaggatg ctatttctta      840
aatgaagatg aaactgaaaa ggtaagaaaa acaattataa taaacggtgc gttaaatgcc      900
aagatagtag gtcagaaagc tcacacaatt gcaaaccttg caggttttga ggtacccgag      960
actacaaaaa ttctgatagg cgaagttacc agcgtggata tttccgaaga atttgcccac     1020
gaaaagttgt gcccggtact ggcaatgtac agggcaaagg attttgacga tgcccttgat     1080
aaagcagaaa ggttggtagc tgacggtgga tttggccata cttcgtcact ttatatagat     1140
acggtaacac agaaagagaa acttcagaaa ttctctgaaa ggatgaaaac ctgccgtata     1200
ttggttaata cgccgtcatc ccagggaggt atcggtgacc tttacaactt caagcttgct     1260
ccgtctctca ccctcggctg cggttcctgg gaggaaatt cagtttccga caatgtggga     1320
gtcaagcatt tgttaaacat taaaacagtt gccgagagga gagagaacat gctctggttc     1380
agaacacctg aaaagattta tataaaaga ggttgtctgc ctgttgcatt ggatgagctt     1440
aaaaatgtaa tgggtaaaaa gaaagcattt attgtaacgg ataacttcct gtacaataac     1500
ggctacacca agccgattac ggataagctg gatgaaatgg gaattgtgca caagaccttc     1560
tttgatgtgt ctccagaccc atcccttgca tctgccaaag ccggtgcggc agaaatgctg     1620
gctttccagc ctgacaccat aattgcggtc ggcggcggat ctgccatgga cgcggccaaa     1680
atcatgtggg tgatgtatga acatccggaa gttgactttta tgaacatggc aatgagattt     1740
atggatataa gaaagagagt ttacaccttc ccgaagatgg gacagaaggc atactttatc     1800
gcaattccga cttccgcggg tacaggttca gaagtgacac cttttgcggt tattactgat     1860
gaaaaaacag gaattaaata ccctctggcc gactatgaat tgttgccgga catggctatt     1920
gtagatgccg atatgatgat gaatgctcca aagggactta ccgcagcttc cggtatagac     1980
gcattgaccc acgctctgga agcctatgtt tcaatgcttg cgaccgacta tacggatagc     2040
cttgcccttc gtgcaataaa gatgatattt gaatatctcc cgagagccta tgaaaacggt     2100
gcaagtgacc cggttgcaag agagaaaatg gccaatgccg caacaatagc cggaatggct     2160
tttgccaatg cctttttggg tgtatgccat tcaatggcgc acaaactggg tgcttttttat     2220
cacctgcccc acggtgttgc caatgcactt atgataaacg aagtaatcag attcaactca     2280
tccgaggctc cgaccaagat gggtactttc ccgcagtatg accatccgcg cacgctggaa     2340
aggtatgcag aaattgccga ttatatcgga cttaagggca agaataacga agaaaaagtt     2400
gaaaacttga ttaaagctat tgatgagctt aaagaaaagg tgggcatcag gaagaccatc     2460
aaagattatg acatagatga aaaggaattt ttggacagac tggacgaaat ggtggaacag     2520
gcttttgacg accagtgcac aggtacaaat ccaagatacc cgcttatgaa tgaaatcagg     2580
caaatgtatc tgaacgctta ttacggaggt gcgaagaaat aa                        2622
```

<210> SEQ ID NO 28
<211> LENGTH: 2622
<212> TYPE: DNA
<213> ORGANISM: Artificial sequence
<220> FEATURE:
<223> OTHER INFORMATION: mutant of Clostridium thermocellum aldehyde-
      alcohol dehydrogenase gene

<400> SEQUENCE: 28

```
atgacgaaaa tagcgaataa atacgaagtt attgataatg ttgaaaagct tgaaaaggct       60
ttgaaacgtt taagagaagc tcaaagtgtt tatgcaacct atacacagga gcaggttgac      120
```

| | |
|---|---|
| aaaatttct ttgaggcggc aatggcggcc aataaaatga gaattcctct tgccaaaatg | 180 |
| gctgtggagg aaacaggcat gggagtggtt gaagacaagg ttatcaaaaa ccactatgct | 240 |
| tctgagtata tctataatgc gtacaaaaac actaaaacct gcggtgttat tgaagaggac | 300 |
| cctgctttcg gtattaaaaa aatagcgagg cctttggggg ttattgcggc ggttataccct | 360 |
| actacgaatc cgacatcgac agcaatcttt aagactctta ttgcattaaa gacgagaaat | 420 |
| gcaattatta taagcccaca ccccagggca aaaaactcaa cgatagaagc ggcgaaaatt | 480 |
| gttttggagg cggccgttaa agccggtgct ccggaaggca tcattggctg gattgatgtg | 540 |
| ccgagccttg aacttaccaa cctggtaatg agagaagcag atgtgattct cgcaacaggc | 600 |
| ggtcccggac tggttaaagc agcttactct tcgggcaaac cggctattgg tgtcggagcg | 660 |
| ggcaatactc ctgcaattat tgatgattcg gccgacattg tcttggcagt gaactcaata | 720 |
| atacattcaa aaactttcga caacggtatg atttgtgctt cagagcaatc ggtcattgtt | 780 |
| ctggacgggg tatataaaga ggtaaaaaaa gaatttgaaa aaagaggatg ctatttctta | 840 |
| aatgaagatg aaactgaaaa ggtaagaaaa acaattataa taaacggtgc gttaaatgcc | 900 |
| aagatagtag gtcagaaagc tcacacaatt gcaaaccttg caggttttga ggtacccgag | 960 |
| actacaaaaa ttctgatagg cgaagttacc agcgtggata tttccgaaga atttgcccac | 1020 |
| gaaaagttgt gcccggtact ggcaatgtac agggcaaagg attttgacga tgcccttgat | 1080 |
| aaagcagaaa ggttggtagc tgacggtgga tttggccata cttcgtcact ttatatagat | 1140 |
| acggtaacac agaaagagaa acttcagaaa ttctctgaaa ggatgaaaac ctgccgtata | 1200 |
| ttggttaata cgccgtcatc ccagggaggt atcggtgacc tttacaactt caagcttgct | 1260 |
| ccgtctctca ccctcggctg cggttcctgg ggaggaaatt cagtttccga caatgtggga | 1320 |
| gtcaagcatt tgttaaacat taaaacagtt gccgagagga gagagaacat gctctggttc | 1380 |
| agaacacctg aaaagattta tataaaaaga ggttgtctgc ctgttgcatt ggatgagctt | 1440 |
| aaaaatgtaa tgggtaaaaa gaaagcattt attgtaacgg ataacttcct gtacaataac | 1500 |
| ggctacacca agccgattac ggataagctg gatgaaatgg gaattgtgca caagaccttc | 1560 |
| tttgatgtgt ctccagaccc atcccttgca tctgccaaag ccggtgcggc agaaatgctg | 1620 |
| gctttccagc ctgacaccat aattgcggtc ggcggcggat ctgccatgga cgcggccaaa | 1680 |
| atcatgtggg tgatgtatga acatccggaa gttgactta tgaatatggc aatgagattt | 1740 |
| atggatataa gaaagagagt ttacaccttc ccgaagatgg gacagaaggc atactttatc | 1800 |
| gcaattccga cttccgcggg tacaggttca gaagtgacac cttttgcggt tattactgat | 1860 |
| gaaaaaacag gaattaaata ccctctggcc gactatgaat tgttgccgga catggctatt | 1920 |
| gtagatgccg atatgatgat gaatgctcca aagggactta ccgcagcttc cggtatagac | 1980 |
| gcattgaccc acgctctgga agcctatgtt tcaatgcttg cgaccgacta tacggatagc | 2040 |
| cttgcccttc gtgcaataaa gatgatattt gaatatctcc cgagagccta tgaaaacggt | 2100 |
| gcaagtgacc cggttgcaag agagaaaatg gccaatgccg caacaatagc cggaatggct | 2160 |
| tttgccaatg ccttttgggg tgtatgccat tcaatggcgc acaaactggg tgctttttat | 2220 |
| cacctgcccc acgtgttgc caatgcactt atgataaacg aagtaatcag attcaactca | 2280 |
| tccgaggctc cgaccaagat gggtactttc ccgcagtatg accatccgcg cacgctggaa | 2340 |
| aggtatgcag aaattgccga ttatatcgga cttaagggca agaataacga agaaaaagtt | 2400 |
| gaaaacttga ttaaagctat tgatgagctt aagaaaaagg tgggcatcag gaagaccatc | 2460 |
| aaagattatg acatagatga aaaggaattt ttggacagac tggacgaaat ggtggaacag | 2520 |

```
gcttttgacg accagtgcac aggtacaaat ccaagatacc cgcttatgaa tgaaatcagg    2580
caaatgtatc tgaacgctta ttacggaggt gcgaagaaat aa                      2622
```

<210> SEQ ID NO 29
<211> LENGTH: 1119
<212> TYPE: DNA
<213> ORGANISM: Geobacillus stearothermophilus

<400> SEQUENCE: 29

```
atgaagatcg gcattccaaa agaaatcaaa acaatgaaa accgcgtcgc catcactccg      60
gcaggcgtga tgacgctcgt caaagcgggg catgacgtgt atgtggagac ggaagccggc    120
gctgggtcgg ggttttctga cgctgaatat gaaaaagccg gggcagtgat cgtgacgaaa    180
gcggaagatg cctgggcggc ggagatggtg ttgaaagtga agaaccgct gcctgaggag     240
ttccgctatt ttcgccccgg attgattttg tttacgtatt tgcatttagc cgcggccgaa    300
gcgctcacga aagcgctcgt cgagcaaaaa gtggtcggca tcgcttacga gacggtgcag    360
cttgcgaacg gctcgctgcc gctgttgacg ccgatgagtg aagtcgccgg ccgcatgtcg    420
gtgcaagtcg gcgcccagtt tctcgagaag ccgcacggcg ggaaaggcat tttgcttggc    480
ggcgtgcccg gggtgcggcg cggcaaagtg acgatcatcg gcggcggcac agcggggacg    540
aacgcgggga aaatcgcggt cggcctcggg gcggacgtga cgattttgga cattaacgcc    600
gagcggctgc gcgagctcga tgatttgttc ggcgaccaag tgacgacgtt gatgtccaac    660
tcgtatcata tcgccgaatg cgtgcgggaa tcggatttgg tcgtcggcgc cgtcttgatc    720
ccgggggcga aagcgccaaa gcttgtgacg gaagagatgt tgcgctcgat gatgccaggc    780
tcggtgttgg tcgacgtcgc cattgaccaa ggcggcattt tcgaaacgac cgaccgcgtc    840
acgacgcacg acgatccgac atacgtcaag cacgcgtcg ttcattacgc cgtcgcgaac     900
atgccgggcg ctgtgccgcg cacgtcgaca ttcgcgctta cgaacgtcac gatcccatac    960
gccttgcaaa tcgccaacaa aggctaccgc gccgcgtgct tggataaccc ggcgctgtta    1020
aaagggatca cacgctcga cgggcacatc gtgtacgaag cggtcgcggc ggcgcacaac    1080
atgccgtata cggatgctca ttcgttgctg cagggatga                          1119
```

<210> SEQ ID NO 30
<211> LENGTH: 1134
<212> TYPE: DNA
<213> ORGANISM: Geobacillus stearothermophilus

<400> SEQUENCE: 30

```
atgattattg gagtgccaaa ggaaatcaaa aataacgaaa accgtgtcgc cattacgccg     60
gctggcgttt tgtcattcgt tcaggctgga catacggttc tgattgagaa agaggcaggg    120
gttggaagcg gtttcagcga cagcgattac gcccgtgccg agcacaaat catcgagcgg     180
gcggaagatg tttgggcgca agccgatatg gtgatgaaag tgaaagagcc gctgccaagc    240
gaatacggct atttccgccc aggtctcatt ttgttcacct atttgcattt ggccgccgac    300
ccggagttga cacgcgcctt aaaagaaagc ggcgtcatcg ccattgccta tgagacggtg    360
caagtcggcc gcacactgcc gctgttgaca ccaatgagcg aagtcgccgg acggatggcc    420
gcgcaaattg gagcgcaatt tttagaaaaa ccgtacggcg gcaaaggcat cttgcttggc    480
ggcgtcccag gcgttgcccg cggcaaagtg acgatcatcg gcggcggagt cgtcggcacg    540
aacgcagcga aagtcgcggt cggcctcggg gcagatgtca cgattatcga cttgaacgcg    600
```

```
gatcgcctgc gcgagcttga cgacattttc ggcaaccaaa ttacgacgct catgtccaac      660
ccaatgaaca tcgccgaagc ggttgctgag gccgaccttg tcatcggcgc cgtcctcatc      720
ccgggagcgc gggcgccgaa gctcgtcacc gaggacatgg tgaaagcgat gaaaccgggt      780
tcggtcatcg tcgatgtcgc catcgaccaa ggggcatcg tcgagacgag cgaccacgtc       840
acgacacatg acgacccgac gtacgtcaaa cacggcgtcg tccattatgc ggtcgccaac      900
atgcctggcg ccgtcccgcg cacctcaacg atcgccttga cgaacgtcac catgccatac      960
gccttgcaaa tcgccaacaa aggcgtcatc caagccatta cagacaaccc ggcgcttgag     1020
cttggcgtca acgtcgccaa cggtgaaatc acgtacgaag cggtcgcccg cgacctcggt     1080
taccgctacg tcccggcccg cgaagcgctc gggaaaacgt tggccgccaa ctaa           1134
```

<210> SEQ ID NO 31
<211> LENGTH: 1110
<212> TYPE: DNA
<213> ORGANISM: Thermus thermophilus

<400> SEQUENCE: 31

```
atggtgatcg gcgtgccgaa ggagatcaag accttggaga accgggtggc cctcacgccc       60
ggcggggtgg agagcctggt caggcgcggc cacaccgtgc tggtggagcg ggggccggg       120 gagggctcgg ggcttccga cgcggagtac gccgggccg ggccgagct cgtgggccgg       180 gaggaggcct ggggtgcgga gatggtggtg aaggtgaagg agcccctacc cgaggagtac      240
ggcttcctgc gggagggcct catcctcttc acctaccttc acctggccgc ggaccgcggc      300
ctcaccgagg ccatgctccg tagcggggtc acgggcatcg cctacgagac cgtccagctt      360
cccgacggca ccctcccct cctcgtcccc atgagcgagg tggcggggcg gatggcccc      420 caggtggggg cccagttcct ggagaagccc aaggggggcc ggggggtcct cctcggggg      480 gtgccggggg tggccccggc cagcgtggtg atcctcgggg gcgggaccgt gggcaccaac      540
gcggccaaga tcgccctggg gatggggggcc caggtgacca tcctggacgt gaaccacaag      600
cgcctccagt atctggacga cgtcttcggc gggcgggtga tcaccctcac cgccaccgag      660
gccaacatca aaagagcgt ccagcacgcg gacctcctca tcggggccgt cctcgtcccc      720
ggggccaagg cccccaagct cgtcacccgg gacatgctct ctctgatgaa ggaggggagcg      780 gtgatcgtgg acgtggccgt ggaccagggg gggtgcgtgg agaccatccg gcccaccacc      840
cacgccgagc ccacctacgt ggtggacggg gtggtccact acgggtggc caacatgccc      900 ggggcggtgc ccaggaccag cacccttgcc ctcaccaacc agaccctgcc ctacgtgttg      960
aagctcgcgg agaagggct ggacgccctt ctggaggacg cggcccttct caaggggctc     1020
aacacccaca aaggccgcct cacccacccc ggggtggccg aggccttcgg cctgccctac     1080
acgcctcccg aggaggcctt gaggggggtga                                     1110
```

<210> SEQ ID NO 32
<211> LENGTH: 1038
<212> TYPE: DNA
<213> ORGANISM: Thermus thermophilus

<400> SEQUENCE: 32

```
atggagttcg gcgtgcccag agaacggtcg ggcggggaga tcccggaaag gcgggtgccc       60
ctcacgcccc aggggggtgcg ggagctcgtc gcctcggggc accgggtcta cgtggagcgg      120
ggcgcggggg aagggcggg ctttcccgac gaggcctacg aggaagcggg ggccaggctc       180
gtgggccggg aggaggcctt cggccgcccc caggtggtgc tcaaggtggc ccgccccacc      240
```

-continued

```
ctcgaggagg tggggctcat gcgcaaaaac gccgttctca tggccttcct ccacctggcg    300
gtggcggaaa gccccctcgt ggaggccatg cccaaaagg gcctcaccgc catcggctac     360
gagctggtgg gcgaggaggg ccgccgcccc gtcctgaagg ccatgagcga gatcgccggg    420
cgcatggccc cccagctcgc cgggcggctc ctcgaggccc ccagggccc gggcatcctc     480 ctctccggcc tggtgggcat cccccggcg gacgtggtcg tcctggggc ggggtcctg       540 ggccgggcg cggcgcgggc ctttctgggc gcggggcct cggtccacct cctgaccgg       600 gcccttcccc cgctggagga ggccgcccgg gaggccccgg gggccatcac cgccctcgtc    660
acccaggacc gcctggagcg gtacgtggcc ttcgccgacg tcctggtggg ggcggtggcc    720
gtccctgggg agcgcacccc ccttctcctc acccgcggcc tcctcgcccg catgcgcccc    780
ggaagcgtcc tcctggactt ctccatagac caggggggcg tctcggaaac cagccgccct    840
ggggtctacc aggagatggg cgtcacccac ttctgcctcc caacgtccc cgccctcgtc    900 ccccgcaccg caagccacgc cctcaccctc accctcctcc cctacctgct ccggatccag    960
gaagaccccc tggcccttcc cgggctccgc caggggggcct acctcctctt cggcgagaaa   1020
ggaggccacc tagaatga                                                  1038
```

<210> SEQ ID NO 33
<211> LENGTH: 372
<212> TYPE: PRT
<213> ORGANISM: Geobacillus stearothermophilus

<400> SEQUENCE: 33

```
Met Lys Ile Gly Ile Pro Lys Glu Ile Lys Asn Asn Glu Asn Arg Val
1               5                   10                  15

Ala Ile Thr Pro Ala Gly Val Met Thr Leu Val Lys Ala Gly His Asp
            20                  25                  30

Val Tyr Val Glu Thr Glu Ala Gly Ala Gly Ser Gly Phe Ser Asp Ala
        35                  40                  45

Glu Tyr Glu Lys Ala Gly Ala Val Ile Val Thr Lys Ala Glu Asp Ala
    50                  55                  60

Trp Ala Ala Glu Met Val Leu Lys Val Lys Glu Pro Leu Pro Glu Glu
65                  70                  75                  80

Phe Arg Tyr Phe Arg Pro Gly Leu Ile Leu Phe Thr Tyr Leu His Leu
                85                  90                  95

Ala Ala Ala Glu Ala Leu Thr Lys Ala Leu Val Glu Gln Lys Val Val
            100                 105                 110

Gly Ile Ala Tyr Glu Thr Val Gln Leu Ala Asn Gly Ser Leu Pro Leu
        115                 120                 125

Leu Thr Pro Met Ser Glu Val Ala Gly Arg Met Ser Val Gln Val Gly
    130                 135                 140

Ala Gln Phe Leu Glu Lys Pro His Gly Gly Lys Gly Ile Leu Leu Gly
145                 150                 155                 160

Gly Val Pro Gly Val Arg Arg Gly Lys Val Thr Ile Ile Gly Gly Gly
                165                 170                 175

Thr Ala Gly Thr Asn Ala Gly Lys Ile Ala Val Gly Leu Gly Ala Asp
            180                 185                 190

Val Thr Ile Leu Asp Ile Asn Ala Glu Arg Leu Arg Glu Leu Asp Asp
        195                 200                 205

Leu Phe Gly Asp Gln Val Thr Thr Leu Met Ser Asn Ser Tyr His Ile
    210                 215                 220
```

```
Ala Glu Cys Val Arg Glu Ser Asp Leu Val Gly Ala Val Leu Ile
225                 230                 235                 240

Pro Gly Ala Lys Ala Pro Lys Leu Val Thr Glu Glu Met Val Arg Ser
                245                 250                 255

Met Met Pro Gly Ser Val Leu Val Asp Val Ala Ile Asp Gln Gly Gly
            260                 265                 270

Ile Phe Glu Thr Thr Asp Arg Val Thr Thr His Asp Pro Thr Tyr
        275                 280                 285

Val Lys His Gly Val Val His Tyr Ala Val Ala Asn Met Pro Gly Ala
    290                 295                 300

Val Pro Arg Thr Ser Thr Phe Ala Leu Thr Asn Val Thr Ile Pro Tyr
305                 310                 315                 320

Ala Leu Gln Ile Ala Asn Lys Gly Tyr Arg Ala Ala Cys Leu Asp Asn
                325                 330                 335

Pro Ala Leu Leu Lys Gly Ile Asn Thr Leu Asp Gly His Ile Val Tyr
            340                 345                 350

Glu Ala Val Ala Ala His Asn Met Pro Tyr Thr Asp Ala His Ser
    355                 360                 365

Leu Leu Gln Gly
    370

<210> SEQ ID NO 34
<211> LENGTH: 377
<212> TYPE: PRT
<213> ORGANISM: Geobacillus stearothermophilus

<400> SEQUENCE: 34

Met Ile Ile Gly Val Pro Lys Glu Ile Lys Asn Asn Glu Asn Arg Val
1               5                   10                  15

Ala Ile Thr Pro Ala Gly Val Leu Ser Phe Val Gln Ala Gly His Thr
            20                  25                  30

Val Leu Ile Glu Lys Glu Ala Gly Val Gly Ser Gly Phe Ser Asp Ser
        35                  40                  45

Asp Tyr Ala Arg Ala Gly Ala Gln Ile Ile Glu Arg Ala Glu Asp Val
    50                  55                  60

Trp Ala Gln Ala Asp Met Val Met Lys Val Lys Glu Pro Leu Pro Ser
65                  70                  75                  80

Glu Tyr Gly Tyr Phe Arg Pro Gly Leu Ile Leu Phe Thr Tyr Leu His
                85                  90                  95

Leu Ala Ala Asp Pro Glu Leu Thr Arg Ala Leu Lys Glu Ser Gly Val
            100                 105                 110

Ile Ala Ile Ala Tyr Glu Thr Val Gln Val Gly Arg Thr Leu Pro Leu
        115                 120                 125

Leu Thr Pro Met Ser Glu Val Ala Gly Arg Met Ala Ala Gln Ile Gly
    130                 135                 140

Ala Gln Phe Leu Glu Lys Pro Tyr Gly Gly Lys Gly Ile Leu Leu Gly
145                 150                 155                 160

Gly Val Pro Gly Val Ala Arg Gly Lys Val Thr Ile Ile Gly Gly Gly
                165                 170                 175

Val Val Gly Thr Asn Ala Ala Lys Val Ala Val Gly Leu Gly Ala Asp
            180                 185                 190

Val Thr Ile Ile Asp Leu Asn Ala Asp Arg Leu Arg Glu Leu Asp Asp
        195                 200                 205

Ile Phe Gly Asn Gln Ile Thr Thr Leu Met Ser Asn Pro Met Asn Ile
    210                 215                 220
```

```
Ala Glu Ala Val Ala Glu Ala Asp Leu Val Ile Gly Ala Val Leu Ile
225                 230                 235                 240

Pro Gly Ala Arg Ala Pro Lys Leu Val Thr Glu Asp Met Val Lys Ala
            245                 250                 255

Met Lys Pro Gly Ser Val Ile Val Asp Val Ala Ile Asp Gln Gly Gly
        260                 265                 270

Ile Val Glu Thr Ser Asp His Val Thr Thr His Asp Asp Pro Thr Tyr
    275                 280                 285

Val Lys His Gly Val Val His Tyr Ala Val Ala Asn Met Pro Gly Ala
290                 295                 300

Val Pro Arg Thr Ser Thr Ile Ala Leu Thr Asn Val Thr Met Pro Tyr
305                 310                 315                 320

Ala Leu Gln Ile Ala Asn Lys Gly Val Ile Gln Ala Ile Thr Asp Asn
            325                 330                 335

Pro Ala Leu Glu Leu Gly Val Asn Val Ala Asn Gly Glu Ile Thr Tyr
        340                 345                 350

Glu Ala Val Ala Arg Asp Leu Gly Tyr Arg Tyr Val Pro Ala Arg Glu
    355                 360                 365

Ala Leu Gly Lys Thr Leu Ala Ala Asn
    370                 375

<210> SEQ ID NO 35
<211> LENGTH: 369
<212> TYPE: PRT
<213> ORGANISM: Thermus thermophilus

<400> SEQUENCE: 35

Met Val Ile Gly Val Pro Lys Glu Ile Lys Thr Leu Glu Asn Arg Val
1               5                   10                  15

Ala Leu Thr Pro Gly Gly Val Glu Ser Leu Val Arg Arg Gly His Thr
            20                  25                  30

Val Leu Val Glu Arg Gly Ala Gly Glu Gly Ser Gly Leu Ser Asp Ala
        35                  40                  45

Glu Tyr Ala Arg Ala Gly Ala Glu Leu Val Gly Arg Glu Glu Ala Trp
    50                  55                  60

Gly Ala Glu Met Val Val Lys Val Lys Glu Pro Leu Pro Glu Glu Tyr
65                  70                  75                  80

Gly Phe Leu Arg Glu Gly Leu Ile Leu Phe Thr Tyr Leu His Leu Ala
                85                  90                  95

Ala Asp Arg Gly Leu Thr Glu Ala Met Leu Arg Ser Gly Val Thr Gly
            100                 105                 110

Ile Ala Tyr Glu Thr Val Gln Leu Pro Asp Gly Thr Leu Pro Leu Leu
        115                 120                 125

Val Pro Met Ser Glu Val Ala Gly Arg Met Ala Pro Gln Val Gly Ala
130                 135                 140

Gln Phe Leu Glu Lys Pro Lys Gly Gly Arg Gly Val Leu Leu Gly Gly
145                 150                 155                 160

Val Pro Gly Val Ala Pro Ala Ser Val Val Ile Leu Gly Gly Gly Thr
                165                 170                 175

Val Gly Thr Asn Ala Ala Lys Ile Ala Leu Gly Met Gly Ala Gln Val
            180                 185                 190

Thr Ile Leu Asp Val Asn His Lys Arg Leu Gln Tyr Leu Asp Asp Val
        195                 200                 205

Phe Gly Gly Arg Val Ile Thr Leu Thr Ala Thr Glu Ala Asn Ile Lys
```

```
            210                 215                 220
Lys Ser Val Gln His Ala Asp Leu Leu Ile Gly Ala Val Leu Val Pro
225                 230                 235                 240

Gly Ala Lys Ala Pro Lys Leu Val Thr Arg Asp Met Leu Ser Leu Met
                245                 250                 255

Lys Glu Gly Ala Val Ile Val Asp Val Ala Val Asp Gln Gly Gly Cys
                260                 265                 270

Val Glu Thr Ile Arg Pro Thr Thr His Ala Glu Pro Thr Tyr Val Val
            275                 280                 285

Asp Gly Val Val His Tyr Gly Val Ala Asn Met Pro Gly Ala Val Pro
        290                 295                 300

Arg Thr Ser Thr Phe Ala Leu Thr Asn Gln Thr Leu Pro Tyr Val Leu
305                 310                 315                 320

Lys Leu Ala Glu Lys Gly Leu Asp Ala Leu Glu Asp Ala Ala Leu
                325                 330                 335

Leu Lys Gly Leu Asn Thr His Lys Gly Arg Leu Thr His Pro Gly Val
                340                 345                 350

Ala Glu Ala Phe Gly Leu Pro Tyr Thr Pro Pro Glu Glu Ala Leu Arg
                355                 360                 365

Gly

<210> SEQ ID NO 36
<211> LENGTH: 345
<212> TYPE: PRT
<213> ORGANISM: Thermus thermophilus

<400> SEQUENCE: 36

Met Glu Phe Gly Val Pro Arg Glu Arg Ser Gly Gly Glu Ile Pro Glu
1               5                   10                  15

Arg Arg Val Pro Leu Thr Pro Gln Gly Val Arg Glu Leu Val Ala Ser
                20                  25                  30

Gly His Arg Val Tyr Val Glu Arg Gly Ala Gly Glu Gly Ala Gly Phe
            35                  40                  45

Pro Asp Glu Ala Tyr Glu Glu Ala Gly Ala Arg Leu Val Gly Arg Glu
        50                  55                  60

Glu Ala Phe Gly Arg Pro Gln Val Val Leu Lys Val Ala Arg Pro Thr
65                  70                  75                  80

Leu Glu Glu Val Gly Leu Met Arg Lys Asn Ala Val Leu Met Ala Phe
                85                  90                  95

Leu His Leu Ala Val Ala Glu Ser Pro Leu Val Glu Ala Met Ala Gln
            100                 105                 110

Lys Gly Leu Thr Ala Ile Gly Tyr Glu Leu Val Gly Glu Gly Arg
                115                 120                 125

Arg Pro Val Leu Lys Ala Met Ser Glu Ile Ala Gly Arg Met Ala Pro
        130                 135                 140

Gln Leu Ala Gly Arg Leu Leu Glu Ala Pro Gln Gly Pro Gly Ile Leu
145                 150                 155                 160

Leu Ser Gly Leu Val Gly Ile Pro Pro Ala Asp Val Val Leu Gly
                165                 170                 175

Ala Gly Val Leu Gly Arg Ala Ala Arg Ala Phe Leu Gly Ala Gly
            180                 185                 190

Ala Ser Val His Leu Leu Asp Arg Ala Leu Pro Pro Leu Glu Glu Ala
        195                 200                 205

Ala Arg Glu Ala Pro Gly Ala Ile Thr Ala Leu Val Thr Gln Asp Arg
```

```
                 210                 215                 220

Leu Glu Arg Tyr Val Ala Phe Ala Asp Val Leu Val Gly Ala Val Ala
225                 230                 235                 240

Val Pro Gly Glu Arg Thr Pro Leu Leu Leu Thr Arg Gly Leu Leu Ala
                245                 250                 255

Arg Met Arg Pro Gly Ser Val Leu Leu Asp Phe Ser Ile Asp Gln Gly
                260                 265                 270

Gly Val Ser Glu Thr Ser Arg Pro Gly Val Tyr Gln Glu Met Gly Val
            275                 280                 285

Thr His Phe Cys Leu Pro Asn Val Pro Ala Leu Val Pro Arg Thr Ala
            290                 295                 300

Ser His Ala Leu Thr Leu Thr Leu Leu Pro Tyr Leu Leu Arg Ile Gln
305                 310                 315                 320

Glu Asp Pro Leu Ala Leu Pro Gly Leu Arg Gln Gly Ala Tyr Leu Leu
                325                 330                 335

Phe Gly Glu Lys Gly Gly His Leu Glu
                340                 345
```

<210> SEQ ID NO 37
<211> LENGTH: 11
<212> TYPE: PRT
<213> ORGANISM: Artificial sequence
<220> FEATURE:
<223> OTHER INFORMATION: N-terminal portion of maltose-binding protein

<400> SEQUENCE: 37

```
Met Lys Ile Glu Glu Gly Lys Leu Val Ile His
1               5                   10
```

<210> SEQ ID NO 38
<211> LENGTH: 33
<212> TYPE: DNA
<213> ORGANISM: Artificial sequence
<220> FEATURE:
<223> OTHER INFORMATION: DNA coding N-terminal portion of maltose-
      binding protein

<400> SEQUENCE: 38
atgaaaatcg aagaaggtaa actggtaatc cat                                33

<210> SEQ ID NO 39
<211> LENGTH: 388
<212> TYPE: PRT
<213> ORGANISM: Artificial sequence
<220> FEATURE:
<223> OTHER INFORMATION: modified alanine dehydrogenase of Geobacillus
      stearothermophilus

<400> SEQUENCE: 39

```
Met Lys Ile Glu Glu Gly Lys Leu Val Ile His Met Ile Ile Gly Val
1               5                   10                  15

Pro Lys Glu Ile Lys Asn Asn Glu Asn Arg Val Ala Ile Thr Pro Ala
                20                  25                  30

Gly Val Leu Ser Phe Val Gln Ala Gly His Thr Val Leu Ile Glu Lys
            35                  40                  45

Glu Ala Gly Val Gly Ser Gly Phe Ser Asp Ser Asp Tyr Ala Arg Ala
        50                  55                  60

Gly Ala Gln Ile Ile Glu Arg Ala Glu Asp Val Trp Ala Gln Ala Asp
65                  70                  75                  80

Met Val Met Lys Val Lys Glu Pro Leu Pro Ser Glu Tyr Gly Tyr Phe
```

```
                    85                  90                  95
Arg Pro Gly Leu Ile Leu Phe Thr Tyr Leu His Leu Ala Ala Asp Pro
                100                 105                 110
Glu Leu Thr Arg Ala Leu Lys Glu Ser Gly Val Ile Ala Ile Ala Tyr
            115                 120                 125
Glu Thr Val Gln Val Gly Arg Thr Leu Pro Leu Leu Thr Pro Met Ser
        130                 135                 140
Glu Val Ala Gly Arg Met Ala Ala Gln Ile Gly Ala Gln Phe Leu Glu
145                 150                 155                 160
Lys Pro Tyr Gly Gly Lys Gly Ile Leu Gly Gly Val Pro Gly Val
                165                 170                 175
Ala Arg Gly Lys Val Thr Ile Ile Gly Gly Gly Val Val Gly Thr Asn
                180                 185                 190
Ala Ala Lys Val Ala Val Gly Leu Gly Ala Asp Val Thr Ile Ile Asp
            195                 200                 205
Leu Asn Ala Asp Arg Leu Arg Glu Leu Asp Asp Ile Phe Gly Asn Gln
        210                 215                 220
Ile Thr Thr Leu Met Ser Asn Pro Met Asn Ile Ala Glu Ala Val Ala
225                 230                 235                 240
Glu Ala Asp Leu Val Ile Gly Ala Val Leu Ile Pro Gly Ala Arg Ala
                245                 250                 255
Pro Lys Leu Val Thr Glu Asp Met Val Lys Ala Met Lys Pro Gly Ser
                260                 265                 270
Val Ile Val Asp Val Ala Ile Asp Gln Gly Gly Ile Val Glu Thr Ser
            275                 280                 285
Asp His Val Thr Thr His Asp Asp Pro Thr Tyr Val Lys His Gly Val
        290                 295                 300
Val His Tyr Ala Val Ala Asn Met Pro Gly Ala Val Pro Arg Thr Ser
305                 310                 315                 320
Thr Ile Ala Leu Thr Asn Val Thr Met Pro Tyr Ala Leu Gln Ile Ala
                325                 330                 335
Asn Lys Gly Val Ile Gln Ala Ile Thr Asp Asn Pro Ala Leu Glu Leu
                340                 345                 350
Gly Val Asn Val Ala Asn Gly Glu Ile Thr Tyr Glu Ala Val Ala Arg
            355                 360                 365
Asp Leu Gly Tyr Arg Tyr Val Pro Ala Arg Glu Ala Leu Gly Lys Thr
        370                 375                 380
Leu Ala Ala Asn
385

<210> SEQ ID NO 40
<211> LENGTH: 1167
<212> TYPE: DNA
<213> ORGANISM: Artificial sequence
<220> FEATURE:
<223> OTHER INFORMATION: DNA coding modified alanine dehydrogenase gene
      of Geobacillus stearothermophilus

<400> SEQUENCE: 40
atgaaaatcg aagaaggtaa actggtaatc catatgatta ttggagtgcc aaaggaaatc      60
aaaaataacg aaaaccgtgt cgccattacg ccggctggcg ttttgtcatt cgttcaggct     120
ggacatacgg ttctgattga aaagaggca ggggttggaa gcggtttcag cgacagcgat     180
tacgcccgtg ccggagcaca aatcatcgag cgggcggaag atgtttgggc gcaagccgat     240
atggtgatga agtgaaaga gccgctgcca agcgaatacg gctatttccg cccaggtctc     300
```

```
attttgttca cctatttgca tttggccgcc gacccggagt tgacacgcgc cttaaaagaa      360
agcggcgtca tcgccattgc ctatgagacg gtgcaagtcg ccgcacact gccgctgttg       420 acaccaatga gcgaagtcgc cggacggatg ccgcgcaaa ttggagcgca atttttagaa       480
aaaccgtacg gcggcaaagg catcttgctt ggcggcgtcc caggcgttgc ccgcggcaaa      540
gtgacgatca tcggcggcgg agtcgtcggc acgaacgcag cgaaagtcgc ggtcggcctc      600
ggggcagatg tcacgattat cgacttgaac gcggatcgcc tgcgcgagct tgacgacatt     660
ttcggcaacc aaattacgac gctcatgtcc aacccaatga acatcgccga agcggttgct      720
gaggccgacc ttgtcatcgg cgccgtcctc atcccgggag cgcgggcgcc gaagctcgtc      780
accgaggaca tggtgaaagc gatgaaaccg ggttcggtca tcgtcgatgt cgccatcgac      840 caaggggggca tcgtcgagac gagcgaccac gtcacgacac atgacgaccc gacgtacgtc     900
aaacacggcg tcgtccatta tgcggtcgcc aacatgcctg cgccgtccc gcgcacctca      960 acgatcgcct tgacgaacgt caccatgcca tacgccttgc aaatcgccaa caaaggcgtc     1020
atccaagcca ttacagacaa cccggcgctt gagcttggcg tcaacgtcgc caacggtgaa     1080
atcacgtacg aagcggtcgc ccgcgacctc ggttaccgct acgtcccggc ccgcgaagcg     1140
ctcgggaaaa cgttggccgc caactaa                                          1167

<210> SEQ ID NO 41
<211> LENGTH: 548
<212> TYPE: PRT
<213> ORGANISM: Lactococcus lactis

<400> SEQUENCE: 41

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
```

```
                210                 215                 220
Val Ser Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Lys Leu Ser Glu Pro Asn Leu Lys Glu Phe Val Glu Ser
                260                 265                 270

Ala Asp Phe Ile Leu Met Leu Gly Val Lys Leu Thr Asp Ser Ser Thr
                275                 280                 285

Gly Ala Phe Thr His His Leu Asn Glu Asn Lys Met Ile Ser Leu Asn
                290                 295                 300

Ile Asp Glu Gly Lys Ile Phe Asn Glu Ser Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
                340                 345                 350

Leu Leu Ser Gln Asp Arg Leu Trp Gln Ala Val Glu Asn Leu Thr Gln
                355                 360                 365

Ser Asn Glu Thr Ile Val Ala Glu Gln Gly Thr Ser Phe Phe Gly Ala
                370                 375                 380

Ser Ser Ile Phe Leu Lys Pro Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
                420                 425                 430

Gln Leu Thr Val Gln Glu Leu Gly Leu Ala Ile Arg Glu Lys Ile Asn
                435                 440                 445

Pro Ile Cys Phe Ile Ile Asn Asn Asp Gly Tyr Thr Val Glu Arg Glu
                450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Arg Val Val Ser
                485                 490                 495

Lys Ile Val Arg Thr Glu Asn Glu Phe Val Ser Val Met Lys Glu Ala
                500                 505                 510

Gln Ala Asp Pro Asn Arg Met Tyr Trp Ile Glu Leu Ile Leu Ala Lys
                515                 520                 525

Glu Asp Ala Pro Lys Val Leu Lys Lys Met Gly Lys Leu Phe Ala Glu
                530                 535                 540

Gln Asn Lys Ser
545

<210> SEQ ID NO 42
<211> LENGTH: 35
<212> TYPE: DNA
<213> ORGANISM: Artificial sequence
<220> FEATURE:
<223> OTHER INFORMATION: PCR primer

<400> SEQUENCE: 42
cgtggccaac taggcccagc cagatactcc cgatc                              35

<210> SEQ ID NO 43
```

```
<211> LENGTH: 35
<212> TYPE: DNA
<213> ORGANISM: Artificial sequence
<220> FEATURE:
<223> OTHER INFORMATION: PCR primer

<400> SEQUENCE: 43
tgaggcctca ttggccggag cgcaacccac tcact                                 35

<210> SEQ ID NO 44
<211> LENGTH: 35
<212> TYPE: DNA
<213> ORGANISM: Artificial sequence
<220> FEATURE:
<223> OTHER INFORMATION: PCR primer

<400> SEQUENCE: 44
ctgggcctag ttggccacgt agaaagccag tccgc                                 35

<210> SEQ ID NO 45
<211> LENGTH: 35
<212> TYPE: DNA
<213> ORGANISM: Artificial sequence
<220> FEATURE:
<223> OTHER INFORMATION: PCR primer

<400> SEQUENCE: 45
tccggccaat gaggcctcag aagaactcgt caaga                                 35

<210> SEQ ID NO 46
<211> LENGTH: 83
<212> TYPE: DNA
<213> ORGANISM: Artificial sequence
<220> FEATURE:
<223> OTHER INFORMATION: PCR primer

<400> SEQUENCE: 46
gcattaatcc ttggactcct gttgatagat ccagtaatga cctcagaact ccatctggat      60
ttgttcagaa cgctcggttg ccg                                              83

<210> SEQ ID NO 47
<211> LENGTH: 83
<212> TYPE: DNA
<213> ORGANISM: Artificial sequence
<220> FEATURE:
<223> OTHER INFORMATION: PCR primer

<400> SEQUENCE: 47
caccgtgcag tcgatggatc tggattctca ccaataaaaa acgcccggcg gcaaccgagc      60
gttctgaaca aatccagatg gag                                              83

<210> SEQ ID NO 48
<211> LENGTH: 50
<212> TYPE: DNA
<213> ORGANISM: Artificial sequence
<220> FEATURE:
<223> OTHER INFORMATION: PCR primer

<400> SEQUENCE: 48
ttattggtga gaatccagat ccatcgactg cacggtgcac caatgcttct                 50

<210> SEQ ID NO 49
<211> LENGTH: 70
<212> TYPE: DNA
<213> ORGANISM: Artificial sequence
```

<220> FEATURE:
<223> OTHER INFORMATION: PCR primer

<400> SEQUENCE: 49
gcaagcttgg agtgatcatc gtatgcatat gcgtttctcc tccagatccc tgtttcctgt    60
gtgaaattgt                                                           70

<210> SEQ ID NO 50
<211> LENGTH: 35
<212> TYPE: DNA
<213> ORGANISM: Artificial sequence
<220> FEATURE:
<223> OTHER INFORMATION: PCR primer

<400> SEQUENCE: 50
ctcgaattca ctggccgtcg ttttacaacg tcgtg                               35

<210> SEQ ID NO 51
<211> LENGTH: 35
<212> TYPE: DNA
<213> ORGANISM: Artificial sequence
<220> FEATURE:
<223> OTHER INFORMATION: PCR primer

<400> SEQUENCE: 51
cgcaattgag tttgtagaaa cgcaaaaagg ccatc                               35

<210> SEQ ID NO 52
<211> LENGTH: 35
<212> TYPE: DNA
<213> ORGANISM: Artificial sequence
<220> FEATURE:
<223> OTHER INFORMATION: PCR primer

<400> SEQUENCE: 52
gcacatatgt atacagtagg agattaccta ttaga                               35

<210> SEQ ID NO 53
<211> LENGTH: 35
<212> TYPE: DNA
<213> ORGANISM: Artificial sequence
<220> FEATURE:
<223> OTHER INFORMATION: PCR primer

<400> SEQUENCE: 53
gcaggatcct tatgatttat tttgttcagc aaata                               35

<210> SEQ ID NO 54
<211> LENGTH: 35
<212> TYPE: DNA
<213> ORGANISM: Artificial sequence
<220> FEATURE:
<223> OTHER INFORMATION: PCR primer

<400> SEQUENCE: 54
gcacatatga caaaagcaac aaaagaacaa aaatc                               35

<210> SEQ ID NO 55
<211> LENGTH: 35
<212> TYPE: DNA
<213> ORGANISM: Artificial sequence
<220> FEATURE:
<223> OTHER INFORMATION: PCR primer

<400> SEQUENCE: 55

```
gcaggatcct agagagcttt cgttttcatg agttc                              35

<210> SEQ ID NO 56
<211> LENGTH: 35
<212> TYPE: DNA
<213> ORGANISM: Artificial sequence
<220> FEATURE:
<223> OTHER INFORMATION: PCR primer

<400> SEQUENCE: 56
cgagtccata tgaaacagac tatccgcaat atcag                              35

<210> SEQ ID NO 57
<211> LENGTH: 35
<212> TYPE: DNA
<213> ORGANISM: Artificial sequence
<220> FEATURE:
<223> OTHER INFORMATION: PCR primer

<400> SEQUENCE: 57
gcaggatcct taccgagaat tcgagcgctt tcgca                              35

<210> SEQ ID NO 58
<211> LENGTH: 35
<212> TYPE: DNA
<213> ORGANISM: Artificial sequence
<220> FEATURE:
<223> OTHER INFORMATION: PCR primer

<400> SEQUENCE: 58
cgagtccata tgaaaaagcg ggtgatgcgt ggcct                              35

<210> SEQ ID NO 59
<211> LENGTH: 35
<212> TYPE: DNA
<213> ORGANISM: Artificial sequence
<220> FEATURE:
<223> OTHER INFORMATION: PCR primer

<400> SEQUENCE: 59
gcaggatcct catctgtctg acagtctcat cgtca                              35

<210> SEQ ID NO 60
<211> LENGTH: 35
<212> TYPE: DNA
<213> ORGANISM: Artificial sequence
<220> FEATURE:
<223> OTHER INFORMATION: PCR primer

<400> SEQUENCE: 60
cgagtccata tgcaaccgac ctacactatt gggga                              35

<210> SEQ ID NO 61
<211> LENGTH: 35
<212> TYPE: DNA
<213> ORGANISM: Artificial sequence
<220> FEATURE:
<223> OTHER INFORMATION: PCR primer

<400> SEQUENCE: 61
cgcggatcct taaacgcggc tgtttcgctc ctcaa                              35

<210> SEQ ID NO 62
<211> LENGTH: 35
<212> TYPE: DNA
<213> ORGANISM: Artificial sequence
```

```
<220> FEATURE:
<223> OTHER INFORMATION: PCR primer

<400> SEQUENCE: 62
cgagtccata tgaaggcagc tgttgttacc cacga        35

<210> SEQ ID NO 63
<211> LENGTH: 35
<212> TYPE: DNA
<213> ORGANISM: Artificial sequence
<220> FEATURE:
<223> OTHER INFORMATION: PCR primer

<400> SEQUENCE: 63
cgcgaattct tagctacgca gatcgataac catac        35

<210> SEQ ID NO 64
<211> LENGTH: 35
<212> TYPE: DNA
<213> ORGANISM: Artificial sequence
<220> FEATURE:
<223> OTHER INFORMATION: PCR primer

<400> SEQUENCE: 64
cgagtccata tgaaagccgc cgttgttcac aaatt        35

<210> SEQ ID NO 65
<211> LENGTH: 35
<212> TYPE: DNA
<213> ORGANISM: Artificial sequence
<220> FEATURE:
<223> OTHER INFORMATION: PCR primer

<400> SEQUENCE: 65
gcaggatcct tacattgtta aaacaatgcg gccat        35

<210> SEQ ID NO 66
<211> LENGTH: 35
<212> TYPE: DNA
<213> ORGANISM: Artificial sequence
<220> FEATURE:
<223> OTHER INFORMATION: PCR primer

<400> SEQUENCE: 66
cgagtccata tgaaagcggc agttgtcaac gattt        35

<210> SEQ ID NO 67
<211> LENGTH: 35
<212> TYPE: DNA
<213> ORGANISM: Artificial sequence
<220> FEATURE:
<223> OTHER INFORMATION: PCR primer

<400> SEQUENCE: 67
cgcgaattct taacggttga caccgatggt taaaa        35

<210> SEQ ID NO 68
<211> LENGTH: 35
<212> TYPE: DNA
<213> ORGANISM: Artificial sequence
<220> FEATURE:
<223> OTHER INFORMATION: PCR primer

<400> SEQUENCE: 68
cgagtccata tgaaagcact tacataccta gggcc        35
```

<210> SEQ ID NO 69
<211> LENGTH: 35
<212> TYPE: DNA
<213> ORGANISM: Artificial sequence
<220> FEATURE:
<223> OTHER INFORMATION: PCR primer

<400> SEQUENCE: 69
gcaggatcct taactgttgg aaataatgac tttta                    35

<210> SEQ ID NO 70
<211> LENGTH: 35
<212> TYPE: DNA
<213> ORGANISM: Artificial sequence
<220> FEATURE:
<223> OTHER INFORMATION: PCR primer

<400> SEQUENCE: 70
cgcggtaccg gatctggagg agaaacgcat atgaa                    35

<210> SEQ ID NO 71
<211> LENGTH: 35
<212> TYPE: DNA
<213> ORGANISM: Artificial sequence
<220> FEATURE:
<223> OTHER INFORMATION: PCR primer

<400> SEQUENCE: 71
cgcggtacct taacggttga caccgatggt taaaa                    35

<210> SEQ ID NO 72
<211> LENGTH: 35
<212> TYPE: DNA
<213> ORGANISM: Artificial sequence
<220> FEATURE:
<223> OTHER INFORMATION: PCR primer

<400> SEQUENCE: 72
gcacatatga cttatactgt cggacattat cttgc                    35

<210> SEQ ID NO 73
<211> LENGTH: 35
<212> TYPE: DNA
<213> ORGANISM: Artificial sequence
<220> FEATURE:
<223> OTHER INFORMATION: PCR primer

<400> SEQUENCE: 73
gcaggatcct tagacgctct ggggcttgcg ggagt                    35

<210> SEQ ID NO 74
<211> LENGTH: 35
<212> TYPE: DNA
<213> ORGANISM: Artificial sequence
<220> FEATURE:
<223> OTHER INFORMATION: PCR primer

<400> SEQUENCE: 74
cgagtccata tgaaggcagc tgttgttacc cacga                    35

<210> SEQ ID NO 75
<211> LENGTH: 35
<212> TYPE: DNA
<213> ORGANISM: Artificial sequence
<220> FEATURE:
<223> OTHER INFORMATION: PCR primer

<400> SEQUENCE: 75
cgcgtcgact tagctacgca gatcgataac catac                                   35

<210> SEQ ID NO 76
<211> LENGTH: 35
<212> TYPE: DNA
<213> ORGANISM: Artificial sequence
<220> FEATURE:
<223> OTHER INFORMATION: PCR primer

<400> SEQUENCE: 76
gcacatatgt ataccgttgg tatgtacttg gcaga                                   35

<210> SEQ ID NO 77
<211> LENGTH: 35
<212> TYPE: DNA
<213> ORGANISM: Artificial sequence
<220> FEATURE:
<223> OTHER INFORMATION: PCR primer

<400> SEQUENCE: 77
gcagtcgact tacgcttgtg gtttgcgaga gttgg                                   35

<210> SEQ ID NO 78
<211> LENGTH: 35
<212> TYPE: DNA
<213> ORGANISM: Artificial sequence
<220> FEATURE:
<223> OTHER INFORMATION: PCR primer

<400> SEQUENCE: 78
gcacatatga catatacagt cggcatgtat cttgc                                   35

<210> SEQ ID NO 79
<211> LENGTH: 35
<212> TYPE: DNA
<213> ORGANISM: Artificial sequence
<220> FEATURE:
<223> OTHER INFORMATION: PCR primer

<400> SEQUENCE: 79
gcagtcgact caggatacct gcggttttct ggaat                                   35

<210> SEQ ID NO 80
<211> LENGTH: 35
<212> TYPE: DNA
<213> ORGANISM: Artificial sequence
<220> FEATURE:
<223> OTHER INFORMATION: PCR primer

<400> SEQUENCE: 80
gcacatatgg ctgttactaa tgtcgctgaa cttaa                                   35

<210> SEQ ID NO 81
<211> LENGTH: 35
<212> TYPE: DNA
<213> ORGANISM: Artificial sequence
<220> FEATURE:
<223> OTHER INFORMATION: PCR primer

<400> SEQUENCE: 81
gcaggatcct taagcggatt ttttcgcttt tttct                                   35

<210> SEQ ID NO 82

```
<211> LENGTH: 35
<212> TYPE: DNA
<213> ORGANISM: Artificial sequence
<220> FEATURE:
<223> OTHER INFORMATION: PCR primer

<400> SEQUENCE: 82
gcacatatga cgaaaatagc gaataaatac gaagt                              35

<210> SEQ ID NO 83
<211> LENGTH: 35
<212> TYPE: DNA
<213> ORGANISM: Artificial sequence
<220> FEATURE:
<223> OTHER INFORMATION: PCR primer

<400> SEQUENCE: 83
gcactgcagt tatttcttcg cacctccgta ataag                              35

<210> SEQ ID NO 84
<211> LENGTH: 35
<212> TYPE: DNA
<213> ORGANISM: Artificial sequence
<220> FEATURE:
<223> OTHER INFORMATION: PCR primer

<400> SEQUENCE: 84
gaagctggcg ctgcgcttta tggatatccg taaac                              35

<210> SEQ ID NO 85
<211> LENGTH: 35
<212> TYPE: DNA
<213> ORGANISM: Artificial sequence
<220> FEATURE:
<223> OTHER INFORMATION: PCR primer

<400> SEQUENCE: 85
tcgaagtgag tttccggatg ttcgtacata accca                              35

<210> SEQ ID NO 86
<211> LENGTH: 35
<212> TYPE: DNA
<213> ORGANISM: Artificial sequence
<220> FEATURE:
<223> OTHER INFORMATION: PCR primer

<400> SEQUENCE: 86
atggcaatga gatttatgga tataagaaag agagt                              35

<210> SEQ ID NO 87
<211> LENGTH: 35
<212> TYPE: DNA
<213> ORGANISM: Artificial sequence
<220> FEATURE:
<223> OTHER INFORMATION: PCR primer

<400> SEQUENCE: 87
gttcataaag tcaacttccg gatgttcata catca                              35

<210> SEQ ID NO 88
<211> LENGTH: 35
<212> TYPE: DNA
<213> ORGANISM: Artificial sequence
<220> FEATURE:
<223> OTHER INFORMATION: PCR primer

<400> SEQUENCE: 88
```
cgcggtaccg gatctggagg agaaacgcat atgaa                              35

<210> SEQ ID NO 89
<211> LENGTH: 35
<212> TYPE: DNA
<213> ORGANISM: Artificial sequence
<220> FEATURE:
<223> OTHER INFORMATION: PCR primer

<400> SEQUENCE: 89
cgcggtacct taacggttga caccgatggt taaaa                              35

<210> SEQ ID NO 90
<211> LENGTH: 35
<212> TYPE: DNA
<213> ORGANISM: Artificial sequence
<220> FEATURE:
<223> OTHER INFORMATION: PCR primer

<400> SEQUENCE: 90
tccggcgggc atatgaagat cggcattcca aaaga                              35

<210> SEQ ID NO 91
<211> LENGTH: 35
<212> TYPE: DNA
<213> ORGANISM: Artificial sequence
<220> FEATURE:
<223> OTHER INFORMATION: PCR primer

<400> SEQUENCE: 91
aagaattcca gcggctcata tacgataccg ttcgg                              35

<210> SEQ ID NO 92
<211> LENGTH: 35
<212> TYPE: DNA
<213> ORGANISM: Artificial sequence
<220> FEATURE:
<223> OTHER INFORMATION: PCR primer

<400> SEQUENCE: 92
tccggcgggc atatgattat tggagtgcca aagga                              35

<210> SEQ ID NO 93
<211> LENGTH: 35
<212> TYPE: DNA
<213> ORGANISM: Artificial sequence
<220> FEATURE:
<223> OTHER INFORMATION: PCR primer

<400> SEQUENCE: 93
aagaattctt agttggcagc caacgttttc ccgag                              35

<210> SEQ ID NO 94
<211> LENGTH: 35
<212> TYPE: DNA
<213> ORGANISM: Artificial sequence
<220> FEATURE:
<223> OTHER INFORMATION: PCR primer

<400> SEQUENCE: 94
ccggcgggca tatggtgatc ggcgtgccga aggag                              35

<210> SEQ ID NO 95
<211> LENGTH: 35
<212> TYPE: DNA

```
<213> ORGANISM: Artificial sequence
<220> FEATURE:
<223> OTHER INFORMATION: PCR primer

<400> SEQUENCE: 95
aagaattctc accccctcaa ggcctcctcg ggagg                              35

<210> SEQ ID NO 96
<211> LENGTH: 35
<212> TYPE: DNA
<213> ORGANISM: Artificial sequence
<220> FEATURE:
<223> OTHER INFORMATION: PCR primer

<400> SEQUENCE: 96
cggcgggcat atggagttcg gcgtgcccag agaac                              35

<210> SEQ ID NO 97
<211> LENGTH: 35
<212> TYPE: DNA
<213> ORGANISM: Artificial sequence
<220> FEATURE:
<223> OTHER INFORMATION: PCR primer

<400> SEQUENCE: 97
aagaattctc attctaggtg gcctcctttc tcgcc                              35

<210> SEQ ID NO 98
<211> LENGTH: 33
<212> TYPE: DNA
<213> ORGANISM: Artificial sequence
<220> FEATURE:
<223> OTHER INFORMATION: PCR primer

<400> SEQUENCE: 98
tatgaaaatc gaagaaggta aactggtaat cca                                33

<210> SEQ ID NO 99
<211> LENGTH: 33
<212> TYPE: DNA
<213> ORGANISM: Artificial sequence
<220> FEATURE:
<223> OTHER INFORMATION: PCR primer

<400> SEQUENCE: 99
tatggattac cagtttacct tcttcgattt tca                                33

<210> SEQ ID NO 100
<211> LENGTH: 6
<212> TYPE: PRT
<213> ORGANISM: Artificial sequence
<220> FEATURE:
<223> OTHER INFORMATION: Polypeptide written by Journal of Bioscience
      and Bioengineering, 123, 540-546 (2017)

<400> SEQUENCE: 100

Met Ser Lys Ile Lys His
1               5

<210> SEQ ID NO 101
<211> LENGTH: 18
<212> TYPE: DNA
<213> ORGANISM: Artificial sequence
<220> FEATURE:
<223> OTHER INFORMATION: PCR primer

<400> SEQUENCE: 101
```
tatgagcaag atcaaaca                                            18

<210> SEQ ID NO 102
<211> LENGTH: 18
<212> TYPE: DNA
<213> ORGANISM: Artificial sequence
<220> FEATURE:
<223> OTHER INFORMATION: PCR primer

<400> SEQUENCE: 102
tatgtttgat cttgctca                                            18

<210> SEQ ID NO 103
<211> LENGTH: 11
<212> TYPE: PRT
<213> ORGANISM: Artificial sequence
<220> FEATURE:
<223> OTHER INFORMATION: N-terminal portion of glutathione S-transferase

<400> SEQUENCE: 103

Met Asp Phe Pro Val Ala Glu Asp Arg Arg His
1               5                   10

<210> SEQ ID NO 104
<211> LENGTH: 33
<212> TYPE: DNA
<213> ORGANISM: Artificial sequence
<220> FEATURE:
<223> OTHER INFORMATION: PCR primer

<400> SEQUENCE: 104
tatgtcgccg atcctcggct actggaaaat cca                           33

<210> SEQ ID NO 105
<211> LENGTH: 33
<212> TYPE: DNA
<213> ORGANISM: Artificial sequence
<220> FEATURE:
<223> OTHER INFORMATION: PCR primer

<400> SEQUENCE: 105
tatggatttt ccagtagccg aggatcggcg aca                           33

<210> SEQ ID NO 106
<211> LENGTH: 11
<212> TYPE: PRT
<213> ORGANISM: Artificial sequence
<220> FEATURE:
<223> OTHER INFORMATION: N-terminal portion of beta-glucosidase

<400> SEQUENCE: 106

Met Thr Glu Asn Ala Glu Lys Phe Leu Trp His
1               5                   10

<210> SEQ ID NO 107
<211> LENGTH: 33
<212> TYPE: DNA
<213> ORGANISM: Artificial sequence
<220> FEATURE:
<223> OTHER INFORMATION: PCR primer

<400> SEQUENCE: 107
tatgaccgag aacgccgaaa aattcctttg gca                           33

<210> SEQ ID NO 108

```
<211> LENGTH: 33
<212> TYPE: DNA
<213> ORGANISM: Artificial sequence
<220> FEATURE:
<223> OTHER INFORMATION: PCR primer

<400> SEQUENCE: 108
tatgccaaag gaatttttcg gcgttctcgg tca                                33

<210> SEQ ID NO 109
<211> LENGTH: 22
<212> TYPE: PRT
<213> ORGANISM: Artificial sequence
<220> FEATURE:
<223> OTHER INFORMATION: HAT sequence

<400> SEQUENCE: 109

Met Gly Lys Asp His Leu Ile His Asn Val His Lys Glu Glu His Ala
1               5                   10                  15

His Ala His Asn Lys His
            20

<210> SEQ ID NO 110
<211> LENGTH: 45
<212> TYPE: DNA
<213> ORGANISM: Artificial sequence
<220> FEATURE:
<223> OTHER INFORMATION: PCR primer

<400> SEQUENCE: 110
cgcatatggg caaggatcat ctcatccaca atgtccacaa agagg                   45

<210> SEQ ID NO 111
<211> LENGTH: 45
<212> TYPE: DNA
<213> ORGANISM: Artificial sequence
<220> FEATURE:
<223> OTHER INFORMATION: PCR primer

<400> SEQUENCE: 111
cgcatatgct tgttgtgggc atgagcgtgc tcctctttgt ggaca                   45
```

GENUS *HYDROGENOPHILUS* BACTERIUM TRANSFORMANT

TECHNICAL FIELD

The present invention relates to a genus *Hydrogenophilus* bacterium transformant having an ability to produce isobutanol, ethanol, or alanine, and to a method for producing isobutanol, ethanol, or alanine using the same.

BACKGROUND ART

Sequence Listing Submission Via EFS-Web

A computer readable text file, entitled "SequenceListing.txt," created on or about Oct. 13, 2020 with a file size of about 173 kb contains the sequence listing for this application and is hereby incorporated by reference in its entirety.
Production of Chemical Products Using Microorganisms Paris Agreement that was adopted in 2015, provides that global emissions of greenhouse gas should be promptly reduced. Under the Paris Agreement, Japan has set a goal of reducing emissions of greenhouse gas such as carbon dioxide and methane by 26% by the year 2030, in comparison with those of the year 2013.

Worldwide, majority of the production of chemical products depends on petroleum sources, and there is the problem of increase in greenhouse gas emissions. Accordingly, departure from petroleum dependency is required in the production of chemical products, and research and development of biorefineries that produce green chemical products from biomass is being strenuously carried out in various countries. However, the conversion of biomass into saccharides to be used as raw materials of microbial fermentation requires complex processes, and there is an issue of high cost.

As part of a research to depart from petroleum dependency, gases such as carbon dioxide, methane, and carbon monoxide have attracted attention as carbon sources having a higher degree of sustainability, and techniques for producing valuable chemical products and biofuels using microorganisms that utilize these gases are being a subject of interest. In particular, fixation and effective utilization of carbon dioxide, which is known for its high contribution to warming, is highly anticipated.
Production of Isobutanol Ethanol, n-butanol, and isobutanol have been used conventionally as biofuels, and methods for efficiently producing the compounds have been required. Some merits of butanol, which has 4 carbon atoms, are that it has a higher fuel efficiency as compared to that of ethanol having 2 carbon atoms, that it can be easily mixed with gasoline (carbon atoms 4 to 10) or diesel engines enabling the use of existing engines and fueling facilities as they are, and that facilities are less likely to corrode since butanol absorbs only a small amount of water in the air. In particular, there is a certified ASTM standard for isobutanol as a raw material of drop-in type biojet fuel. Technical development for practical application of isobutanol has been conducted as an effort to reduce carbon dioxide emission in the field of aviation.

Yeast and some bacteria produce a small amount of isobutanol. Isobutanol is produced from 2-ketoisovalerate, which is a metabolic intermediate in the biosynthetic pathway of essential amino acid valine. Isobutanol is produced via 5 steps from pyruvic acid, which is an important metabolite in a living body. Namely, acetolactate is produced from pyruvic acid by the catalytic action of acetohydroxy acid synthase, then 2,3-dihydroxyisovalerate is produced from acetolactate by the catalytic action of acetohydroxy acid isomeroreductase, then 2-ketoisovalerate is produced from 2,3-dihydroxyisovalerate by the catalytic action of dihydroxy acid dehydratase, then isobutyraldehyde is produced from 2-ketoisovalerate by the catalytic action of 2-keto-acid decarboxylase (hereinafter, may be referred to as "KDC") (EC 4.1.1.1), and finally, isobutanol is produced from isobutyraldehyde by the catalytic action of alcohol dehydrogenase (hereinafter, may be referred to as "ADH") (EC 1.1.1.1).

As a technique for producing isobutanol using a recombinant microorganism, Patent Document 1 discloses a method for producing isobutanol using a *Corynebacterium glutamicum* transformant. The transformat has exogenous genes of the above-described 5 enzymes that respectively catalyze the 5 steps that compose the metabolic pathway from pyruvic acid to isobutanol. *Lactococcus lactis* kivD gene or *Staphylococcus epidermidis* ipd gene is used as a 2-keto-acid decarboxylase gene, and *Saccharomyces cerevisiae* adh2 gene, *Pseudomonas putida* adh gene, or *Escherichia coli* adhP gene is used as an alcohol dehydrogenase gene.

In addition, various methods are known for producing isobutanol using transformants into which only a 2-keto-acid decarboxylase gene and an alcohol dehydrogenase gene are introduced.

Non-patent Document 1 teaches the use of a transformant obtained by introducing *Lactococcus lactis* kivD gene and *Saccharomyces cerevisiae* adh2 gene into *Escherichia coli*.

Non-patent Document 2 teaches the use of a transformant obtained by introducing *Lactococcus lactis* kivD gene and *Lactococcus lactis* adhA gene into *Escherichia coli*.

Non-patent Document 3 teaches the use of a transformant obtained by introducing *Lactococcus lactis* kivD gene and *Saccharomyces cerevisiae* adh2 gene into *Bacillus subtilis*.

Non-patent Document 4 teaches the use of a transformant obtained by introducing *Lactococcus lactis* kivD gene and *Ralstonia eutropha* adh gene into *Shewanella oneidensis*.

Non-patent Document 5 teaches the use of a transformant obtained by introducing *Lactococcus lactis* kivD gene and *Escherichia coli* yqhD gene into the cyanobacterium *Synechococcus elongatus*.

Non-patent Document 6 teaches the use of a transformant obtained by introducing a plasmid for overexpressing *Lactococcus lactis* kivD gene and *Ralstonia eutropha* adh gene into *Ralstonia eutropha*.

Non-patent Document 7 teaches the use of a transformant obtained by introducing a plasmid for overexpressing *Lactococcus lactis* kivD gene and *Geobacillus thermoglucosidasius* adhA gene into *Geobacillus thermoglucosidasius*.

Methods are also known in which, *Bacillus subtilis* alsS gene, *Geobacillus thermoglucosidasius* Geoth 3495 gene, *Geobacillus thermodenitrificans* Gtng_0348 gene, *Klebsiella pneumoniae* ipdC gene, or *Staphylococcus epidermidis* ipd gene is used as a 2-keto-acid decarboxylase gene besides a method in which *Lactococcus lactis* kivD gene is used. However, *Lactococcus lactis* kivD gene generally brings about higher enzyme activity within the host than the former 5 genes, and therefore, *Lactococcus lactis* kivD gene has been mainly used conventionally.

Almost all of the above-described methods are methods for producing isobutanol using sugar as a carbon source, and not methods for producing isobutanol using carbon dioxide as a carbon source.

The method of Non-patent Document 5 uses Cyanobacterium, which is a photosynthetic bacterium, as a host. The method is for producing isobutanol using sodium hydrogen carbonate as a carbon source. Cyanobacteria have a higher carbon dioxide fixation ability as compared to that of plants. However, the method of using Cyanobacterium as a host has not been put into practical use as an industrial method for producing isobutanol since carbon dioxide fixation ability of Cyanobacteria is insufficient.

Production of Ethanol

Conventionally, much of the ethanol used for fuels, chemical raw materials, beverages, and the like, has been manufactured by fermenting starch or saccharides derived from various biomass resources using microorganisms.

As methods for producing ethanol using a recombinant microorganism, methods which use transformants obtained by introducing a gene of pyruvate decarboxylase (hereinafter may be referred to as "PDC") (EC 4.1.1.1), which catalyzes the reaction of producing acetaldehyde by decarboxylating pyruvic acid, and/or introducing a gene of alcohol dehydrogenase (hereinafter may be referred to as "ADH") (EC 1.1.1.1), which catalyzes the reaction from acetaldehyde to ethanol, are known.

Many of the conventional methods use a transformant obtained by introducing a gene that produces PDC and a gene that produces ADH, both derived from *Zymomonas mobilis*. For example, Patent Document 2 teaches that a transformant obtained by introducing pdc gene and adhB gene, both derived from *Zymomonas mobilis*, into an enteric bacterium such as *Escherichia coli*, produces ethanol efficiently.

As a method that utilizes PDC and ADH genes of other bacteria, Non-patent Document 8 discloses a method for producing ethanol using a transformant obtained by introducing *Sarcina ventriculi* pdc gene and *Lactobacillus brevis* adh gene into *Escherichia coli*.

In addition, Non-patent Document 9 discloses a method for producing ethanol using a transformant obtained by introducing *Sarcina ventriculi* pdc gene and *Geobacillus stearothermophilus* adh gene into *Bacillus megaterium*.

Other than the pyruvate decarboxylase genes described above, pyruvate decarboxylase genes of *Gluconobacter oxydans*, *Gluconoacetobacter diazotrophicus*, *Acetobacter pasteurianus*, *Clostridium acetobutylicum*, and *Zymobacter palmae* are known to be utilized. Furthermore, other than the alcohol dehydrogenase genes described above, alcohol dehydrogenase genes of various microbial species are known to be utilized.

However, the methods described in those literatures are methods for producing ethanol using sugar as a carbon source, and not a method for producing ethanol using carbon dioxide as a carbon source.

As methods for producing ethanol using carbon dioxide as a carbon source, methods in which cyanobacterium, a photosynthetic bacterium, is used as a host, are known. For example, Non-patent Document 10 discloses a method for producing ethanol using a transformant obtained by introducing pdc and adhB genes derived from *Zymomonas mobilis* into a bacterium of the genus *Synechococcus*.

In addition, Non-patent Document 11 discloses a method for producing ethanol using a transformant obtained by introducing *Zymomonas mobilis* pdc gene and the NADPH-dependent ADH gene (slr1192) of bacteria of the genus *Synechocystis*, into a bacterium of the genus *Synechococcus*.

As mentioned above, the carbon dioxide fixation ability of Cyanobacteria is insufficient for industrial utilization, and therefore, no methods for using Cyanobacterium as a host has been put into practical use as a method for industrial production of ethanol.

Furthermore, as methods for producing ethanol using a recombinant microorganism, methods using transformants obtained by introducing a gene of aldehyde-alcohol dehydrogenase, which catalyzes the reaction of producing ethanol from acetyl-CoA via acetaldehyde, are also known.

The reaction of producing ethanol from acetyl-CoA via acetaldehyde is important for ethanol production under anaerobic conditions, and thus the aldehyde-alcohol dehydrogenase gene is generally used when producing alcohol using a microorganism that grows under anaerobic conditions, as a host.

For example, Non-patent Document 12 teaches a method for producing ethanol using a transformant obtained by introducing adhE gene, which is an aldehyde-alcohol dehydrogenase gene, into *Pyrococcus furiosus*, which grows under anaerobic conditions.

In addition, Non-patent Document 13 teaches a method for producing ethanol using a transformant obtained by introducing adhE gene into *Caldicellulosiruptor bescii*, which grows under anaerobic conditions.

However, these methods described in those literatures are methods for producing ethanol using sugar as a carbon source, and not a method for producing ethanol using carbon dioxide as a carbon source.

Production of Alanine

Alanine is an amino acid that is important as a raw material for medicine, food, or in chemical industry, and there is an increasing demand for alanine. Alanine dehydrogenase (EC 1.4.1.1) has been utilized for the production of alanine. This enzyme catalyzes the reaction of producing alanine from pyruvic acid, ammonia, and NADH.

As a technique to produce alanine using a microorganism, Non-patent Document 14 teaches a method for producing alanine using a transformant obtained by introducing the alanine dehydrogenase gene of *Bacillus stearothermophilus* (currently referred to as *Geobacillus stearothermophilus*) into *Escherichia coli*.

Patent Document 3 teaches a method for producing alanine using a transformant obtained by introducing the alanine dehydrogenase gene of bacteria of the genus *Arthrobacter*, into a bacterium of the genus *Escherichia*, genus *Corynebacterium*, or genus *Brevibacterium*.

Non-patent Document 15 teaches a method for producing alanine using a transformant obtained by introducing the alanine dehydrogenase gene of *Bacillus sphaericus* (currently referred to as *Lysinibacillus sphaericus*) into *Escherichia coli*.

Non-patent Document 16 teaches a method for producing alanine using a transformant obtained by introducing the alanine dehydrogenase gene of *Bacillus sphaericus* (currently referred to as *Lysinibacillus sphaericus*) into *Zymomonas mobilis*.

Non-patent Document 17 teaches a method for producing alanine using a transformant obtained by introducing the alanine dehydrogenase gene of *Bacillus sphaericus* (currently referred to as *Lysinibacillus sphaericus*) into *Lactococcus lactis*.

Non-patent Document 18 teaches a method for producing alanine using a transformant obtained by introducing the alanine dehydrogenase gene of *Bacillus sphaericus* (currently referred to as *Lysinibacillus sphaericus*) into *Corynebacterium glutamicum*.

However, all of the above-described methods are methods for producing alanine using sugar as a carbon source, and not methods for producing alanine using carbon dioxide as a carbon source.

CITATION LIST

Patent Documents

[Patent Document 1] WO/2010/113832
[Patent Document 2] WO/2001/96573
[Patent Document 3] JP1994(Heisei 6)-277082A

Non-Patent Documents

[Non-patent Document 1] Non-fermentative pathways for synthesis of branched-chain higher alcohols as biofuels. Atsumi S, Hanai T, Liao J C. Nature (2008) 451:86-89

[Non-patent Document 2] Engineering the isobutanol biosynthetic pathway in *Escherichia coli* by comparison of three aldehyde reductase/alcohol dehydrogenase genes. Atsumi S, Wu T Y, Eckl E M, Hawkins S D, Buelter T, Liao J C. Appl. Microbiol. Biotechnol. (2010) 85:651-657

[Non-patent Document 3] Engineering *Bacillus subtilis* for isobutanol production by heterologous Ehrlich pathway construction and the biosynthetic 2-ketoisovalerate precursor pathway overexpression. Li S, Wen J, Jia X. Appl. Microbiol. Biotechnol. (2011) 91:577-589

[Non-patent Document 4] Isobutanol production from an engineered *Shewanella oneidensis* MR-1. Jeon J M, Park H, Seo H M, Kim J H, Bhatia S K, Sathiyanarayanan G, Song H S, Park S H, Choi K Y, Sang B I, Yang Y H. Bioprocess Biosyst. Eng. (2015) 38:2147-2154

[Non-patent Document 5] Direct photosynthetic recycling of carbon dioxide to isobutyraldehyde. Atsumi S, Higashide W, Liao J C. Nat. Biotechnol. (2009) 27:1177-1180

[Non-patent Document 6] Studies on the production of branched-chain alcohols in engineered *Ralstonia eutropha*. Lu J, Brigham C J, Gai C S, Sinskey A J. Appl. Microbiol. Biotechnol. (2012) 96:283-297

[Non-patent Document 7] Isobutanol production at elevated temperatures in thermophilic *Geobacillus thermoglucosidasius*. Lin P P, Rabe K S, Takasumi J L, Kadisch M, Arnold F H, Liao J C. Metab. Eng. (2014) 24:1-8

[Non-patent Document 8] Coexpression of pyruvate decarboxylase and alcohol dehydrogenase genes in *Lactobacillus brevis*. Liu S, Dien B S, Nichols N N, Bischoff K M, Hughes S R, Cotta M A. FEMS Microbiol. Lett. (2007) 274:291-297

[Non-patent Document 9] Construction and expression of an ethanol production operon in Gram-positive bacteria. Talarico L A, Gil M A, Yomano L P, Ingram L O, Maupin-Furlow J A. Microbiology (2005) 151:4023-4031

[Non-patent Document 10] Ethanol synthesis by genetic engineering in cyanobacteria. Deng M D, Coleman J R. Appl. Environ. Microbiol. (1999) 65:523-528

[Non-patent Document 11] Combinatory strategy for characterizing and understanding the ethanol synthesis pathway in cyanobacteria cell factories. Luan G, Qi Y, Wang M, Li Z, Duan Y, Tan X, Lu X, Biotechnol. Biofuels (2015) 8:184

[Non-patent Document 12] Ethanol production by the hyperthermophilic archaeon *Pyrococcus furiosus* by expression of bacterial bifunctional alcohol dehydrogenases. Keller M W, Lipscomb G L, Nguyen D M, Crowley A T, Schut G J, Scott I, Kelly R M, Adams M W W. Microb. Biotechnol. (2017) 10:1535-1545

[Non-patent Document 13] Cellulosic ethanol production via consolidated bioprocessing at 75° C. by engineered *Caldicellulosiruptor bescii*. Chung D, Cha M, Snyder E N, Elkins J G, Guss A M, Westpheling J. Biotechnol. Biofuels (2015) 8:163

[Non-patent Document 14] Alanine production in an H+-ATPase- and lactate dehydrogenase-defective mutant of *Escherichia coli* expressing alanine dehydrogenase. Wada M, Narita K, Yokota A. Appl. Microbiol. Biotechnol. (2007) 76:819-825

[Non-patent Document 15] Aerobic production of alanine by *Escherichia coli* aceF ldhA mutants expressing the *Bacillus sphaericus* alaD gene. Lee M, Smith G M, Eiteman M A, Altman E. Appl. Microbiol. Biotechnol. (2004) 65:56-60

[Non-patent Document 16] Expression of an L-alanine dehydrogenase gene in *Zymomonas mobilis* and excretion of L-alanine. Uhlenbusch I, Sahm H, Sprenger G A. Appl. Environ. Microbiol. (1991) 57:1360-1366

[Non-patent Document 17] Conversion of *Lactococcus lactis* from homolactic to homoalanine fermentation through metabolic engineering. Hols P, Kleerebezem M, Schanck A N, Ferain T, Hugenholtz J, Delcour J, de Vos W M. Nat. Biotechnol. (1999) 17:588-592

[Non-patent Document 18] Engineering of sugar metabolism of *Corynebacterium glutamicum* for production of amino acid L-alanine under oxygen deprivation. Jojima T, Fujii M, Mori E, Inui M, Yukawa H. Appl. Microbiol. Biotechnol. (2010) 87:159-165

SUMMARY OF INVENTION

Technical Problem

The first object of the present invention is to provide a transformant of a bacterium of the genus *Hydrogenophilus* that is capable of efficiently producing isobutanol utilizing carbon dioxide as a sole carbon source, a method for efficiently producing isobutanol using this transformant, and a gene that enables the highly efficient production of isobutanol by bacteria of the genus *Hydrogenophilus*.

The second object of the present invention is to provide a transformant of a bacterium of the genus *Hydrogenophilus* that is capable of efficiently producing ethanol utilizing carbon dioxide as a sole carbon source, and a method for efficiently producing ethanol using this transformant.

The third object of the present invention is to provide a transformant of a bacterium of the genus *Hydrogenophilus* that is capable of efficiently producing alanine utilizing carbon dioxide as a sole carbon source, a method for efficiently producing alanine using this transformant, and a gene that enables highly efficient production of alanine by bacteria of the genus *Hydrogenophilus*.

Solution to Problem

The inventors of the present invention have carried out intensive studies in order to achieve the objects described above and have found the followings.

Compatibility Between Host and Gene

Bacteria of the genus *Hydrogenophilus* are hydrogen oxidizing bacteria which grow by producing organic substances from carbon dioxide by utilizing hydrogen energy. The growth rate of hydrogen oxidizing bacteria is generally extremely slow, however, the growth rate of bacteria of the genus *Hydrogenophilus* is fast, and their carbon dioxide fixation ability is remarkably higher than that of plants and photosynthetic bacteria. Bacteria of the genus *Hydrogenophilus* do not originally produce isobutanol or ethanol, and therefore, there is a need to introduce gene(s) of enzyme(s) that catalyze(s) the reaction of producing these compounds in order to provide the bacteria with the ability to produce these compounds. In addition, bacteria of the genus *Hydrogenophilus* produce alanine, however, in order to provide them with an ability to produce alanine at an industrial scale, there is a need to introduce gene(s) of enzyme(s) that catalyze(s) the reaction of producing alanine.

However, when a heterologous gene having natural base sequence is introduced into bacteria of the genus *Hydrogenophilus* using a vector that functions within the bacteria, a functioning protein often is not produced or insufficiently produced.

Production of Isobutanol (i) Bacteria of genus *Hydrogenophilus* originally do not produce isobutanol, and do not have a 2-keto-acid decarboxylase gene. Even when *Lactococcus lactis* kivD gene, *Bacillus subtilis* alsS gene, *Geobacillus thermoglucosidasius* Geoth 3495 gene, *Geobacillus thermodenitrificans* Gtng 0348 gene, or *Klebsiella pneumoniae* ipdC gene is introduced into bacteria of the genus *Hydrogenophilus* as a 2-keto-acid decarboxylase gene, they do not function within the genus *Hydrogenophilus* bacteria. In particular, *Lactococcus lactis* kivD gene functions and brings about high activity within various hosts, and thus is frequently used in methods for producing isobutanol, however, it does not function within bacteria of the genus *Hydrogenophilus*. Thus, when a heterologous gene is introduced into bacteria of the genus *Hydrogenophilus* using a vector that functions within the bacteria, a functioning protein often is not produced or insufficiently produced.

With regard to this point, the inventors of the present invention have accumulated data on whether or not genes derived from various microorganisms are expressed in bacteria of the genus *Hydrogenophilus*. By further advancing this accumulation of information and systematizing it, the codon usage of *Lactococcus lactis* kivD gene was optimized so that it was conformed to the frequency of codon usage of bacteria of the genus *Hydrogenophilus*. As a result, the inventors of the present invention have succeeded in producing a highly active 2-keto-acid decarboxylase by introducing the codon-optimized kivD gene which consists of a base sequence of SEQ ID NO: 1 into bacteria of the genus *Hydrogenophilus*.

(ii) Bacteria of the genus *Hydrogenophilus* originally do not produce isobutanol, and do not have an alcohol dehydrogenase gene.

However, when an alcohol dehydrogenase gene of a heterogenous microorganism is introduced into bacteria of the genus *Hydrogenophilus*, the gene functions in the genus *Hydrogenophilus* bacteria and a highly active alcohol dehydrogenase is produced. In particular, when *Klebsiella pneumoniae* adhP gene, *Geobacillus thermocatenulatus* adhP gene, or *Geobacillus thermoglucosidasius* adhA or adhP gene is introduced into bacteria of the genus *Hydrogenophilus*, a particularly highly active alcohol dehydrogenase is produced.

(iii) A transformant obtained by introducing the codon-optimized 2-keto-acid decarboxylase gene described in (i) above, and an alcohol dehydrogenase gene into a bacterium of the genus *Hydrogenophilus*, efficiently produces isobutanol using carbon dioxide as a sole carbon source.

Production of Ethanol

First Transformant Having Ethanol Producing Ability (i) Bacteria of the genus *Hydrogenophilus* originally do not produce ethanol, and do not have a pyruvate decarboxylase gene. Even when the pdc gene of *Zymomonas mobilis*, *Zymobacter palmae* or *Acetobacter* pasteurianus, which has been reported to produce ethanol, is introduced into bacteria of the genus *Hydrogenophilus* as a pyruvate decarboxylase gene, the gene does not function within the genus *Hydrogenophilus* bacteria.

On the other hand, *Gluconobacter oxydans* pdc gene functions within bacteria of the genus *Hydrogenophilus*, and a highly active pyruvate decarboxylase is produced.

(ii) Bacteria of the genus *Hydrogenophilus* do not originally produce ethanol, and do not have an alcohol dehydrogenase gene.

However, when an alcohol dehydrogenase gene of a heterogenous microorganism is introduced into bacteria of the genus *Hydrogenophilus*, the gene functions within the genus *Hydrogenophilus* bacteria, and a highly active alcohol dehydrogenase is produced. In particular, when *Klebsiella pneumoniae* adhP gene, *Geobacillus thermocatenulatus* adhP gene, or *Geobacillus thermoglucosidasius* adhA or adhP gene, is introduced into bacteria of the genus *Hydrogenophilus*, an especially highly active alcohol dehydrogenase is produced.

(iii) A transformant obtained by introducing *Gluconobacter oxydans* pdc gene, and an alcohol dehydrogenase gene into a bacterium of the genus *Hydrogenophilus* efficiently produces ethanol using carbon dioxide as a sole carbon source.

Second Transformant Having Ethanol Producing Ability (i) Bacteria of the genus *Hydrogenophilus* originally do not produce ethanol, and do not have an aldehyde-alcohol dehydrogenase gene.

However, by introducing an aldehyde-alcohol dehydrogenase gene of a heterogenous microorganism into bacteria of the genus *Hydrogenophilus*, the gene functions within the genus *Hydrogenophilus* bacteria, and a highly active aldehyde-alcohol dehydrogenase is produced. In particular, when adhE gene of *Escherichia coli* or *Clostridium thermocellum* is introduced into bacteria of the genus *Hydrogenophilus*, an especially highly active aldehyde-alcohol dehydrogenase is produced. As a result, the obtained transformant produces ethanol efficiently.

(ii) The activity of aldehyde-alcohol dehydrogenase is inhibited under aerobic conditions. However, a mutant aldehyde-alcohol dehydrogenase in which Glu at position 568 of the aldehyde-alcohol dehydrogenase of *Escherichia coli* has been substituted by Lys, Ala, Leu, Asn, Gly, Ser, Arg, or His, and a mutant aldehyde-alcohol dehydrogenase in which Asp at position 575 of the aldehyde-alcohol dehydrogenase of *Clostridium thermocellum* has been substituted by Asn, show activity under aerobic conditions. Bacteria of the genus *Hydrogenophilus* into which each of the mutant adhE genes of adhE(E568K, E568A, E568L, E568N, E568G, E568S, E568R, and E568H) and adhE(D575N), encoding the above mutant aldehyde-alcohol dehydrogenases, have been introduced, respectively, produce highly active aldehyde-alcohol dehydrogenases under aerobic conditions.

Bacteria of the genus *Hydrogenophilus* cannot grow under anaerobic conditions, and thus the production of substances using bacteria of the genus *Hydrogenophilus* need to be performed under aerobic conditions. In this respect, the transformants of bacteria of the genus *Hydrogenophilus* obtained by introducing these mutant adhE genes can still more efficiently produce ethanol under aerobic conditions, using carbon dioxide as a sole carbon source.

Production of Alanine (i) Bacteria of the genus *Hydrogenophilus* produce an amount of alanine required for survival, however, they do not produce alanine in an amount that can be utilized industrially. When an alanine dehydrogenase gene of a heterogenous microorganism is introduced into bacteria of the genus *Hydrogenophilus*, the gene functions within the genus *Hydrogenophilus* bacteria, and a highly active alanine dehydrogenase is produced, and therefore, the obtained transformants efficiently produce alanine using carbon dioxide as a sole carbon source. In particular, when alaD1 or alaD2 gene of *Geobacillus stearothermophilus*, or alaD1 or alaD2 gene of *Thermus thermophilus* is introduced into bacteria of the genus *Hydrogenophilus*, an especially highly active alanine dehydrogenase is produced.

(ii) A gene encoding a modified alanine dehydrogenase in which an amino acid sequence of the N terminus portion of a maltose-binding protein has been added to the N terminus of an alanine dehydrogenase brings about a higher enzymatic activity expression in bacteria of the genus *Hydrogenophilus* as compared to a gene encoding an alanine dehydrogenase in which this amino acid sequence has not been added. As a result, a transformant of a bacterium of the genus *Hydrogenophilus* into which this modified alanine dehydrogenase gene has been introduced, produces alanine still more efficiently using carbon dioxide as a sole carbon source.

The present invention has been completed based on the above findings, and provides a transformant and a method for producing chemical products, which are described below.

Aspect 1. A DNA of (a1), (a2), or (a3) below:
(a1) DNA which consists of a base sequence of SEQ ID NO: 1;
(a2) DNA which consists of a base sequence having 90% or more identity with SEQ ID NO: 1, the DNA encoding a polypeptide having 2-keto-acid decarboxylase activity;
(a3) DNA which hybridizes with a DNA consisting of a base sequence complementary to SEQ ID NO: 1 under stringent conditions, and which encodes a polypeptide having 2-keto-acid decarboxylase activity.

Aspect 2. A transformant obtained by introducing (a) a DNA according to aspect 1 and (b) an alcohol dehydrogenase gene into a bacterium of the genus *Hydrogenophilus*.

Aspect 3. The transformant according to aspect 2, wherein the alcohol dehydrogenase gene (b) is a DNA of (b1), (b2), (b3), (b4), (b5), or (b6) below:
(b1) DNA which consists of a base sequence of SEQ ID NO: 2, 3, 4, or 5;
(b2) DNA which consists of a base sequence having 90% or more identity with SEQ ID NO: 2, 3, 4, or 5, the DNA encoding a polypeptide having alcohol dehydrogenase activity;
(b3) DNA which hybridizes with a DNA consisting of a base sequence complementary to SEQ ID NO: 2, 3, 4, or 5 under stringent conditions, and which encodes a polypeptide having alcohol dehydrogenase activity;
(b4) DNA which encodes a polypeptide consisting of an amino acid sequence of SEQ ID NO: 6, 7, 8, or 9;
(b5) DNA which encodes a polypeptide consisting of an amino acid sequence having 90% or more identity with SEQ ID NO: 6, 7, 8, or 9, the polypeptide having alcohol dehydrogenase activity;
(b6) DNA which encodes a polypeptide consisting of an amino acid sequence having a deletion, substitution, or addition of one or a plurality of amino acids in the amino acid sequence of SEQ ID NO: 6, 7, 8, or 9, the polypeptide having alcohol dehydrogenase activity.

Aspect 4. The transformant according to aspect 2 or 3, wherein the bacterium of the genus *Hydrogenophilus* is *Hydrogenophilus thermoluteolus*.

Aspect 5. A method for producing isobutanol comprising a step of culturing the transformant according to any one of aspects 2 to 4, while using carbon dioxide as substantially a sole carbon source.

Aspect 6. A transformant obtained by introducing (c) a pyruvate decarboxylase gene of (c1), (c2), (c3), (c4), (c5), or (c6) below, and (b) an alcohol dehydrogenase gene, into a bacterium of the genus *Hydrogenophilus*:
(c1) DNA which consists of a base sequence of SEQ ID NO: 10;
(c2) DNA which consists of a base sequence having 90% or more identity with SEQ ID NO: 10, the DNA encoding a polypeptide having pyruvate decarboxylase activity;
(c3) DNA which hybridizes with a DNA consisting of a base sequence complementary to SEQ ID NO: 10 under stringent conditions, and which encodes a polypeptide having pyruvate decarboxylase activity;
(c4) DNA which encodes a polypeptide consisting of an amino acid sequence of SEQ ID NO: 11;
(c5) DNA which encodes a polypeptide consisting of an amino acid sequence having 90% or more identity with SEQ ID NO: 11, the polypeptide having pyruvate decarboxylase activity;
(c6) DNA which encodes a polypeptide consisting of an amino acid sequence having a deletion, substitution, or addition of one or a plurality of amino acids in the amino acid sequence of SEQ ID NO: 11, the polypeptide having pyruvate decarboxylase activity.

Aspect 7. The transformant according to aspect 6, wherein the alcohol dehydrogenase gene (b) is a DNA of (b1), (b2), (b3), (b4), (b5), or (b6) below:
(b1) DNA which consists of a base sequence of SEQ ID NO: 2, 3, 4, or 5;
(b2) DNA which consists of a base sequence having 90% or more identity with SEQ ID NO: 2, 3, 4, or 5, the DNA encoding a polypeptide having alcohol dehydrogenase activity;
(b3) DNA which hybridizes with a DNA consisting of a base sequence complementary to SEQ ID NO: 2, 3, 4, or 5 under stringent conditions, and which encodes a polypeptide having alcohol dehydrogenase activity;
(b4) DNA which encodes a polypeptide consisting of an amino acid sequence of SEQ ID NO: 6, 7, 8, or 9;
(b5) DNA which encodes a polypeptide consisting of an amino acid sequence having 90% or more identity with SEQ ID NO: 6, 7, 8, or 9, the polypeptide having alcohol dehydrogenase activity;
(b6) DNA which encodes a polypeptide consisting of an amino acid sequence having a deletion, substitution, or addition of one or a plurality of amino acids in the amino acid sequence of SEQ ID NO: 6, 7, 8, or 9, the polypeptide having alcohol dehydrogenase activity.

Aspect 8. The transformant according to aspect 6 or 7, wherein the bacterium of the genus *Hydrogenophilus* is *Hydrogenophilus thermoluteolus*.

Aspect 9. A method for producing ethanol comprising a step of culturing the transformant according to any one of aspects 6 to 8, while using carbon dioxide as substantially a sole carbon source.

Aspect 10. A transformant obtained by introducing (d) an aldehyde-alcohol dehydrogenase gene into a bacterium of the genus *Hydrogenophilus*.

Aspect 11. The transformant according to aspect 10, wherein the aldehyde-alcohol dehydrogenase gene (d) is a DNA of (d1), (d2), (d3), (d4), (d5), (d6), (d7), (d8), or (d9) below:
(d1) DNA which consists of a base sequence of SEQ ID NO: 12 or 13;

(d2) DNA which consists of a base sequence having 90% or more identity with SEQ ID NO: 12 or 13, the DNA encoding a polypeptide having aldehyde-alcohol dehydrogenase activity;
(d3) DNA which hybridizes with a DNA consisting of a base sequence complementary to SEQ ID NO: 12 or 13 under stringent conditions, and which encodes a polypeptide having aldehyde-alcohol dehydrogenase activity;
(d4) DNA which encodes a polypeptide consisting of an amino acid sequence of SEQ ID NO: 14 or 15;
(d5) DNA which encodes a polypeptide consisting of an amino acid sequence having 90% or more identity with SEQ ID NO: 14 or 15, the polypeptide having aldehyde-alcohol dehydrogenase activity;
(d6) DNA which encodes a polypeptide consisting of an amino acid sequence having a deletion, substitution, or addition of one or a plurality of amino acids in the amino acid sequence of SEQ ID NO: 14 or 15, the polypeptide having aldehyde-alcohol dehydrogenase activity;
(d7) DNA which encodes a polypeptide consisting of an amino acid sequence of SEQ ID NO: 16, 17, 18, 19, 20, 21, 22, 23, or 24;
(d8) DNA which encodes a polypeptide consisting of an amino acid sequence having 90% or more identity with SEQ ID NO: 16, 17, 18, 19, 20, 21, 22, or 23 (with the proviso that the amino acid of amino acid number 568 in the polypeptide is Lys, Ala, Leu, Asn, Gly, Ser, Arg, or His), the polypeptide having aldehyde-alcohol dehydrogenase activity, or DNA which encodes a polypeptide consisting of an amino acid sequence having 90% or more identity with SEQ ID NO: 24 (with the proviso that the amino acid of amino acid number 575 in the polypeptide is Asn), the polypeptide having aldehyde-alcohol dehydrogenase activity;
(d9) DNA which encodes a polypeptide consisting of an amino acid sequence having a deletion, substitution, or addition of one or a plurality of amino acids in the amino acid sequence of SEQ ID NO: 16, 17, 18, 19, 20, 21, 22, or 23 (with the proviso that the amino acid of amino acid number 568 is Lys, Ala, Leu, Asn, Gly, Ser, Arg, or His), the polypeptide having aldehyde-alcohol dehydrogenase activity, or DNA which encodes a polypeptide consisting of an amino acid sequence having a deletion, substitution, or addition of one or a plurality of amino acids in the amino acid sequence of SEQ ID NO: 24 (with the proviso that the amino acid of amino acid number 575 is Asn), the polypeptide having aldehyde-alcohol dehydrogenase activity.

Aspect 12. The transformant according to aspect 11, wherein the DNA of (d7) is a DNA which consists of a base sequence of SEQ ID NO: 25, 26, 27, or 28.

Aspect 13. The transformant according to any one of aspects 10 to 12, wherein the bacterium of the genus *Hydrogenophilus* is *Hydrogenophilus thermoluteolus*.

Aspect 14. A method for producing ethanol comprising a step of culturing the transformant according to any one of aspects 10 to 13, while using carbon dioxide as substantially a sole carbon source.

Aspect 15. An aldehyde-alcohol dehydrogenase which consists of a polypeptide of (d7'), (d8'), or (d9') below (with the proviso that the amino acid at position 575 from the N terminus of polypeptides (d8') and
(d9') is Asn):
(d7') polypeptide which consists of an amino acid sequence of SEQ ID NO: 24;
(d8') polypeptide which consists of an amino acid sequence having 90% or more identity with SEQ ID NO: 24, the polypeptide having aldehyde-alcohol dehydrogenase activity;
(d9') polypeptide which consists of an amino acid sequence having a deletion, substitution, or addition of one or a plurality of amino acids in the amino acid sequence of SEQ ID NO: 24, the polypeptide having aldehyde-alcohol dehydrogenase activity.

Aspect 16. An aldehyde-alcohol dehydrogenase gene which consists of a DNA of (d10'), (d11'), or (d12') below (with the proviso that the 3 nucleotides from position 1723 to position 1725 from the 5' end of the DNAs of (d11') and (d12') are AAC or AAT):
(d10') DNA which consists of a base sequence of SEQ ID NO: 27 or 28;
(d11') DNA which consists of a base sequence having 90% or more identity with SEQ ID NO: 27 or 28, the DNA encoding a polypeptide having aldehyde-alcohol dehydrogenase activity;
(d12') DNA which hybridizes with a DNA consisting of a base sequence complementary to SEQ ID NO: 27 or 28 under stringent conditions, the DNA encoding a polypeptide having aldehyde-alcohol dehydrogenase activity.

Aspect 17. A transformant obtained by introducing (e) an alanine dehydrogenase gene into a bacterium of the genus *Hydrogenophilus*.

Aspect 18. The transformant according to aspect 17, wherein the alanine dehydrogenase gene (e) is a DNA of (e1), (e2), (e3), (e4), (e5), (e6), (e7), (e8), (e9), (e10), (e11), or (e12) below:
(e1) DNA which consists of a base sequence of SEQ ID NO: 29, 30, 31, or 32;
(e2) DNA which consists of a base sequence having 90% or more identity with SEQ ID NO: 29, 30, 31, or 32, the DNA encoding a polypeptide having alanine dehydrogenase activity;
(e3) DNA which hybridizes with a DNA consisting of a base sequence complementary to SEQ ID NO: 29, 30, 31, or 32 under stringent conditions, and which encodes a polypeptide having alanine dehydrogenase activity;
(e4) DNA which encodes a polypeptide consisting of an amino acid sequence of SEQ ID NO: 33, 34, 35, or 36;
(e5) DNA which encodes a polypeptide consisting of an amino acid sequence having 90% or more identity with SEQ ID NO: 33, 34, 35, or 36, the polypeptide having alanine dehydrogenase activity;
(e6) DNA which encodes a polypeptide consisting of an amino acid sequence having a deletion, substitution, or addition of one or a plurality of amino acids in the amino acid sequence of SEQ ID NO: 33, 34, 35, or 36, the polypeptide having alanine dehydrogenase activity;
(e7) DNA which encodes a polypeptide consisting of an amino acid sequence in which an amino acid sequence of SEQ ID NO: 37 is added to the N terminus of the amino acid sequence of SEQ ID NO: 33, 34, 35, or 36;
(e8) DNA which encodes a polypeptide consisting of an amino acid sequence in which the amino acid sequence of SEQ ID NO: 37 is added to the N terminus of the amino acid sequence having 90% or more identity with SEQ ID NO: 33, 34, 35, or 36, the polypeptide having alanine dehydrogenase activity;
(e9) DNA which encodes a polypeptide consisting of an amino acid sequence in which the amino acid sequence of SEQ ID NO: 37 is added to the N terminus of the amino acid sequence having a deletion, substitution, or addition of one or a plurality of amino acids in the amino acid sequence of SEQ ID NO: 33, 34, 35, or 36, the polypeptide having alanine dehydrogenase activity;

(e10) DNA which consists of a base sequence in which a base sequence of SEQ ID NO: 38 is added to the 5' end of the base sequence of SEQ ID NO: 29, 30, 31, or 32;
(e11) DNA which consists of a base sequence in which the base sequence of SEQ ID NO: 38 is added to the 5' end of the base sequence having 90% or more identity with SEQ ID NO: 29, 30, 31, or 32, the DNA encoding a polypeptide having alanine dehydrogenase activity;
(e12) DNA which consists of a base sequence in which the base sequence of SEQ ID NO: 38 is added to the 5' end of a base sequence of the DNA hybridizing with a DNA consisting of a base sequence complementary to SEQ ID NO: 29, 30, 31, or 32 under stringent conditions, and which encodes a polypeptide having alanine dehydrogenase activity.
Aspect 19. The transformant according to aspect 17 or 18, wherein the bacterium of the genus *Hydrogenophilus* is *Hydrogenophilus thermoluteolus*.
Aspect 20. A method for producing alanine comprising a step of culturing the transformant according to any one of aspects 17 to 19, while using carbon dioxide as substantially a sole carbon source.
Aspect 21. A modified alanine dehydrogenase, in which a polypeptide consisting of an amino acid sequence of SEQ ID NO: 37 is added to the N terminus of an alanine dehydrogenase.
Aspect 22. The modified alanine dehydrogenase according to aspect 21, which consists of an amino acid sequence of SEQ ID NO: 39.
Aspect 23. A modified alanine dehydrogenase gene, in which a polynucleotide consisting of a base sequence of SEQ ID NO: 38 is added to the 5' end of an alanine dehydrogenase gene.
Aspect 24. The modified alanine dehydrogenase gene according to aspect 23, which consists of a base sequence of SEQ ID NO: 40.

Advantageous Effects of Invention

Countermeasures to suppress the increase in carbon dioxide include reduction of carbon dioxide emission and fixation of emitted carbon dioxide. In order to reduce carbon dioxide emission, solar energy, wind energy, geothermal energy, and the like are utilized in place of fossil energy. However, the utilization of such energies have not been able to sufficiently suppress the increase in carbon dioxide actually. Therefore, there is a need to advance the fixation or recycling of emitted carbon dioxide.

Carbon dioxide can be fixed physically or chemically, however, if carbon dioxide is fixed by utilizing a living organism, then organic substances that can be utilized as food, feed, fuel, and the like, can be produced. Namely, carbon dioxide itself as a resource can be directly converted into valuable chemical products. Accordingly, both of two problems of global warming due to the increase in carbon dioxide and difficulty in securing food, feed, and fuel can be solved.

Hydrogen oxidizing bacteria are bacteria which can grow by utilizing chemical energy generated by the reaction of hydrogen and oxygen and by using carbon dioxide as a sole carbon source. Since hydrogen oxidizing bacteria can produce chemical products using a mixed gas of oxygen, hydrogen, and carbon dioxide as a raw material, they can efficiently carry out organification of carbon dioxide and be cultured in a simple culture medium. Growth of hydrogen oxidizing bacteria is generally slow, however, the growth rate of hydrogen oxidizing bacteria of the genus *Hydrogenophilus* is remarkably high. "Journal of Mitsubishi Research Institute No. 34 1999" assesses genus *Hydrogenophilus* bacteria as follows: "Their proliferative capacity is so high that it cannot be compared with the carbon dioxide fixation ability of plants, which truly indicates the high carbon dioxide fixation ability of microorganisms".

When a heterologous gene having natural base sequence is introduced into bacteria of the genus *Hydrogenophilus* using a vector that functions within the genus *Hydrogenophilus* bacteria, a functioning protein often is not produced. According to the present invention, by introducing particular genes into bacteria of the genus *Hydrogenophilus*, the genes function within the genus *Hydrogenophilus* bacteria, and isobutanol, ethanol, or alanine can be produced.

As described above, bacteria of the genus *Hydrogenophilus* have a particularly remarkable carbon dioxide fixation ability among organisms having carbon dioxide fixation ability, and therefore, by using the transformant of the present invention, carbon dioxide can be fixed and isobutanol, ethanol, or alanine can be produced at an industrial level.

MODE FOR CARRYING OUT THE INVENTION

The present invention is described in detail below:
(1) Transformant Having Isobutanol Producing Ability The codon-optimized 2-keto-acid decarboxylase gene of the present invention is obtained by codon-optimization of the 2-keto-acid decarboxylase of *Lactococcus lactis*, and is different from the 2-keto-acid decarboxylase gene (kivD) of *Lactococcus lactis* in base sequence. This gene is a DNA which consists of the base sequence of SEQ ID NO: 1. This codon-optimized 2-keto-acid decarboxylase gene functions within bacteria of the genus *Hydrogenophilus*, and can bring about 2-keto-acid decarboxylase activity expression.

The amino acid sequence of 2-keto-acid decarboxylase produced based on this codon-optimized 2-keto-acid decarboxylase gene is the same as that of the 2-keto-acid decarboxylase of *Lactococcus lactis* (SEQ ID NO: 41).

DNA which consists of a base sequence having 90% or more, preferably 95% or more, more preferably 98% or more, further more preferably 99% or more identity with SEQ ID NO: 1, the DNA encoding a polypeptide having 2-keto-acid decarboxylase activity, can also be used to bring about 2-keto-acid decarboxylase activity expression within bacteria of the genus *Hydrogenophilus*.

In the present invention, the identities of base sequences were calculated using GENETYX ver. 17 (made by GENETYX Corporation).

DNA which hybridizes with a DNA consisting of a base sequence complementary to SEQ ID NO: 1 under stringent conditions, the DNA encoding a polypeptide having 2-keto-acid decarboxylase activity, can also be used.

In the present invention, "stringent conditions" means conditions in which hybridization is performed in a hybridization solution at a salt concentration of 6×SSC at temperatures from 50 to 60° C. for 16 hours, and then washing is performed with a solution at a salt concentration of 0.1×SSC.

The base sequences of the above-described homologues of the codon-optimized 2-keto-acid decarboxylase gene (SEQ ID NO: 1) are desirably different from SEQ ID NO: 1 to the extent that the amino acid sequence of the encoded 2-keto-acid decarboxylase is the same as that of 2-keto-acid decarboxylase of *Lactococcus lactis* (SEQ ID NO: 41).

The present invention also encompasses a vector comprising the above-described codon-optimized 2-keto-acid decarboxylase gene or the homologues thereof (in particular, a vector that functions within bacteria of the genus *Hydrogenophilus*).

By introducing an alcohol dehydrogenase gene together with the above-described codon-optimized 2-keto-acid decarboxylase gene or the homologue thereof into bacteria of the genus *Hydrogenophilus*, the genus *Hydrogenophilus* bacteria come to produce isobutanol.

Accordingly, the present invention encompasses a transformant which is obtained by introducing (a) (a1) DNA which consists of a base sequence of SEQ ID NO: 1, (a2) DNA which consists of a base sequence having 90% or more identity with SEQ ID NO: 1, the DNA encoding a polypeptide having 2-keto-acid decarboxylase activity, or (a3) DNA which hybridizes with a DNA consisting of a base sequence complementary to SEQ ID NO: 1 under stringent conditions, and which encodes a polypeptide having 2-keto-acid decarboxylase activity, and (b) DNA of an alcohol dehydrogenase gene, into a host bacterium of the genus *Hydrogenophilus*. In other words, this transformant possesses exogenous DNAs of (a) and (b) described above.

Examples of the alcohol dehydrogenase gene include (b1) alcohol dehydrogenase gene (adhP) of *Klebsiella pneumoniae*, alcohol dehydrogenase gene (adhP) of *Geobacillus thermocatenulatus*, alcohol dehydrogenase gene (adhP) of *Geobacillus thermoglucosidasius*, and alcohol dehydrogenase gene (adhA) of *Geobacillus thermoglucosidasius*, which are preferable in that they have good isobutanol production efficiency. The base sequences of these genes are SEQ ID NOs: 2, 3, 4, and 5, respectively.

(b2) DNA which consists of a base sequence having 90% or more, preferably 95% or more, more preferably 98% or more, further more preferably 99% or more identity with SEQ ID NO: 2, 3, 4, or 5, the DNA encoding a polypeptide having alcohol dehydrogenase activity, and (b3) DNA which hybridizes with a DNA consisting of a base sequence complementary to SEQ ID NO: 2, 3, 4, or 5 under stringent conditions, and which encodes a polypeptide having alcohol dehydrogenase activity, are also preferable.

In addition, examples of the alcohol dehydrogenase gene include (b4) DNA which encodes a polypeptide consisting of an amino acid sequence of SEQ ID NO: 6, 7, 8, or 9, or (b5) DNA which encodes a polypeptide consisting of an amino acid sequence having 90% or more, preferably 95% or more, more preferably 98% or more, further more preferably 99% or more identity with SEQ ID NO: 6, 7, 8, or 9, the polypeptide having alcohol dehydrogenase activity, which are also preferable.

SEQ ID NOs: 6, 7, 8, and 9 are amino acid sequences of alcohol dehydrogenase ADHP of *Klebsiella pneumoniae*, *Geobacillus thermocatenulatus*, and *Geobacillus thermoglucosidasius*, and alcohol dehydrogenase ADHA of *Geobacillus thermoglucosidasius*, respectively.

In the present invention, the identities of amino acid sequences were calculated using GENETYX ver. 17 (made by GENETYX Corporation).

(b6) DNA which encodes a polypeptide consisting of an amino acid sequence having a deletion, substitution, or addition of one or a plurality of amino acids in the amino acid sequence of SEQ ID NO: 6, 7, 8, or 9, the polypeptide having alcohol dehydrogenase activity, is also preferable.

In the present invention, examples of plurality include 1 to 5, in particular 1 to 3, in particular 1 to 2, and particularly 1.

In the present invention, when an amino acid residue of a polypeptide that has a certain activity is substituted, the amino acid residue may be substituted by another chemically similar amino acid residue, in order to carry out substitution so that the polypeptide has the certain activity after substitution (in particular, so that the polypeptide maintains an activity that is the same level as the certain activity). For example, a hydrophobic amino acid residue can be substituted by another hydrophobic amino acid residue, or a charged amino acid residue can be substituted by another charged amino acid residue having the same charge. Chemically similar amino acids which can be thus substituted are well known to those skilled in the art. Examples of amino acids which have a nonpolar (hydrophobic) sidechain include glycine, alanine, valine, isoleucine, leucine, proline, tryptophan, phenylalanine, methionine, and the like, and these amino acids can be substituted with each other. Examples of neutral amino acids which have a polar sidechain include serine, threonine, tyrosine, glutamine, asparagine, cysteine, and the like, and these amino acids can be substituted with each other. Examples of (basic) amino acids which have a positive charge include arginine, histidine, lysine, and the like, and these amino acids can be substituted with each other. In addition, examples of (acidic) amino acids which have a negative charge include aspartic acid, glutamic acid, and the like, and these amino acids can be substituted with each other.

In the present invention, when a nucleotide of a DNA which encodes a polypeptide that has a certain activity is substituted, there is a tendency for the polypeptide to have the certain activity after substitution (in particular, to maintain an activity that is the same level as the certain activity), if the nucleotide is substituted so that the amino acid sequence of the encoded polypeptide is unchanged. In addition, if a nucleotide is substituted so that the corresponding amino acid residue is substituted by another chemically similar amino acid residue, there is a tendency for the polypeptide to have the certain activity after substitution (in particular, to maintain an activity that is the same level as the certain activity).

In the present invention, in order to confirm that a polypeptide has a 2-keto-acid decarboxylase activity, a test polypeptide is reacted with 2-ketoisovalerate under the coexistence of alcohol dehydrogenase and NADH, and decrease in absorbance at 340 nm is detected. 2-keto-acid decarboxylase produces isobutyraldehyde from 2-ketoisovalerate, and the coexisting alcohol dehydrogenase produces isobutanol from isobutyraldehyde. Alcohol dehydrogenase consumes NADH when isobutanol is produced from isobutyraldehyde, and thus decrease in the amount of NADH is detected using decrease in absorbance at 340 nm as an index. Specifically, the method described in item "Examples" is carried out. If the test polypeptide reduces absorbance at 340 nm even by a slight degree, the polypeptide is determined to have 2-keto-acid decarboxylase activity.

In the present invention, in order to confirm that a polypeptide has an alcohol dehydrogenase activity in which isobutyraldehyde is used as a substrate, a test polypeptide is reacted with isobutyraldehyde under the coexistence of NADH, and decrease in absorbance at 340 nm is detected. Alcohol dehydrogenase produces isobutanol from isobutyraldehyde which is accompanied by the conversion of NADH to NAD, and thus decrease in the amount of NADH is detected using decrease in absorbance at 340 nm as an index. Specifically, the method described in item "Examples" is carried out. If the test polypeptide reduces absorbance at 340 nm even by a slight degree, the polypeptide is determined to have alcohol dehydrogenase activity in which isobutyraldehyde is used as a substrate.

(2) Transformant Having Ethanol Producing Ability
First Transformant Having Ethanol Producing Ability The present invention encompasses a transformant obtained by introducing (c) (c1) DNA which consists of a base sequence of SEQ ID NO: 10, (c2) DNA which consists of a base sequence having 90% or more, in particular 95% or more, in particular 98% or more, in particular 99% or more identity with SEQ ID NO: 10, the DNA encoding a polypeptide having pyruvate decarboxylase activity, or (c3) DNA which hybridizes with a DNA consisting of a base sequence complementary to SEQ ID NO: 10 under stringent conditions, and which encodes a polypeptide having pyruvate decarboxylase activity and DNA of (b) an alcohol dehydrogenase gene, into a host bacterium of the genus *Hydrogenophilus*. In other words, this transformant possesses exogenous DNAs of (c) and (b). This transformant can produce ethanol due to the possession of DNAs of (c) and (b).

SEQ ID NO: 10 is a base sequence of the pyruvate decarboxylase gene (pdc gene) of *Gluconobacter oxydans*.

Examples of pyruvate decarboxylase genes which can also be used include (c4) DNA which encodes a polypeptide consisting of an amino acid sequence of SEQ ID NO: 11, (c5) DNA which encodes a polypeptide consisting of an amino acid sequence having 90% or more, preferably 95% or more, more preferably 98% or more, further more preferably 99% or more identity with SEQ ID NO: 11, the polypeptide having pyruvate decarboxylase activity, or (c6) DNA which encodes a polypeptide consisting of an amino acid sequence having a deletion, substitution, or addition of one or a plurality of amino acids in the amino acid sequence of SEQ ID NO: 11, the polypeptide having pyruvate decarboxylase activity.

SEQ ID NO: 11 is an amino acid sequence of a pyruvate decarboxylase of *Gluconobacter oxydans*.

Examples of (b) alcohol dehydrogenase gene include (b1) alcohol dehydrogenase gene (adhP) of *Klebsiella pneumoniae*, alcohol dehydrogenase gene (adhP) of *Geobacillus thermocatenulatus*, alcohol dehydrogenase gene (adhP) of *Geobacillus thermoglucosidasius*, and alcohol dehydrogenase gene (adhA) of *Geobacillus thermoglucosidasius*, which are preferable in that they have good ethanol production efficiency. The base sequences of these genes are SEQ ID NOs: 2, 3, 4, and 5, respectively.

(b2) DNA which consists of a base sequence having 95% or more, in particular 98% or more, in particular 99% or more identity with SEQ ID NO: 2, 3, 4, or 5, the DNA encoding a polypeptide having alcohol dehydrogenase activity, can also be used preferably. (b3) DNA which hybridizes with a DNA consisting of a base sequence complementary to SEQ ID NO: 2, 3, 4, or 5 under stringent conditions, and which encodes a polypeptide having alcohol dehydrogenase activity, can also be used preferably.

(b4) DNA which encodes a polypeptide consisting of an amino acid sequence of SEQ ID NO: 6, 7, 8, or 9, can also be used preferably as the alcohol dehydrogenase gene. Furthermore, (b5) DNA which encodes a polypeptide consisting of an amino acid sequence having 90% or more, preferably 95% or more, more preferably 98% or more, further more preferably 99% or more identity with SEQ ID NO: 6, 7, 8, or 9, the polypeptide having alcohol dehydrogenase activity, and (b6) DNA which encodes a polypeptide consisting of an amino acid sequence having a deletion, substitution, or addition of one or a plurality of amino acids in the amino acid sequence of SEQ ID NO: 6, 7, 8, or 9, the polypeptide having alcohol dehydrogenase activity, can also be used preferably.

SEQ ID NOs: 6, 7, 8, and 9 are amino acid sequences of alcohol dehydrogenase ADHP of *Klebsiella pneumoniae, Geobacillus thermocatenulatus*, and *Geobacillus thermoglucosidasius*, and alcohol dehydrogenase ADHA of *Geobacillus thermoglucosidasius*, respectively.

In the present invention, in order to confirm that a polypeptide has a pyruvate decarboxylase activity, a test polypeptide is reacted with pyruvic acid under the coexistence of alcohol dehydrogenase and NADH, and decrease in absorbance at 340 nm is detected. Pyruvate decarboxylase produces acetaldehyde from pyruvic acid, and alcohol dehydrogenase produces ethanol from acetaldehyde. Alcohol dehydrogenase consumes NADH when ethanol is produced from acetaldehyde, and thus decrease in the amount of NADH is detected using decrease in absorbance at 340 nm as an index. Specifically, the method described in item "Examples" is carried out. If the test polypeptide reduces absorbance at 340 nm even by a slight degree, the polypeptide is determined to have pyruvate decarboxylase activity.

In the present invention, in order to confirm that a polypeptide has an alcohol dehydrogenase activity in which acetaldehyde is used as a substrate, a test polypeptide is reacted with acetaldehyde under the coexistence of NADH, and decrease in absorbance at 340 nm is detected. Alcohol dehydrogenase produces ethanol from acetaldehyde which is accompanied by the conversion of NADH to NAD, and thus decrease in the amount of NADH is detected using decrease in absorbance at 340 nm as an index. Specifically, the method described in item "Examples" is carried out. If the test polypeptide reduces absorbance at 340 nm even by a slight degree, the polypeptide is determined to have alcohol dehydrogenase activity in which acetaldehyde is used as a substrate.

Second Transformant Having Ethanol Producing Ability

The present invention encompasses a transformant which is obtained by introducing DNA of (d) an aldehyde-alcohol dehydrogenase gene, into a host bacterium of genus *Hydrogenophilus*. In other words, this transformant possesses an exogenous DNA of (d) an aldehyde-alcohol dehydrogenase gene. This transformant can produce ethanol due to the possession of DNA of (d).

Examples of the aldehyde-alcohol dehydrogenase gene include (d1) aldehyde-alcohol dehydrogenase gene (adhE) of *Escherichia coli*, and aldehyde-alcohol dehydrogenase gene (adhE) of *Clostridium thermocellum*, which are preferable in that they have good ethanol production efficiency. The base sequence of *Escherichia coli* adhE is SEQ ID NO: 12, and the base sequence of *Clostridium thermocellum* adhE is SEQ ID NO: 13.

(d2) DNA which consists of a base sequence having 90% or more, in particular 95% or more, in particular 98% or more, in particular 99% or more identity with a DNA consisting of a base sequence of SEQ ID NO: 12 or 13, and which encodes a polypeptide having aldehyde-alcohol dehydrogenase activity, and (d3) DNA which hybridizes with a DNA consisting of a base sequence complementary to SEQ ID NO: 12 or 13 under stringent conditions, and which encodes a polypeptide having aldehyde-alcohol dehydrogenase activity, can also be used preferably.

(d4) DNA which encodes a polypeptide consisting of an amino acid sequence of SEQ ID NO: 14 or 15, can also be used preferably. Furthermore, (d5) DNA which encodes a polypeptide consisting of an amino acid sequence having 90% or more, in particular 95% or more, in particular 98% or more, in particular 99% or more identity with SEQ ID NO: 14 or 15, the polypeptide having aldehyde-alcohol dehydrogenase activity, and (d6) DNA which encodes a polypeptide consisting of an amino acid sequence having a deletion, substitution, or addition of one or a plurality of amino acids in the amino acid sequence of SEQ ID NO: 14 or 15, the polypeptide having aldehyde-alcohol dehydrogenase activity, can also be preferably used.

SEQ ID NO: 14 is an amino acid sequence of the aldehyde-alcohol dehydrogenase (ADHE) of *Escherichia coli*, and SEQ ID NO: 15 is an amino acid sequence of the aldehyde-alcohol dehydrogenase (ADHE) of *Clostridium thermocellum*.

The activity of aldehyde-alcohol dehydrogenase is inhibited under aerobic conditions, and thus, in the present invention, an attempt was made to use an aldehyde-alcohol dehydrogenase that expresses high activity under aerobic conditions, within bacteria of the genus *Hydrogenophilus*.

As a result, it was found that a mutant ADHE in which Glu at amino acid number 568 of SEQ ID NO: 14, which is the amino acid sequence of an aldehyde-alcohol dehydrogenase of *Escherichia coli*, has been substituted by Lys, Ala, Leu, Asn, Gly, Ser, Arg, or His, can express high activity under aerobic conditions within bacteria of the genus *Hydrogenophilus*. The amino acid sequences of mutant ADHE, in which the Glu of amino acid number 568 has been substituted by Lys, Ala, Leu, Asn, Gly, Ser, Arg, and His, are shown in SEQ ID NOs: 16, 17, 18, 19, 20, 21, 22, and 23, respectively.

Mutant ADHE(E568K) which consists of the amino acid sequence of SEQ ID NO: 16, in which Glu of amino acid number 568 of SEQ ID NO: 14 has been substituted by Lys, is especially preferable.

Therefore, in the present invention, (d7) DNA which encodes a polypeptide consisting of an amino acid sequence in which Glu of amino acid number 568 of SEQ ID NO: 14 has been substituted by Lys, Ala, Leu, Asn, Gly, Ser, Arg, or His, can be preferably used.

(d8) DNA which encodes a polypeptide consisting of an amino acid sequence having 90% or more, in particular 95% or more, in particular 98% or more, in particular 99% or more identity with an amino acid sequence in which Glu of amino acid number 568 of SEQ ID NO: 14 has been substituted by Lys, Ala, Leu, Asn, Gly, Ser, Arg, or His (SEQ ID NO: 16, 17, 18, 19, 20, 21, 22, or 23), the polypeptide having aldehyde-alcohol dehydrogenase activity, and (d9) DNA which encodes a polypeptide consisting of an amino acid sequence having a deletion, substitution, or addition of one or a plurality of amino acids in the amino acid sequence in which Glu of amino acid number 568 of SEQ ID NO: 14 has been substituted by Lys, Ala, Leu, Asn, Gly, Ser, Arg, or His (SEQ ID NO: 16, 17, 18, 19, 20, 21, 22, or 23), the polypeptide having aldehyde-alcohol dehydrogenase activity, can also be preferably used.

Note, however, that in the polypeptides of (d8) and (d9), the amino acid of amino acid number 568 is Lys, Ala, Leu, Asn, Gly, Ser, Arg, or His, respectively, or in the order described above.

A base sequence of the mutant adhE in which the amino acid at position 568 of the expressed aldehyde-alcohol dehydrogenase becomes Lys, is a base sequence in which GAG at base positions 1702 to 1704 of SEQ ID NO: 12, which is a base sequence of *Escherichia coli* adhE, has been substituted by AAG or AAA (SEQ ID NO: 25 or 26).

A base sequence of adhE in which the amino acid at position 568 of the expressed aldehyde-alcohol dehydrogenase becomes Ala, is a base sequence in which GAG at base positions 1702 to 1704 of SEQ ID NO: 12 has been substituted by GCT, GCC, GCA, or GCG.

A base sequence of adhE in which the amino acid at position 568 of the expressed aldehyde-alcohol dehydrogenase becomes Leu is a base sequence in which GAG at base positions 1702 to 1704 of SEQ ID NO: 12 has been substituted by TTA, TTG, CTT, CTC, CTA, or CTG.

A base sequence of adhE in which the amino acid at position 568 of the expressed aldehyde-alcohol dehydrogenase becomes Asn is a base sequence in which the GAG at base positions 1702 to 1704 of SEQ ID NO: 12 has been substituted by AAT or AAC.

A base sequence of adhE in which the amino acid at position 568 of the expressed aldehyde-alcohol dehydrogenase becomes Gly, is a base sequence in which the GAG at base positions 1702 to 1704 of SEQ ID NO: 12 has been substituted by GGT, GGC, GGA, or GGG.

A base sequence of adhE in which the amino acid at position 568 of the expressed aldehyde-alcohol dehydrogenase becomes Ser, is a base sequence in which the GAG at base positions 1702 to 1704 of SEQ ID NO: 12 has been substituted by TCT, TCC, TCA, TCG, AGT, or AGC.

A base sequence of adhE in which the amino acid at position 568 of the expressed aldehyde-alcohol dehydrogenase becomes Arg, is a base sequence in which the GAG at base positions 1702 to 1704 of SEQ ID NO: 12 has been substituted by CGT, CGC, CGA, AGA, or AGG.

A base sequence of adhE in which the amino acid at position 568 of the expressed aldehyde-alcohol dehydrogenase becomes His, is a base sequence in which the GAG at base positions 1702 to 1704 of SEQ ID NO: 12 has been substituted by CAT or CAC.

In particular, SEQ ID NO: 25 or 26 is preferable in terms of good ethanol production efficiency by bacteria of the genus *Hydrogenophilus*, and SEQ ID NO: 25 is more preferable.

In addition, DNA which consists of a base sequence having 90% or more, in particular 95% or more, in particular 98% or more, in particular 99% or more identity with a base sequence of the above-described mutant adhE encoding a mutant ADHE in which Glu of amino acid number 568 of SEQ ID NO: 14 of the aldehyde-alcohol dehydrogenase (ADHE) of *Escherichia coli* has been substituted by Lys, Ala, Leu, Asn, Gly, Ser, Arg, or His, the DNA encoding a polypeptide having aldehyde-alcohol dehydrogenase activity (a homologue of mutant adhE of *Escherichia coli*), as well as DNA which hybridizes under stringent conditions with a DNA consisting of a base sequence complementary to the base sequence of the above-described mutant adhE encoding a mutant ADHE in which Glu of amino acid number 568 of SEQ ID NO: 14 of the aldehyde-alcohol dehydrogenase (ADHE) of *Escherichia coli* has been substituted by Lys, Ala, Leu, Asn, Gly, Ser, Arg, or His, and which encodes a polypeptide having aldehyde-alcohol dehydrogenase activity (a homologue of mutant adhE of *Escherichia coli*), can also be preferably used.

Note, however, that in the above-described homologue of mutant adhE of *Escherichia coli*, the base sequence of the 3 nucleotides that correspond to amino acid number 568 of the mutant ADHE of *Escherichia coli* is the same as any of the 3 nucleotides that correspond to Lys, Ala, Leu, Asn, Gly, Ser, Arg, or His of amino acid number 568 of the mutant ADHE of *Escherichia coli*.

Namely, the nucleotides of base numbers 1702 to 1704 of the above-described homologue of the DNA encoding the mutant ADHE of *Escherichia coli*, in which amino acid number 568 is Lys, is AAG or AAA.

The nucleotides of base numbers 1702 to 1704 of the homologue of the DNA encoding the mutant ADHE of *Escherichia coli*, in which amino acid number 568 is Ala, is GCT, GCC, GCA, or GCG.

The nucleotides of base numbers 1702 to 1704 of the above-described homologue of the DNA encoding the mutant ADHE of *Escherichia coli*, in which amino acid number 568 is Leu, is TTA, TTG, CTT, CTC, CTA, or CTG.

The nucleotides of base numbers 1702 to 1704 of the above-described homologue of the DNA encoding the mutant ADHE of *Escherichia coli*, in which amino acid number 568 is Asn, is AAT or AAC.

The nucleotides of base numbers 1702 to 1704 of the above-described homologue of the DNA encoding the mutant ADHE of *Escherichia coli*, in which amino acid number 568 is Gly, is GGT, GGC, GGA, or GGG.

The nucleotides of base numbers 1702 to 1704 of the above-described homologue of the DNA encoding the mutant ADHE of *Escherichia coli*, in which amino acid number 568 is Ser, is TCT, TCC, TCA, TCG, AGT, or AGC.

The nucleotides of base numbers 1702 to 1704 of the above-described homologue of the DNA encoding the mutant ADHE of *Escherichia coli*, in which amino acid number 568 is Arg, is GCT, CGC, CGA, AGA, or AGG.

The nucleotides of base numbers 1702 to 1704 of the above-described homologue of the DNA encoding the mutant ADHE of *Escherichia coli*, in which amino acid number 568 is His, is CAT or CAC.

It was found that a mutant ADHE consisting of an amino acid sequence of SEQ ID NO: 24 in which Asp of amino acid number 575 of SEQ ID NO: 15, which is the amino acid sequence of the aldehyde-alcohol dehydrogenase (ADHE) of *Clostridium thermocellum*, has been substituted by Asn, can express high activity under aerobic conditions in bacteria of the genus *Hydrogenophilus*.

Therefore, in the present invention, (d7) DNA (adhE (D575N)) encoding a polypeptide which consists of an amino acid sequence in which Asp of amino acid number 575 of SEQ ID NO: 15 has been substituted by Asn (SEQ ID NO: 24), can be preferably introduced into bacteria of the genus *Hydrogenophilus*.

(d8) DNA which encodes a polypeptide consisting of an amino acid sequence having 90% or more, in particular 95% or more, in particular 98% or more, in particular 99% or more identity with an amino acid sequence in which Asp of amino acid number 575 of SEQ ID NO: 15 has been substituted by Asn (SEQ ID NO: 24), the polypeptide having aldehyde-alcohol dehydrogenase activity (a homologue of mutant ADHE of *Clostridium thermocellum*), and (d9) DNA which encodes a polypeptide consisting of an amino acid sequence having a deletion, substitution, or addition of one or a plurality of amino acids in the amino acid sequence in which Asp of amino acid number 575 of SEQ ID NO: 15 has been substituted by Asn (SEQ ID NO: 24), the polypeptide having aldehyde-alcohol dehydrogenase activity (a homologue of mutant ADHE of *Clostridium thermocellum*), can also be preferably used.

Note, however, that in the homologues of mutant ADHE of *Clostridium thermocellum* of (d8) and (d9), the amino acid of amino acid number 575 is Asn.

By introducing a mutant *Clostridium thermocellum* adhE gene that gives rise to the above-described amino acid substitution, into a bacterium of the genus *Hydrogenophilus*, the obtained transformant becomes able to highly express aldehyde-alcohol dehydrogenase activity under aerobic conditions.

The base sequence of mutant adhE in which the amino acid at position 575 of the expressed aldehyde-alcohol dehydrogenase is Asn, is a base sequence in which GAC of base numbers 1723 to 1725 of SEQ ID NO: 13, which is the base sequence of *Clostridium thermocellum* adhE gene, is substituted by AAC or AAT (SEQ ID NO: 27 or 28). In particular, DNA which consists of the base sequence of SEQ ID NO: 27 is preferable.

DNA which consists of a base sequence having 90% or more, in particular 95% or more, in particular 98% or more, in particular 99% or more identity with a DNA consisting of a base sequence of SEQ ID NO: 27 or 28, and which encodes a polypeptide having aldehyde-alcohol dehydrogenase activity (a homologue of mutant adhE of *Clostridium thermocellum*), and DNA which hybridizes with a DNA consisting of a base sequence complementary to SEQ ID NO: 27 or 28 under stringent conditions, and which encodes a polypeptide having aldehyde-alcohol dehydrogenase activity (a homologue of mutant adhE of *Clostridium thermocellum*), can also be preferably used.

Note, however, that in the homologue of mutant adhE of *Clostridium thermocellum* which consists of a base sequence of SEQ ID NO: 27 or 28, the nucleotide of base numbers 1723 to 1725 are AAC or AAT.

In the present invention, an aldehyde-alcohol dehydrogenase is provided which consist of (d7') polypeptide which consists of an amino acid sequence of SEQ ID NO: 24, (d8') polypeptide which consists of an amino acid sequence having 90% or more identity with SEQ ID NO: 24, the polypeptide having aldehyde-alcohol dehydrogenase activity, or (d9') polypeptide which consists of an amino acid sequence having a deletion, substitution, or addition of one or a plurality of amino acids in the amino acid sequence of SEQ ID NO: 24, the polypeptide having aldehyde-alcohol dehydrogenase activity. Note, however, that the amino acids at position 575 from the N terminus of the polypeptides of (d8') and (d9') are Asn, respectively.

This polypeptide can be expressed within bacteria of the genus *Hydrogenophilus* and be preferably used for ethanol production, or be used for ethanol production by enzyme reaction.

The present invention also provides an aldehyde-alcohol dehydrogenase gene consisting of (d10') DNA which consists of a base sequence of SEQ ID NO: 27 or 28, (d11') DNA which consists of a base sequence having 90% or more identity with SEQ ID NO: 27 or 28, the DNA encoding a polypeptide having aldehyde-alcohol dehydrogenase activity, or (d12') DNA which hybridizes with a DNA consisting of a base sequence complementary to SEQ ID NO: 27 or 28 under stringent conditions, and which encodes a polypeptide having aldehyde-alcohol dehydrogenase activity. Note, however, that the 3 nucleotides at positions 1723 to 1725 from the 5' end of the DNA of (d11') or (d12') are AAC or AAT.

The present invention encompasses a vector comprising this aldehyde-alcohol dehydrogenase gene (in particular, a vector that functions within bacteria of the genus *Hydrogenophilus*).

This aldehyde-alcohol dehydrogenase gene and the vector comprising the gene can preferably be used for ethanol production in bacteria of the genus *Hydrogenophilus*.

Aldehyde-alcohol dehydrogenase is a bifunctional enzyme which possesses both an aldehyde dehydrogenase activity that catalyzes the reaction of producing acetaldehyde from acetyl-CoA, and an alcohol dehydrogenase activity that catalyzes the reaction of producing ethanol from acetaldehyde.

In the present invention, it is determined that there is aldehyde-alcohol dehydrogenase activity, when a test polypeptide shows both an aldehyde dehydrogenase activity in which acetyl-CoA is used as a substrate, and an alcohol dehydrogenase activity in which acetaldehyde is used as a substrate.

In the present invention, in order to confirm that a polypeptide has an aldehyde dehydrogenase activity in which acetyl-CoA is used as a substrate, a test polypeptide is reacted with acetyl-CoA under the coexistence of NADH, and decrease in absorbance at 340 nm is detected. Aldehyde dehydrogenase produces acetaldehyde from acetyl-CoA which is accompanied by the conversion of NADH to NAD, and thus decrease in the amount of NADH is detected using decrease in absorbance at 340 nm as an index. If the test polypeptide reduces absorbance at 340 nm even by a slight degree, the polypeptide is determined to have aldehyde dehydrogenase activity in which acetyl-CoA is used as a substrate.

In order to confirm that a polypeptide has an alcohol dehydrogenase activity in which acetaldehyde is used as a substrate, a test polypeptide is reacted with acetaldehyde under the coexistence of NADH, and decrease in absorbance at 340 nm is detected. Alcohol dehydrogenase produces ethanol from acetaldehyde which is accompanied by the conversion of NADH to NAD, and thus decrease in the amount of NADH is detected using decrease in absorbance at 340 nm as an index. Specifically, the method described in item "Examples" is carried out. If the test polypeptide reduces absorbance at 340 nm even by a slight degree, the polypeptide is determined to have alcohol dehydrogenase activity in which acetaldehyde is used as a substrate.

(3) Transformant Having Alanine Producing Ability

The present invention encompasses a transformant obtained by introducing (e) an alanine dehydrogenase gene, into a host bacterium of genus *Hydrogenophilus*. In other words, this transformant has an exogenous alanine dehydrogenase gene. Bacteria of the genus *Hydrogenophilus* produce an amount of alanine required for survival, however, this amount is insufficient for industrial utilization. The transformant of the present invention has been improved in alanine production due to the possession of the exogenous alanine dehydrogenase gene.

Examples of the alanine dehydrogenase gene include (e1) alanine dehydrogenase gene (alaD1) of *Geobacillus stearothermophilus*, alanine dehydrogenase gene (alaD2) of *Geobacillus stearothermophilus*, alanine dehydrogenase gene (alaD1) of *Thermus thermophilus*, and alanine dehydrogenase gene (alaD2) of *Thermus thermophilus*, which are preferable in that they have good alanine production efficiency.

The base sequence of *Geobacillus stearothermophilus* alaD1 is SEQ ID NO: 29, and the base sequence of *Geobacillus stearothermophilus* alaD2 is SEQ ID NO: 30. The base sequence of *Thermus thermophilus* alaD1 is SEQ ID NO: 31, and the base sequence of *Thermus thermophilus* alaD2 is SEQ ID NO: 32.

In particular, alaD2 of *Geobacillus stearothermophilus* (SEQ ID NO: 30) brings about especially high activity of alanine dehydrogenase within bacteria of the genus *Hydrogenophilus*, and thus is preferable.

In the present invention, (e2) DNA which consists of a base sequence having 95% or more, in particular 98% or more, in particular 99% or more identity with SEQ ID NO: 29, 30, 31, or 32, the DNA encoding a polypeptide having alanine dehydrogenase activity, can also be preferably used. In addition, (e3) DNA which hybridizes with a DNA consisting of a base sequence complementary to SEQ ID NO: 29, 30, 31, or 32 under stringent conditions, and which encodes a polypeptide having alanine dehydrogenase activity, can also be preferably used.

In the present invention, (e4) DNA which encodes a polypeptide consisting of an amino acid sequence of SEQ ID NO: 33, 34, 35, or 36 can be preferably used, in terms of good alanine production efficiency. Furthermore, (e5) DNA which encodes a polypeptide consisting of an amino acid sequence having 90% or more, in particular 95% or more, in particular 98% or more, in particular 99% or more identity with SEQ ID NO: 33, 34, 35, or 36, the polypeptide having alanine dehydrogenase activity, and (e6) DNA which encodes a polypeptide consisting of an amino acid sequence having a deletion, substitution, or addition of one or a plurality of amino acids in the amino acid sequence of SEQ ID NO: 33, 34, 35, or 36, the polypeptide having alanine dehydrogenase activity, can also be preferably used.

SEQ ID NO: 33 is the amino acid sequence of alanine dehydrogenase ALAD1 of *Geobacillus stearothermophilus*, and SEQ ID NO: 34 is the amino acid sequence of alanine dehydrogenase ALAD2 of *Geobacillus stearothermophilus*. SEQ ID NO: 35 is the amino acid sequence of alanine dehydrogenase ALAD1 of *Thermus thermophilus*, and SEQ ID NO: 36 is the amino acid sequence of alanine dehydrogenase ALAD2 of *Thermus thermophilus*.

In particular, alanine dehydrogenase ALAD2 of *Geobacillus stearothermophilus* is preferable.

In the present invention, it was found that a modified alanine dehydrogenase in which an N terminus portion of a maltose-binding protein (SEQ ID NO: 37) has been added to the N terminus of an alanine dehydrogenase, expresses a still higher activity in bacteria of the genus *Hydrogenophilus*. Therefore, the present invention provides a transformant obtained by introducing a DNA encoding the modified alanine dehydrogenase in which the N terminus portion of a maltose-binding protein (SEQ ID NO: 37) has been added to the N terminus of an alanine dehydrogenase (modified alanine dehydrogenase gene), into bacterium of the genus *Hydrogenophilus*. Namely, the present invention provides a transformant obtained by introducing the modified alanine dehydrogenase gene in which a DNA encoding the N terminus portion of a maltose-binding protein (SEQ ID NO: 38) has been added to the 5' end of an alanine dehydrogenase gene, into bacterium of the genus *Hydrogenophilus*.

In this case, the addition is carried out so that the C terminus of the N terminus portion of the maltose-binding protein is linked to the N terminus of the alanine dehydrogenase. Furthermore, the addition is carried out so that the 3' end of the DNA encoding the N terminus portion of the maltose-binding protein is linked to the 5' end of the alanine dehydrogenase gene.

In particular, polypeptides that have the N terminus portion of a maltose-binding protein (SEQ ID NO: 37) added to the N terminus of alanine dehydrogenase ALAD1 or ALAD2 of *Geobacillus stearothermophilus*, or alanine dehydrogenase ALAD1 or ALAD2 of *Thermus thermophilus* are preferable, and polypeptides that have the N terminus portion of the maltose-binding protein (SEQ ID NO: 37) added to the N terminus of alanine dehydrogenase ALAD2 of *Geobacillus stearothermophilus* (SEQ ID NO: 34) is more preferable.

In detail, (e7) DNA encoding a modified amino acid sequence in which an amino acid sequence of the N terminus portion of the maltose-binding protein (SEQ ID NO: 37) has been added to the N terminus of the amino acid sequence of SEQ ID NO: 33, 34, 35, or 36, can be preferably used for the transformation of bacteria of the genus *Hydrogenophilus*.

The amino acid sequence of the modified alanine dehydrogenase in which the N terminus portion of the maltose-binding protein (SEQ ID NO: 37) has been added to the N terminus of alanine dehydrogenase ALAD2 of *Geobacillus stearothermophilus* (SEQ ID NO: 34) is SEQ ID NO: 39.

Furthermore, (e8) DNA which encodes a polypeptide consisting of an amino acid sequence in which the amino acid sequence of the N terminus portion of a maltose-binding protein (SEQ ID NO: 37) has been added to the N terminus of an amino acid sequence having 90% or more, in particular 95% or more, in particular 98% or more, in particular 99% or more identity with SEQ ID NO: 33, 34, 35, or 36, the polypeptide having alanine dehydrogenase activity, and (e9) DNA which encodes a polypeptide consisting of an amino acid sequence in which the amino acid sequence of the N terminus portion of the maltose-binding protein (SEQ ID NO: 37) has been added to the N terminus of an amino acid sequence having a deletion, substitution, or addition of one or a plurality of amino acids in the amino acid sequence of SEQ ID NO: 33, 34, 35, or 36, the polypeptide having alanine dehydrogenase activity, can also be used.

(e10) DNA which consists of a base sequence in which the base sequence encoding the N terminus portion of the maltose-binding protein (SEQ ID NO: 38) has been added to the 5' end of the base sequence of SEQ ID NO: 29, 30, 31, or 32, can be used as well. In particular, DNA (SEQ ID NO: 40) which consists of a base sequence in which the base sequence of the N terminus portion of the maltose-binding protein (SEQ ID NO: 38) has been added to the 5' end of the base sequence of SEQ ID NO: 30, which is a base sequence of *Geobacillus stearothermophilus* alaD2, is preferable.

Furthermore, (e11) DNA which consists of a base sequence in which the base sequence encoding the N terminus portion of the maltose-binding protein (SEQ ID NO: 38) has been added to the 5' end of a base sequence having 90% or more, in particular 95% or more, in particular 98% or more, in particular 99% or more identity with SEQ ID NO: 29, 30, 31, or 32, the DNA encoding a polypeptide having alanine dehydrogenase activity, and (e12) DNA which consists of a base sequence in which the base sequence encoding the N terminus portion of the maltose-binding protein (SEQ ID NO: 38) has been added to the 5' end of a base sequence of a DNA which hybridizes with a DNA consisting of a base sequence complementary to SEQ ID NO: 29, 30, 31, or 32 under stringent conditions, and which encodes a polypeptide having alanine dehydrogenase activity, can be used as well.

The present invention encompasses a modified alanine dehydrogenase gene in which the polynucleotide (SEQ ID NO: 38) encoding the N terminus portion of the maltose-binding protein (SEQ ID NO: 37) has been added to the 5' end of an alanine dehydrogenase gene. Specific examples of the modified alanine dehydrogenase gene and preferable modified alanine dehydrogenase genes are as described with regard to the modified alanine dehydrogenase gene that is used for the transformation of bacteria of the genus *Hydrogenophilus*. The present invention also encompasses a vector comprising this modified alanine dehydrogenase gene (in particular, a vector that functions within bacteria of the genus *Hydrogenophilus*).

This modified alanine dehydrogenase gene and the vector comprising the gene can be preferably used for alanine production within bacteria of the genus *Hydrogenophilus*.

The present invention encompasses a modified alanine dehydrogenase in which the N terminus portion of the maltose-binding protein (SEQ ID NO: 37) has been added to the N terminus of an alanine dehydrogenase. Specific examples of the modified alanine dehydrogenase and preferable modified alanine dehydrogenases are as described with regard to the modified alanine dehydrogenase which is encoded by the modified alanine dehydrogenase gene that is used for the transformation of bacteria of the genus *Hydrogenophilus*.

This modified alanine dehydrogenase can be preferably used for alanine production within bacteria of the genus *Hydrogenophilus*, or can be used for alanine production by enzyme reaction.

In the present invention, in order to confirm that a polypeptide has an alanine dehydrogenase activity, a test polypeptide is reacted with pyruvic acid and ammonium chloride under the coexistence of NADH, and decrease in absorbance at 340 nm is detected. Alanine dehydrogenase produces alanine from pyruvic acid and ammonia, which is accompanied by the conversion of NADH to NAD, and thus decrease in the amount of NADH is detected using decrease in absorbance at 340 nm as an index. Specifically, the method described in item "Examples" is carried out. If the test polypeptide reduces the absorbance at 340 nm even by a slight degree, the polypeptide is determined to have alanine dehydrogenase activity.

In the present invention, a "homologue" of a certain DNA which encodes a polypeptide having a certain activity means a DNA which has a base sequence similar to the certain DNA (in particular, consisting of a base sequence having 90% or more identity with the base sequence of the certain DNA), and which encodes a polypeptide having the certain activity, or means a DNA which hybridizes with a DNA consisting of a base sequence complementary to the base sequence of the certain DNA under stringent conditions, and which encodes a polypeptide having the certain activity.

In the present invention, a "homologue" of a certain polypeptide having a certain activity means a polypeptide which has an amino acid sequence similar to the certain polypeptide (in particular, consisting of an amino acid sequence having 90% or more identity with the amino acid sequence of the certain polypeptide), and which has the certain activity, as well as a polypeptide which consists of an amino acid sequence in which one or a plurality of amino acids have been deleted, substituted, or added in the amino acid sequence of the certain polypeptide, and which has the certain activity.

(4) Methods for Producing Transformants

Next, methods for obtaining transformants by introducing the above-described genes for the production of isobutanol, the above-described genes for the production of ethanol or the above-described genes for the production of alanine, into bacteria of the genus *Hydrogenophilus* are explained.

Host

Examples of bacteria of the genus *Hydrogenophilus* include *Hydrogenophilus thermoluteolus, Hydrogenophilus halorhabdus, Hydrogenophilus denitrificans, Hydrogenophilus hirschii, Hydrogenophilus islandicus*, and strain Mar3 of bacteria of the genus *Hydrogenophilus* (*Hydrogenophilus* sp. Mar3). In particular, *Hydrogenophilus* thermoluteolus is preferable in that it possesses not only top-level growth rate but also top-level carbon dioxide fixation ability among carbon dioxide fixing microorganisms.

Bacteria of the genus *Hydrogenophilus* can be easily separated from everywhere on the earth. A preferable strain of *Hydrogenophilus thermoluteolus* include strain TH-1

(NBRC 14978). *Hydrogenophilus thermoluteolus* strain TH-1 (NBRC 14978) exhibits a top growth rate among carbon dioxide fixing microorganisms (Agricultural and Biological Chemistry, 41, 685-690 (1977)). *Hydrogenophilus thermoluteolus* strain NBRC 14978 is internationally deposited under the Budapest Treaty, and available to the public.

Transformation

Plasmid vectors for introducing the above-described DNAs into a host should contain a DNA which controls the autonomous replication function within bacteria of the genus *Hydrogenophilus*, and examples include broad-host-range vectors pRK415 (GenBank: EF437940.1), pBHR1 (GenBank: Y14439.1), pMMB67EH (ATCC 37622), pCAR1 (NCBI Reference Sequence: NC_004444.1), pC194 (NCBI Reference Sequence: NC_002013.1), pK18mobsacB (GenBank: FJ437239.1), pUB110 (NCBI Reference Sequence: NC_001384.1), and the like.

Examples of a preferable promoter include tac promoter, lac promoter, trc promoter, or each of promoters OXB1 and OXB11 to OXB20 from Oxford Genetics Ltd. Examples of a preferable terminator include rrnB T1T2 terminator of *Escherichia coli* rRNA operon, bacteriophage λt0 transcription terminator, and the like.

Transformation can be carried out by publicly known methods such as calcium chloride method, calcium phosphate method, DEAE-dextran transfection method, and electric pulse method.

Bacteria of the genus *Hydrogenophilus* grow under autotrophic conditions. However, since they can grow under heterotrophic conditions as well, the culture medium which is used to culture a host or transformant of a bacterium of the genus *Hydrogenophilus* can either be an inorganic culture medium or an organic culture medium. An organic culture medium comprising sugar, organic acids, amino acid, and the like can be used. The pH of the culture medium can be adjusted to approximately 6.2 to 8.

In any of the cases, culture can be carried out while supplying a mixed gas containing hydrogen, oxygen, and carbon dioxide, and preferably a mixed gas consisting of hydrogen, oxygen, and carbon dioxide. When using an organic culture medium, a mixed gas containing hydrogen, oxygen, and carbon dioxide, for example the air, can be used for aeration. When carbon dioxide gas is not supplied, a culture medium containing a carbonate as a carbon source can be used. Mixed gas can be entrapped within or continuously supplied into an airtight culture container, and can be dissolved into the culture medium by means of shaking culture. Alternatively, the culture container can be an airtight or open type, and mixed gas can be dissolved into the culture medium by bubbling.

The volume ratio of hydrogen, oxygen, and carbon dioxide within the supplied gas (hydrogen: oxygen: carbon dioxide) is preferably 1.75 to 7.5:1:0.25 to 3, more preferably 5 to 7.5:1:1 to 2, and further more preferably 6.25 to 7.5:1:1.5. Bacteria of the genus *Hydrogenophilus* are thermophilic bacteria, and thus the culture temperature is preferably 35 to 55° C., more preferably 37 to 52° C., and further more preferably 50 to 52° C.

(5) Method for Producing Isobutanol, Ethanol, or Alanine

When producing isobutanol, ethanol, or alanine using the transformant of bacterium of the genus *Hydrogenophilus* genus described above, the transformant can be cultured using an inorganic or organic culture medium while supplying a mixed gas containing hydrogen, oxygen, and carbon dioxide.

The supplied gas is preferably a mixed gas consisting of hydrogen, oxygen, and carbon dioxide. However, different kinds of gas can be mixed within, to the extent that isobutanol, ethanol, or alanine can be produced efficiently.

Bacteria of the genus *Hydrogenophilus* can grow using hydrogen as a source of energy and using carbon dioxide as a sole carbon source, and thus, carbon dioxide can be fixed efficiently particularly by producing the above-described compounds by using substantially only carbon dioxide (in particular, by using only carbon dioxide) as a carbon source. Therefore, using an inorganic culture medium that does not contain carbon sources such as organic substances and carbonates, namely, carrying out culture using substantially only carbon dioxide (in particular, using only carbon dioxide) as a carbon source is preferable. "Using substantially only carbon dioxide as a carbon source" encompasses cases in which an unavoidable amount of other carbon sources are mixed within. Furthermore, a culture medium containing organic substances such as sugar, organic acids, and amino acids, as well as carbonates, can also be used without supplying carbon dioxide.

The pH of the culture medium is preferably 6.2 to 8, more preferably 6.4 to 7.4, and further more preferably 6.6 to 7. When the pH is within this range, bacteria grow well and mixed gas dissolves well into the culture medium, and the target compound can be produced efficiently.

When batch culture is utilized, mixed gas can be entrapped within an airtight culture container and static culture or shaking culture can be carried out. When continuous culture is utilized, mixed gas can be continuously supplied into an airtight culture container and shaking culture can be carried out, or the transformant can be cultured using an airtight culture container while inducing mixed gas into the culture medium by bubbling. Shaking culture is preferable in that better dissolution of mixed gas into the culture medium can be achieved.

The volume ratio of hydrogen, oxygen, and carbon dioxide (hydrogen:oxygen:carbon dioxide) in the supplied gas is preferably 1.75 to 7.5:1:0.25 to 3, more preferably 5 to 7.5:1:1 to 2, and further more preferably 6.25 to 7.5:1:1.5. When the volume ratio is within this range, bacteria grow well, and the target compound can be produced efficiently.

The supply rate of mixed gas or raw material gas can be 10.5 to 60 L/hour, in particular 10.5 to 40 L/hour, in particular 10.5 to 21 L/hour, per 1 L of culture medium. When the supply rate is within this range, transformants grow well and the target compound can be produced efficiently, and the amount of wasted mixed gas can be reduced.

The culture temperature is preferably 35 to 55° C., more preferably 37 to 52° C., and further more preferably 50 to 52° C. When the temperature is within this range, transformants grow well, and the target compound can be produced efficiently.

Recovery of Target Compound

The target compound isobutanol, ethanol, or alanine is produced in the reaction solution by culturing in the above-described manner. Collecting the reaction solution will enable the recovery of the target compound, however, the target compound can furthermore be separated from the reaction solution by publicly known methods. Such publicly known methods with regard to ethanol and isobutanol include fractional distillation, extraction, and separation through ultrasonic atomization, and those with regard to alanine include various kinds of chromatography, and crystallization.

EXAMPLES (1) Construction of a Plasmid Vector

The method for constructing a plasmid vector that was commonly used to introduce genes for conferring isobutanol producing ability, genes for conferring ethanol producing ability, and genes for conferring alanine producing ability, is described below.

First, a broad-host-range vector pRK415 (GenBank: EF437940.1) (Gene, 70, 191-197 (1998)) was used as a template and PCR was performed. In order to amplify the DNA fragment of the plasmid region excluding the tetracycline gene region, a primer pair described below was synthesized and used. PCR was performed according to a conventional method using "DNA thermal cycler" manufactured by Life Technologies Inc., and using KOD FX Neo (manufactured by Toyobo Co., Ltd.) as a reaction reagent. Primers for the amplification of pRK415 plasmid sequence

```
(a-1)
                                      (SEQ ID NO: 42)
5'-CGTGGCCAACTAGGCCCAGCCAGATACTCCCGATC-3'

(b-1)
                                      (SEQ ID NO: 43)
5'-TGAGGCCTCATTGGCCGGAGCGCAACCCACTCACT-3'
```

A SfiI restriction site has been added to primers (a-1) and (b-1).

Plasmid pK18mobsacB (GenBank: FJ437239.1) (Gene, 145, 69-73 (1994)), which contains a neomycin/kanamycin resistance gene (hereinafter, the gene may be referred to as "nptII"), was used as a template and PCR was performed according to a conventional method. In the PCR, a primer pair described below was synthesized and used in order to amplify the DNA fragment containing the nptII gene sequence. PCR was performed according to a conventional method using "DNA thermal cycler" manufactured by Life Technologies Inc., and using KOD FX Neo (manufactured by Toyobo Co., Ltd.) as a reaction reagent.
Primers for the amplification of nptII gene sequence

```
(a-2)
                                      (SEQ ID NO: 44)
5'-ctgGGCCTAGTTGGCCacgtagaaagccagtccgc-3'

(b-2)
                                      (SEQ ID NO: 45)
5'-tccGGCCAATGAGGCCtcagaagaactcgtcaaga-3'
```

A SfiI restriction site has been added to primers (a-2) and (b-2).

The reaction solutions that were produced by each of the above-described PCR were subjected to electrophoresis using a 1% agarose gel, and as a result, a DNA fragment of approximately 8.7-kb was detected when pRK415 plasmid was used as a template, and a DNA fragment of approximately 1.1-kb was detected when nptII gene was used as a template.

Thus prepared DNA fragments were each cleaved by restriction enzyme SfiI, and reacted with a T4 DNA Ligase (manufactured by Takara Bio Inc.) to obtain a ligation solution. The obtained ligation solution was used to transform *Escherichia coli* JM109 by calcium chloride method (Journal of Molecular Biology, 53, 159-162 (1970)), and the transformants were applied onto LB agar media containing kanamycin. Viable strains on the culture media were cultured in a liquid culture medium by a conventional method, and plasmid DNA was extracted from the obtained culture solution. This plasmid DNA was cleaved by using restriction enzyme SfiI, and the inserted fragment was confirmed. As a result, a DNA fragment of the nptII gene sequence which was approximately 1.1-kb was observed in addition to DNA fragments of approximately 2.0-kb, 3.0-kb and 3.7-kb, which were derived from the pRK415 plasmid.

The constructed plasmid was named pCYK01.

(2) Construction of Cloning Vector Used for Gene Expression (2-1) Preparation of DNA Fragment of λt0 Terminator Sequence A primer pair described below was synthesized and used in PCR in order to prepare a DNA having λt0 terminator sequence. PCR was performed using "DNA thermal cycler" manufactured by Life Technologies Inc., and using KOD FX Neo (manufactured by Toyobo Co., Ltd.) as a reaction reagent. No template DNA was included since extension was carried out using each primer as the other's template.
Primers for the preparation of λt0 terminator sequence

```
(a-3)
                                      (SEQ ID NO: 46)
5'-GCATTAATccttggactcctgttgatagatccagtaatgacctcaga actccatctggatttgttcagaacgctcggttgccg-3'

(b-3)
                                      (SEQ ID NO: 47)
5'-caccgtgcagtcgatgGATctggattctcaccaataaaaaacgcccg gcggcaaccgagcgttctgaacaaatccagatggag-3'
```

The base sequences of the 3' ends of primers (a-3) and (b-3) are complementary to each other.

The produced reaction solution was subjected to electrophoresis using a 1% agarose gel, and as a result, a DNA fragment of approximately 0.13-kb, which corresponds to the λt0 terminator sequence, was detected.

(2-2) Preparation of a DNA Fragment of Tac Promoter Sequence

PCR was performed using plasmid pMAL-c5X (manufactured by New England Biolabs Inc.) containing a tac promoter, as a template. In the PCR, a primer pair described below was synthesized and used in order to amplify tac promoter sequence. PCR was performed according to a conventional method using "DNA thermal cycler" manufactured by Life Technologies Inc., and using KOD FX Neo (manufactured by Toyobo Co., Ltd.) as a reaction reagent.
Primers for the amplification of tac promoter sequence

```
(a-4)
                                      (SEQ ID NO: 48)
5'-TTATTGGTGAGAATCCAGATCCATCGACTGCACGGTGCACCAATGCT

TCT-3'

(b-4)
                                      (SEQ ID NO: 49)
5-gcaagcttggagtgatcatcgtATGCATATGCGTTTCTCCTCCAGATCC ctgtttcctgtgtgaaattgt-3'
```

The produced reaction solution was subjected to electrophoresis using a 1% agarose gel, and as a result, a DNA fragment of approximately 0.3-kb, which corresponds to tac promoter sequence, was detected.

(2-3) Introduction of λt0 Terminator and Tac Promoter Sequences

The DNA fragments that were prepared in the above-described (2-1) and (2-2) were cut out from the agarose gel, and DNA was recovered from the gel by freezing and melting the gel. The recovered DNA fragments corresponding to λt0 terminator sequence and the tac promoter sequence were mixed and used as templates, and overlap extension PCR was performed. In the overlap extension PCR, a combination of the above-described primers (a-3) and (b-4) was used in order to prepare a DNA in which the tac promoter is linked downstream of λt0 terminator. The base sequences of the 5' ends of the primers (b-3) and (a-4), which were used in amplifying the template DNA fragments, are complementary with each other. PshBI and HindIII restriction sites have been added to primers (a-3) and (b-4), respectively.

The produced reaction solution was subjected to electrophoresis using a 1% agarose gel, and as a result, a DNA fragment of approximately 0.4-kb, which corresponds to the DNA in which the tac promoter is linked downstream of λt0 terminator, was detected.

The approximately 0.4-kb DNA fragment that was amplified by PCR, in which the tac promoter is linked downstream of the λt0 terminator, and the above-mentioned approximately 9.8-kb DNA fragment of cloning vector pCYK01, were cleaved by the restriction enzymes PshBI and HindIII. The cleaved DNA fragments were linked to each other using a T4 DNA Ligase (manufactured by Takara Bio Inc.).

The obtained ligation solution was used to transform *Escherichia coli* JM109 by calcium chloride method, and the transformants were applied onto LB agar media containing kanamycin. Viable strains on the culture media were cultured in a liquid culture medium by a conventional method, and plasmid DNA was extracted from the obtained culture solution. This plasmid DNA was cleaved by using restriction enzymes PshBI and HindIII, and the inserted fragment was confirmed. As a result, a DNA fragment of approximately 0.4-kb, in which tac promoter is linked downstream of λt0 terminator, was observed in addition to a DNA fragment of approximately 9.6-kb from plasmid pCYK01.

(2-4) Introduction of rrnB T1T2 Bidirectional Terminator (Hereinafter, May be Referred to as "rrnB Terminator")

PCR was performed using plasmid pMAL-c5X (manufactured by New England Biolabs Inc.) containing rrnB terminator sequence as a template. In the PCR, a primer pair described below was synthesized and used in order to amplify rrnB terminator sequence. PCR was performed according to a conventional method using "DNA thermal cycler" manufactured by Life Technologies Inc., and using KOD FX Neo (manufactured by Toyobo Co., Ltd.) as a reaction reagent.

Primers for the amplification of rrnB terminator sequence

```
(a-5)
                                     (SEQ ID NO: 50)
5'-ctcgaattcactggccgtcgttttacaacgtcgtg-3'

(b-5)
                                     (SEQ ID NO: 51)
5'-CGCAATTGAGTTTGTAGAAACGCAAAAAGGCCATC-3'
```

EcoRI and MunI restriction sites have been added to primers (a-5) and (b-5), respectively.

The produced reaction solution was subjected to electrophoresis using a 1% agarose gel, and as a result, a DNA fragment of approximately 0.6-kb, which corresponds to rrnB terminator sequence, was detected.

The approximately 0.6-kb DNA fragment containing rrnB terminator sequence, which was amplified by the above-described PCR, was cleaved by restriction enzymes EcoRI and MunI, and the approximately 10.0-kb DNA fragment of the plasmid that was constructed in the above-described (2-3) was cleaved using restriction enzyme EcoRI. The cleaved DNA fragments were linked to each other using a T4 DNA Ligase (manufactured by Takara Bio Inc.).

The obtained ligation solution was used to transform *Escherichia coli* JM109 by calcium chloride method, and the obtained transformants were applied onto LB agar media containing kanamycin. Viable strains on the culture media were cultured in a liquid culture medium by a conventional method, and plasmid DNA was extracted from the obtained culture solution. This plasmid was cleaved by using restriction enzymes EcoRI and MunI, and the inserted fragment was confirmed. As a result, a DNA fragment of approximately 0.6-kb which corresponds to rrnB terminator sequence was observed in addition to a DNA fragment of approximately 10.0-kb from the above-described plasmid of (2-3).

The constructed cloning vector for gene expression was named pCYK21.

(3) Transformant Having Isobutanol Producing Ability (3-1) Codon Optimization of the 2-Keto-Acid Decarboxylase Gene of *Lactococcus lactis*

Codon usage of kivD gene encoding the 2-keto-acid decarboxylase of *Lactococcus lactis* was optimized according to the codon usage frequency of *Hydrogenophilus thermoluteolus* strain TH-1 (NBRC 14978), and the DNA fragment of the optimized base sequence (SEQ ID NO: 1) was synthesized by GenScript Japan Inc.

The approximately 1.7-kb DNA fragment of the codon-optimized gene that was synthesized, and the above-mentioned DNA fragment of approximately 10.6-kb from cloning vector pCYK21 were each cleaved by using restriction enzymes NdeI and HindIII. The cleaved DNA fragments were linked to each other using a T4 DNA Ligase (manufactured by Takara Bio Inc.).

The obtained ligation solution was used to transform *Hydrogenophilus thermoluteolus* strain TH-1 (NBRC 14978) by electric pulse method (electroporation method), and the transformants were applied onto A-solid medium [$(NH_4)_2SO_4$ 3.0 g, $KH_2PO_4$ 1.0 g, $K_2HPO_4$ 2.0 g, NaCl 0.25 g, $FeSO_4 \cdot 7H_2O$ 0.014 g, $MgSO_4 \cdot 7H_2O$ 0.5 g, $CaCl_2$ 0.03 g, $MoO_3$ 4.0 mg, $ZnSO_4 \cdot 7H_2O$ 28 mg, $CuSO_4 \cdot 5H_2O$ 2.0 mg, $H_3BO_3$ 4.0 mg, $MnSO_4 \cdot 5H_2O$ 4.0 mg, $CoCl_2 \cdot 6H_2O$ 4.0 mg, agar 15 g were dissolved in 1 L of distilled water (pH 7.0)] containing kanamycin at 50 μg/ml, and incubated at 50° C. for 60 hours in a chamber that was filled with a mixed gas of $H_2:O_2:CO_2=7.5:1:1.5$.

Viable strains on the A-solid medium were inoculated using a platinum loop into a test tube containing 5 ml of A-liquid medium [$(NH_4)_2SO_4$ 3.0 g, $KH_2PO_4$ 1.0 g, $K_2HPO_4$ 2.0 g, NaCl 0.25 g, $FeSO_4 \cdot 7H_2O$ 0.014 g, $MgSO_4 \cdot 7H_2O$ 0.5 g, $CaCl_2$ 0.03 g, $MoO_3$ 4.0 mg, $ZnSO_4 \cdot 7H_2O$ 28 mg, $CuSO_4 \cdot 5H_2O$ 2.0 mg, $H_3BO_3$ 4.0 mg, $MnSO_4 \cdot 5H_2O$ 4.0 mg, $CoCl_2 \cdot 6H_2O$ 4.0 mg were dissolved in 1 L of distilled water (pH 7.0)] containing kanamycin at 50 μg/ml. The test tubes were filled with a mixed gas of $H_2:O_2:CO_2=7.5:1:1.5$, and subjected to shaking culture at 50° C., and plasmid DNA was extracted from the obtained culture solution. The plasmid was cleaved using restriction enzymes NdeI and HindIII, and the inserted fragment was confirmed. As a result, a DNA fragment of approximately 1.7-kb of the codon-optimized gene was observed in addition to a DNA fragment of approximately 10.6-kb from plasmid pCYK21.

The plasmid containing the codon-optimized *Lactococcus lactis* kivD gene was named pC-opt-kivD. The recombinant strain of *Hydrogenophilus* thermoluteolus which possesses pC-opt-kivD was named strain KDC01.

(3-2) Cloning of 2-Keto-Acid Decarboxylase Gene for Comparison Examples

Genomic DNAs were extracted from *Lactococcus lactis* NBRC 100933, *Bacillus subtilis* NBRC 13719, *Geobacillus thermoglucosidasius* NBRC 107763, *Geobacillus thermodenitrificans* ATCC 29492, and *Klebsiella pneumoniae* NBRC 14940 according to a conventional method.

A DNA fragment containing 2-keto-acid decarboxylase kivD gene of *Lactococcus lactis*, a DNA fragment containing acetolactate synthase alsS gene of *Bacillus subtilis*, the acetolactate synthase having 2-keto-acid decarboxylase activity, a DNA fragment containing acetolactate synthase Geoth 3495 gene of *Geobacillus thermoglucosidasius*, the acetolactate synthase having a 2-keto-acid decarboxylase activity, a DNA fragment containing acetolactate synthase Gtng 0348 gene of *Geobacillus thermodenitrificans*, the acetolactate synthase having a 2-keto-acid decarboxylase activity, and a DNA fragment containing indolepyruvate decarboxylase ipdC gene of *Klebsiella pneumoniae*, the indolepyruvate decarboxylase having a 2-keto-acid decarboxylase activity were amplified by PCR method using the 5-kind genomic DNAs described above, respectively.

The following primers were used for PCR. PCR was performed according to a conventional method using "DNA thermal cycler" manufactured by Life Technologies Inc., and using KOD FX Neo (manufactured by Toyobo Co., Ltd.) as a reaction reagent.

Primers for the amplification of *Lactococcus lactis* kivD gene (a-6)
(SEQ ID NO: 52)
5'-GCACATATGTATACAGTAGGAGATTACCTATTAGA-3'

(b-6)
(SEQ ID NO: 53)
5'-GCAGGATCCTTATGATTTATTTTGTTCAGCAAATA-3'

An NdeI restriction site has been added to primer (a-6), and a BamHI restriction site has been added to primer (b-6).

Primers for the amplification of *Bacillus subtilis* alsS gene (a-7)
(SEQ ID NO: 54)
5'-GCACATATGACAAAAGCAACAAAAGAACAAAAATC-3'

(b-7)
(SEQ ID NO: 55)
5'-GCAGGATCCTAGAGAGCTTTCGTTTTCATGAGTTC-3'

An NdeI restriction site has been added to primer (a-7), and a BamHI restriction site has been added to primer (b-7).

Primers for the amplification of *Geobacillus thermoglucosidasius* Geoth_3495 gene (a-8)
(SEQ ID NO: 56)
5'-CGAGTCCATATGAAACAGACTATCCGCAATATCAG-3'

(b-8)
(SEQ ID NO: 57)
5'-GCAGGATCCTTACCGAGAATTCGAGCGCTTTCGCA-3'

An NdeI restriction site has been added to primer (a-8), and a BamHI restriction site has been added to primer (b-8).

Primers for the amplification of *Geobacillus thermodenitrificans* Gtng_0348 gene (a-9)
(SEQ ID NO: 58)
5'-CGAGTCCATATGAAAAAGCGGGTGATGCGTGGCCT-3'

(b-9)
(SEQ ID NO: 59)
5'-GCAGGATCCTCATCTGTCTGACAGTCTCATCGTCA-3'

An NdeI restriction site has been added to primer (a-9), and a BamHI restriction site has been added to primer (b-9).

Primers for the amplification of *Klebsiella pneumoniae* ipdC gene (a-10)
(SEQ ID NO: 60)
5'-CGAGTCCATATGCAACCGACCTACACTATTGGGGA-3'

(b-10)
(SEQ ID NO: 61)
5'-CGCGGATCCTTAAACGCGGCTGTTTCGCTCCTCAA-3'

An NdeI restriction site has been added to primer (a-10), and a BamHI restriction site has been added to primer (b-10).

The produced reaction solutions were subjected to electrophoresis using a 1% agarose gel, and DNA fragments of approximately 1.7-kb were detected with regard to each of *Lactococcus lactis* kivD gene, *Bacillus subtilis* alsS gene, *Geobacillus thermoglucosidasius* Geoth 3495 gene, *Geobacillus thermodenitrificans* Gtng 0348 gene, and *Klebsiella pneumoniae* ipdC gene.

The approximately 1.7-kb DNA fragments, each containing *Lactococcus lactis* kivD gene, *Bacillus subtilis* alsS gene, *Geobacillus thermoglucosidasius* Geoth 3495 gene, *Geobacillus thermodenitrificans* Gtng 0348 gene, or *Klebsiella pneumoniae* ipdC gene, which were amplified by the above-mentioned PCR were cleaved by using restriction enzymes NdeI and HindIII. The above-described approximately 10.6-kb DNA fragment of cloning vector pCYK21 was also cleaved by using restriction enzymes NdeI and HindIII. Each of the 5 cleaved 1.7-kb DNA fragments and the 10.6-kb DNA fragment were linked to each other using a T4 DNA Ligase (manufactured by Takara Bio Inc.).

The obtained ligation solutions were used to transform *Hydrogenophilus thermoluteolus* strain TH-1 (NBRC 14978) by electric pulse method, and the obtained transformants were applied onto A-solid medium containing kanamycin at 50 µg/ml, and incubated at 50° C. for 60 hours in a chamber that was filled with a mixed gas of $H_2:O_2:CO_2=7.5:1:1.5$.

Each of the viable strains on the A-solid medium was inoculated using a platinum loop into a test tube containing 5 ml of A-liquid medium containing kanamycin at 50 µg/ml. The test tubes were filled with a mixed gas of $H_2:O_2:CO_2=7.5:1:1.5$, and subjected to shaking culture at 50° C., and plasmid DNAs were extracted from the culture solution. The plasmids were cleaved by using restriction enzymes NdeI and BamHI, and the inserted fragments were confirmed. As a result, DNA fragments each of approximately 1.7-kb in length, which were from *Lactococcus lactis* kivD gene, *Bacillus subtilis* alsS gene, *Geobacillus thermoglucosidasius* Geoth_3495 gene, *Geobacillus thermodenitrificans* Gtng 0348 gene, and *Klebsiella pneumoniae* ipdC gene in addition to an approximately 10.6-kb DNA fragment of plasmid pCYK21 were observed.

The plasmid containing *Lactococcus lactis* kivD gene was named pC-Lla-kivD, the plasmid containing *Bacillus subtilis* alsS gene was named pC-Bsu-alsS, the plasmid containing *Geobacillus thermoglucosidasius* Geoth_3495 gene was named pC-Gtg-3495, the plasmid containing *Geobacillus thermodenitrificans* Gtng_0348 gene was named pC-Gtd-0348, and the plasmid containing *Klebsiella pneumoniae* ipdC gene was named pC-Kpn-ipdC.

(3-3) Cloning of Alcohol Dehydrogenase Gene

Genomic DNAs were extracted from *Klebsiella pneumoniae* NBRC 14940, *Geobacillus thermocatenulatus* NBRC 15316, and *Geobacillus thermoglucosidasius* NBRC 107763 according to a conventional method.

The 3 genomic DNAs described above were each used as templates to amplify a DNA fragment containing alcohol dehydrogenase gene adhP of *Klebsiella pneumoniae*, a DNA fragment containing alcohol dehydrogenase gene adhP of *Geobacillus thermocatenulatus*, a DNA fragment containing alcohol dehydrogenase gene adhP of *Geobacillus thermoglucosidasius*, and a DNA fragment containing alcohol dehydrogenase gene adhA of *Geobacillus thermoglucosidasius*, respectively, by PCR method. The following primers were used for PCR. PCR was performed according to a conventional method using "DNA thermal cycler" manufactured by Life Technologies Inc., and using KOD FX Neo (manufactured by Toyobo Co., Ltd.) as a reaction reagent.

Primers for the amplification of *Klebsiella pneumoniae* adhP gene

```
(a-11)
                                        (SEQ ID NO: 62)
5'-CGAGTCCATATGAAGGCAGCTGTTGTTACCCACGA-3'

(b-11)
                                        (SEQ ID NO: 63)
5'-CGCGAATTCTTAGCTACGCAGATCGATAACCATAC-3'
```

An NdeI restriction site has been added to primer (a-11), and an EcoRI restriction site has been added to primer (b-11).

Primers for the amplification of *Geobacillus thermocatenulatus* adhP gene

```
(a-12)
                                        (SEQ ID NO: 64)
5'-CGAGTCCATATGAAAGCCGCCGTTGTTCACAAATT-3'

(b-12)
                                        (SEQ ID NO: 65)
5'-GCAGGATCCTTACATTGTTAAAACAATGCGGCCAT-3'
```

An NdeI restriction site has been added to primer (a-12), and a BamHI restriction site has been added to primer (b-12).

Primers for the amplification of *Geobacillus thermoglucosidasius* adhP gene

```
(a-13)
                                        (SEQ ID NO: 66)
5'-CGAGTCCATATGAAAGCGGCAGTTGTCAACGATTT-3'

(b-13)
                                        (SEQ ID NO: 67)
5'-CGCGAATTCTTAACGGTTGACACCGATGGTTAAAA-3'
```

An NdeI restriction site has been added to primer (a-13), and an EcoRI restriction site has been added to primer (b-13).

Primers for the amplification of *Geobacillus thermoglucosidasius* adhA gene

```
(a-14)
                                        (SEQ ID NO: 68)
5'-CGAGTCCATATGAAAGCACTTACATACCTAGGGCC-3'

(b-14)
                                        (SEQ ID NO: 69)
5'-GCAGGATCCTTAACTGTTGGAAATAATGACTTTTA-3'
```

An NdeI restriction site has been added to primer (a-14), and a BamHI restriction site has been added to primer (b-14).

The produced reaction solutions were subjected to electrophoresis using a 1% agarose gel, and DNA fragments of approximately 1.0-kb were detected with regard to each of *Klebsiella pneumoniae* adhP gene, *Geobacillus thermocatenulatus* adhP gene, *Geobacillus thermoglucosidasius* adhP gene, and *Geobacillus thermoglucosidasius* adhA gene.

The approximately 1.0-kb DNA fragments containing each of *Geobacillus thermocatenulatus* adhP gene and *Geobacillus thermoglucosidasius* adhA gene, that were amplified by the above-described PCR, were cleaved by using restriction enzymes NdeI and BamHI. The above-mentioned approximately 10.6-kb DNA fragment of cloning vector pCYK21 was also cleaved by using restriction enzymes NdeI and BamHI. Each of the cleaved 1.0-kb DNA fragments and the 10.6-kb DNA fragment were linked to each other using a T4 DNA Ligase (manufactured by Takara Bio Inc.).

The approximately 1.0-kb DNA fragments containing each of *Klebsiella pneumoniae* adhP gene and *Geobacillus thermoglucosidasius* adhP gene, that were amplified by PCR, were cleaved by using restriction enzymes NdeI and EcoRI. The above-mentioned approximately 10.6-kb DNA fragment of cloning vector pCYK21 was also cleaved by using restriction enzymes NdeI and EcoRI. Each of the cleaved 1.0-kb DNA fragments and the 10.6-kb DNA fragment were linked to each other using a T4 DNA Ligase (manufactured by Takara Bio Inc.).

The obtained ligation solutions were used to transform *Hydrogenophilus thermoluteolus* strain TH-1 (NBRC 14978) by electric pulse method, and the obtained transformants were applied onto A-solid medium containing kanamycin at 50 μg/ml, and incubated at 50° C. for 60 hours in a chamber that was filled with a mixed gas of $H_2:O_2:CO_2=7.5:1:1.5$.

Each of the viable strains on the A-solid medium was inoculated using a platinum loop into a test tube containing 5 ml of A-liquid medium containing kanamycin at 50 μg/ml. The test tubes were filled with a mixed gas of $H_2:O_2:CO_2=7.5:1:1.5$, and subjected to shaking culture at 50° C., and plasmid DNAs were extracted from the culture solution. The plasmids were cleaved using restriction enzymes NdeI and BamHI, or NdeI and EcoRI, and the inserted fragments were confirmed. As a result, fragments of approximately 1.0-kb in length which were each inserted fragments of *Klebsiella pneumoniae* adhP gene, *Geobacillus thermocatenulatus* adhP gene, *Geobacillus thermoglucosidasius* adhP gene, and *Geobacillus thermoglucosidasius* adhA gene, in addition to an approximately 10.6-kb DNA fragment of plasmid pCYK21 were observed.

The plasmid containing *Klebsiella pneumoniae* adhP gene was named pC-Kpn-adhP, the plasmid containing *Geobacillus thermocatenulatus* adhP gene was named pC-Gtc-adhP, the plasmid containing *Geobacillus thermoglucosidasius* adhP gene was named pC-Gtg-adhP, and the plasmid containing *Geobacillus thermoglucosidasius* adhA gene was named pC-Gtg-adhA.

The plasmids possessed by the recombinant strains of *Hydrogenophilus thermoluteolus* are shown in Table 1.

TABLE 1

| Strain | Plasmid | Transgene |
|---|---|---|
| KDC01 | pC-opt-kivD | Codon-optimized kivD (*Lactococcus lactis*) |
| KDC02 | pC-Lla-kivD | kivD (*Lactococcus lactis*) |
| KDC03 | pC-Bsu-alsS | alsS (*Bacillus subtilis*) |
| KDC04 | pC-Gtg-3495 | Geoth_3495 (*Geobacillus thermoglucosidasius*) |
| KDC05 | pC-Gtd-0348 | Gtng_0348 (*Geobacillus thermodenitrificans*) |
| KDC06 | pC-Kpn-ipdC | ipdc (*Klebsiella pneumoniae*) |
| ADH01 | pC-Kpn-adhP | adhP (*Klebsiella pneumoniae*) |
| ADH02 | pC-Gtc-adhP | adhP (*Geobacillus thermocatenulatus*) |
| ADH03 | pC-Gtg-adhP | adhP (*Geobacillus thermoglucosidasius*) |
| ADH04 | pC-Gtg-adhA | adhA (*Geobacillus thermoglucosidasius*) |

(3-4) Confirmation of Transgene Expression in *Hydrogenophilus* Thermoluteolus Strain into which Isobutanol Producing Gene has been Introduced
Measurement of 2-Keto-Acid Decarboxylase Activity Each 2-keto-acid decarboxylase gene-introduced strain that was obtained as described above, was inoculated using a platinum loop into a test tube containing 5 ml of A-liquid medium containing kanamycin at 50 µg/ml. The test tubes were filled with a mixed gas of $H_2:O_2:CO_2=7.5:1:1.5$, and subjected to shaking culture at 50° C. for 20 hours.

Bacterial cells thus cultured and proliferated were collected by centrifugation (4° C., 15,000 rpm, 1 minute). The bacterial cells were disrupted by sonication, and subsequently centrifuged (4° C., 15,000 rpm, 5 minutes) to obtain a cell disruption supernatant. The cell disruption supernatant was used as a crude enzyme solution to measure 2-keto-acid decarboxylase activity by the following method. Crude enzyme solution, 50 mM Tris-HCl (pH 6.8), 2.5 mM $MgSO_4$, 0.2 mM thiamine pyrophosphate (TPP), 3.0 mM NADH, 30 mM 2-ketoisovalerate, and 0.5 U/ml horse-derived alcohol dehydrogenase (Sigma-Aldrich Japan G.K.) were mixed, reacted at 50° C., and decrease in absorbance at 340 nm coming from NADH was traced, and the initial rate of reaction was analyzed. Specific activity was calculated from the initial rate of reaction and protein concentration. The enzyme level for producing 1 µmol of isobutyraldehyde per minute was defined as 1 U (Unit).

As a result, 0.65 U/mg of 2-keto-acid decarboxylase activity of interest was detected in strain KDC01, into which a codon-optimized kivD of *Lactococcus lactis* was introduced.

On the other hand, no 2-keto-acid decarboxylase activity was observed in strain KDC02 into which natural form kivD of *Lactococcus lactis* was introduced, strain KDC03 into which *Bacillus subtilis* alsS was introduced, strain KDC04 into which *Geobacillus thermoglucosidasius* Geoth_3495 was introduced, strain KDC05 into which *Geobacillus thermodenitrificans* Gtng_0348 was introduced, and strain KDC06 into which *Klebsiella pneumoniae* ipdC was introduced.

No 2-keto-acid decarboxylase activity was observed as a result of conducting the same experiment with regard to *Hydrogenophilus* thermoluteolus strain TH-1 into which an empty vector (pCYK21) was introduced.
Measurement of Activity of an Alcohol Dehydrogenase that Uses Isobutyraldehyde as a Substrate Each alcohol dehydrogenase gene-introduced strain of *Hydrogenophilus thermoluteolus* that was obtained as described above was inoculated using a platinum loop into a test tube containing 5 ml of A-liquid medium containing kanamycin at 50 µg/ml. The test tubes were filled with a mixed gas of $H_2:O_2:CO_2=7.5:1:1.5$, and subjected to shaking culture at 50° C. for 20 hours.

Bacterial cells thus cultured and proliferated were collected by centrifugation (4° C., 15,000 rpm, 1 minute). The bacterial cells were disrupted by sonication, and subsequently centrifuged (4° C., 15,000 rpm, 5 minutes) to obtain a cell disruption supernatant. The cell disruption supernatant was used as a crude enzyme solution to measure alcohol dehydrogenase activity by the following method. Crude enzyme solution, 50 mM Tris-HCl (pH 8.0), 0.2 mM NADH, and 100 mM isobutyraldehyde were mixed, reacted at 50° C., and decrease in absorbance at 340 nm coming from NADH was traced, and the initial rate of reaction was analyzed. Specific activity was calculated from the initial rate of reaction and protein concentration. The enzyme level for producing 1 µmol of isobutanol per minute was defined as 1 U (Unit).

As a result, activity was observed in all transformants into which any of *Klebsiella pneumoniae* adhP gene, *Geobacillus thermocatenulatus* adhP gene, *Geobacillus thermoglucosidasius* adhP gene, or *Geobacillus thermoglucosidasius* adhA gene was introduced, as shown in Table 2. On the other hand, no alcohol dehydrogenase activity was observed as a result of conducting the same experiment with regard to *Hydrogenophilus* thermoluteolus strain TH-1 into which an empty vector (pCYK21) was introduced.

TABLE 2

Activities of alcohol dehydrogenases that use isobutyraldehyde as a substrate, in adhP or adhA transgenic strains of *Hydrogenophilus thermoluteolus*

| Strain | Plasmid | Transgene | Alcohol dehydrogenase activity (U/mg-protein) |
|---|---|---|---|
| ADH01 | pC-Kpn-adhP | adhP (*Klebsiella pneumoniae*) | 5.2 |
| ADH02 | pC-Gtc-adhP | adhP (*Geobacillus thermocatenulatus*) | 4.3 |
| ADH03 | pC-Gtg-adhP | adhP (*Geobacillus thermoglucosidasius*) | 4.5 |
| ADH04 | pC-Gtg-adhA | adhA (*Geobacillus thermoglucosidasius*) | 3.1 |
| pCYK21/ TH-1 | pCYK21 | None | ND (Undetectable) |

(3-5) Production of Isobutanol Producing Strain

A DNA fragment which contains adhP gene encoding the alcohol dehydrogenase of *Klebsiella pneumoniae* was amplified according to a conventional method using PCR, in which "DNA thermal cycler" manufactured by Life Technologies Inc. was used and KOD FX Neo (manufactured by Toyobo Co., Ltd.) was used as a reaction reagent. Plasmid pC-Kpn-adhP was used as a template DNA, and the following primer pair was used.
Primers for the amplification of *Klebsiella pneumoniae* adhP gene (a-15)
                                              (SEQ ID NO: 70)
5'-CGC<u>GGTACC</u>GGATCTGGAGGAGAAACGCATATGAA-3'

(b-15)
                                              (SEQ ID NO: 71)
5'-CGC<u>GGTACC</u>TTAACGGTTGACACCGATGGTTAAAA-3'

A KpnI restriction site has been added to primers (a-15) and (b-15).

The produced reaction solution was subjected to electrophoresis using a 1% agarose gel, and as a result, a DNA fragment of approximately 1.0-kb of *Klebsiella pneumoniae* adhP gene was detected.

The DNA fragment containing adhP gene encoding the alcohol dehydrogenase of *Klebsiella pneumoniae* that was obtained as described above, and the above-mentioned approximately 12.3-kb DNA fragment of plasmid pC-opt-kivD which contains the codon-optimized *Lactococcus lactis* kivD gene, were each cleaved using restriction enzyme KpnI. The cleaved DNA fragments were linked to each other using a T4 DNA Ligase (manufactured by Takara Bio Inc.).

The obtained ligation solution was used to transform *Hydrogenophilus thermoluteolus* strain TH-1 (NBRC 14978) by electric pulse method, and the obtained transformants were applied onto A-solid medium containing kanamycin at 50 µg/ml, and incubated at 50° C. for 60 hours in a chamber that was filled with a mixed gas of $H_2:O_2:CO_2=7.5:1:1.5$.

Viable strains on the A-solid medium were inoculated using a platinum loop into a test tube containing 5 ml of A-liquid medium containing kanamycin at 50 µg/ml. The test tube was filled with a mixed gas of $H_2:O_2:CO_2=7.5:1:1.5$, and subjected to shaking culture at 50° C. Plasmid DNA was extracted from the culture medium, the plasmid was cleaved using restriction enzyme KpnI, and the inserted fragment was confirmed. As a result, an approximately 1.0-kb inserted fragment of *Klebsiella pneumoniae* adhP gene was observed in addition to an approximately 12.3-kb DNA fragment of plasmid pC-opt-kivD.

The plasmid containing *Klebsiella pneumoniae* adhP gene downstream of the codon-optimized *Lactococcus lactis* kivD gene was named pC-opt-kivD&Kpn-adhP.

In addition, this strain of *Hydrogenophilus thermoluteolus* was named strain IBU-1.

(3-6) Production of Isobutanol

*Hydrogenophilus thermoluteolus* strain (IBU-1) obtained in the above item (3-5) into which an isobutanol producing gene was introduced, was inoculated using a platinum loop into A-liquid medium containing kanamycin at 50 µg/ml, and subjected to shaking culture at 50° C. for 30 hours while supplying a mixed gas of $H_2:O_2:CO_2=7.5:1:1.5$ during incubation.

Following incubation, a culture supernatant was obtained by centrifugation (4° C., 15,000 rpm, 1 minute), and isobutanol in the culture supernatant was quantified. As a result, production of 4 mM of isobutanol was confirmed in the culture supernatant.

(4) Transformant Having Ethanol Producing Ability (4-1) Cloning of Pyruvate Decarboxylase Gene Genomic DNAs were extracted from *Gluconobacter oxydans* NBRC 3292, *Zymomonas mobilis* NBRC 13756, *Zymobacter palmae* NBRC 102412, and *Acetobacter pasteurianus* NBRC 105184, respectively, according to a conventional method.

Using each of the above-described 4-kind genomic DNAs as a template, DNA fragments containing pyruvate decarboxylase pdc genes of *Gluconobacter oxydans, Zymomonas mobilis, Zymobacter palmae*, and *Acetobacter pasteurianus* were amplified, respectively, by PCR method. The following primers were used for PCR. PCR was performed according to a conventional method using "DNA thermal cycler" manufactured by Life Technologies Inc., and using KOD FX Neo (manufactured by Toyobo Co., Ltd.) as a reaction reagent.

Primers for the amplification of *Gluconobacter oxydans* pdc gene (a-16)
(SEQ ID NO: 72)
5'-GCA<u>CATATG</u>ACTTATACTGTCGGACATTATCTTGC-3'

(b-16)
(SEQ ID NO: 73)
5'-GCA<u>GGATCC</u>TTAGACGCTCTGGGGCTTGCGGGAGT-3'

An NdeI restriction site has been added to primer (a-16), and a BamHI restriction site has been added to primer (b-16).

Primers for the amplification of *Zymomonas mobilis* pdc gene (a-17)
(SEQ ID NO: 74)
5'-CGAGTC<u>CATATG</u>AAGGCAGCTGTTGTTACCCACGA-3'

(b-17)
(SEQ ID NO: 75)
5'-CGC<u>GTCGAC</u>TTAGCTACGCAGATCGATAACCATAC-3'

An NdeI restriction site has been added to primer (a-17), and a SalI restriction site has been added to primer (b-17).

Primers for the amplification of *Zymobacter palmae* pdc gene (a-18)
(SEQ ID NO: 76)
5'-GCA<u>CATATG</u>TATACCGTTGGTATGTACTTGGCAGA-3'

(b-18)
(SEQ ID NO: 77)
5'-GCA<u>GTCGAC</u>TTACGCTTGTGGTTTGCGAGAGTTGG-3'

An NdeI restriction site has been added to primer (a-18), and a SalI restriction site has been added to primer (b-18).

Primers for the amplification of *Acetobacter* pasteurianus pdc gene (a-19)
(SEQ ID NO: 78)
5'-GCA<u>CATATG</u>ACATATACAGTCGGCATGTATCTTGC-3'

(b-19)
(SEQ ID NO: 79)
5'-GCA<u>GTCGAC</u>TCAGGATACCTGCGGTTTTCTGGAAT-3'

An NdeI restriction site has been added to primer (a-19), and a SalI restriction site has been added to primer (b-19).

The produced reaction solutions were subjected to electrophoresis using a 1% agarose gel, and DNA fragments of approximately 1.7-kb were detected for each of pdc genes of *Gluconobacter oxydans, Zymomonas mobilis, Zymobacter palmae*, and *Acetobacter* pasteurianus.

The approximately 1.7-kb DNA fragment of *Gluconobacter oxydans*-derived pdc gene that was amplified by the above-described PCR, and the above-mentioned approximately 10.6-kb DNA fragment of cloning vector pCYK21, were each cleaved by using restriction enzymes NdeI and BamHI. The cleaved DNA fragments were linked to each other using a T4 DNA Ligase (manufactured by Takara Bio Inc.).

The approximately 1.7-kb DNA fragments containing each of *Zymomonas mobilis, Zymobacter palmae*, and *Acetobacter* pasteurianus pdc genes, that were amplified by the above-described PCR were each cleaved by using restriction enzymes NdeI and SalI. The above-mentioned approximately 10.6-kb DNA fragment of cloning vector pCYK21 was also cleaved by using restriction enzymes NdeI and SalI. Each of the cleaved 1.7-kb DNA fragments and the 10.6-kb DNA fragment were linked to each other using a T4 DNA Ligase (manufactured by Takara Bio Inc.).

The obtained ligation solutions were used to transform *Hydrogenophilus thermoluteolus* strain TH-1 (NBRC 14978) by electric pulse method, and the transformants were applied onto A-solid medium containing kanamycin at 50 μg/ml, and incubated at 50° C. for 60 hours in a chamber that was filled with a mixed gas of $H_2:O_2:CO_2=7.5:1:1.5$.

Each of the viable strains on the A-solid medium was inoculated using a platinum loop into a test tube containing 5 ml of A-liquid medium containing kanamycin at 50 μg/ml. The test tubes were filled with a mixed gas of $H_2:O_2:CO_2=7.5:1:1.5$, and subjected to shaking culture at 50° C., and plasmid DNAs were extracted from the culture medium.

The plasmid containing *Gluconobacter oxydans*-derived pdc gene was cleaved using restriction enzymes NdeI and BamHI, and the inserted fragment was confirmed. As a result, an inserted fragment of *Gluconobacter oxydans*-derived pdc gene that was approximately 1.7-kb in length was observed in addition to an approximately 10.6-kb DNA fragment of plasmid pCYK21.

The plasmids containing each of *Zymomonas mobilis*, *Zymobacter palmae*, and *Acetobacter* pasteurianus pdc genes, were cleaved using restriction enzymes NdeI and SalI, and the inserted fragments were confirmed. As a result, inserted fragments of each of *Zymomonas mobilis*, *Zymobacter palmae*, and *Acetobacter* pasteurianus pdc genes, that were approximately 1.7-kb in length, were observed in addition to an approximately 10.6-kb DNA fragment of plasmid pCYK21.

The plasmid containing *Gluconobacter oxydans*-derived pdc gene was named pC-Gox-pdc, the plasmid containing *Zymomonas mobilis* pdc gene was named pC-Zmo-pdc, the plasmid containing *Zymobacter palmae* pdc gene was named pC-Zpa-pdc, and the plasmid containing *Acetobacter* pasteurianus pdc gene was named pC-Apa-pdc.

(4-2) Cloning of Alcohol Dehydrogenase Gene

The specifics are as described in item (3-3) of "(3) Transformant having isobutanol producing ability".

(4-3) Cloning of Aldehyde-Alcohol Dehydrogenase Gene

Genomic DNA was extracted from *Escherichia coli* K12 MG1655 according to a conventional method. In addition, genomic DNA of *Clostridium thermocellum* ATCC 27405 was obtained from National Institute of Technology and Evaluation (NBRC).

These genomic DNAs were each used as templates and DNA fragments containing aldehyde-alcohol dehydrogenase gene adhE were amplified by PCR method. The following primers were used for PCR. PCR was performed according to a conventional method using "DNA thermal cycler" manufactured by Life Technologies Inc., and using KOD FX Neo (manufactured by Toyobo Co., Ltd.) as a reaction reagent.

Primers for the amplification of *Escherichia coli* adhE gene (a-20)
(SEQ ID NO: 80)
5'-GCA<u>CATATG</u>GCTGTTACTAATGTCGCTGAACTTAA-3'

(b-20)
(SEQ ID NO: 81)
5'-GCA<u>GGATCC</u>TTAAGCGGATTTTTTCGCTTTTTTCT-3'

An NdeI restriction site has been added to primer (a-20), and a BamHI restriction site has been added to primer (b-20).

Primers for the amplification of *Clostridium thermocellum* adhE gene (a-21)
(SEQ ID NO: 82)
5'-GCA<u>CATATG</u>ACGAAAATAGCGAATAAATACGAAGT-3'

(b-21)
(SEQ ID NO: 83)
5'-GCA<u>CTGCAG</u>TTATTTCTTCGCACCTCCGTAATAAG-3'

An NdeI restriction site has been added to primer (a-21), and a PstI restriction site has been added to primer (b-21).

Two μl of the produced reaction solutions were subjected to electrophoresis using a 1% agarose gel, and DNA fragments of approximately 2.7-kb were detected for each of adhE gene derived from *Escherichia coli* and adhE gene derived from *Clostridium thermocellum*.

The approximately 2.7-kb DNA fragment of *Escherichia coli*-derived adhE gene, that was amplified by the above-described PCR, and the above-mentioned approximately 10.6-kb DNA fragment of cloning vector pCYK21, were each cleaved by using restriction enzymes NdeI and BamHI. The cleaved DNA fragments were linked to each other using a T4 DNA Ligase (manufactured by Takara Bio Inc.).

The approximately 2.7-kb DNA fragment of *Clostridium thermocellum*-derived adhE gene, that was amplified by the above-described PCR, and the above-mentioned approximately 10.6-kb DNA fragment of cloning vector pCYK21, were each cleaved by using restriction enzymes NdeI and PstI. The cleaved DNA fragments were linked to each other using a T4 DNA Ligase (manufactured by Takara Bio Inc.).

The obtained ligation solutions were used to transform *Hydrogenophilus thermoluteolus* TH-1 (NBRC 14978) by electric pulse method, and the transformants were applied onto A-solid medium containing kanamycin at 50 μg/ml, and incubated at 50° C. for 60 hours in a chamber that was filled with a mixed gas of $H_2:O_2:CO_2=7.5:1:1.5$.

Each of the viable strains on the A-solid medium was inoculated using a platinum loop into a test tube containing 5 ml of A-liquid medium containing kanamycin at 50 μg/ml. The test tubes were filled with a mixed gas of $H_2:O_2:CO_2=7.5:1:1.5$, and subjected to shaking culture at 50° C., and plasmid DNAs were extracted from the culture solution. Each of the plasmids was cleaved using restriction enzymes NdeI and BamHI, or NdeI and PstI, and the inserted fragments were confirmed. As a result, inserted fragment of approximately 2.7-kb in length of *Escherichia coli*-derived adhE gene or *Clostridium thermocellum*-derived adhE gene was observed in addition to an approximately 10.6-kb DNA fragment of plasmid pCYK21.

The plasmid containing *Escherichia coli*-derived adhE gene was named pC-Eco-adhE, and the plasmid containing *Clostridium thermocellum*-derived adhE gene was named pC-Cth-adhE.

The plasmids that were introduced into each transformant are shown in Table 3.

TABLE 3

| Plasmids possessed by each *Hydrogenophilus thermoluteolus* recombinant strain | | |
|---|---|---|
| Strain | Plasmid | Transgene |
| PDC01 | pC-Gox-pdc | pdc (*Gluconobacter oxydans*) |
| PDC02 | pC-Zmo-pdc | pdc (*Zymomonas mobilis*) |

TABLE 3-continued

Plasmids possessed by each *Hydrogenophilus thermoluteolus* recombinant strain

| Strain | Plasmid | Transgene |
|---|---|---|
| PDC03 | pC-Zpa-pdc | pdc (*Zymobacter palmae*) |
| PDC04 | pC-Apa-pdc | pdc (*Acetobacter pasteurianus*) |
| ADH01 | pC-Kpn-adhP | adhP (*Klebsiella pneumoniae*) |
| ADH02 | pC-Gtc-adhP | adhP (*Geobacillus thermocatenulatus*) |
| ADH03 | pC-Gtg-adhP | adhP (*Geobacillus thermoglucosidasius*) |
| ADH04 | pC-Gtg-adhA | adhA (*Geobacillus thermoglucosidasius*) |
| ADH05 | pC-Eco-adhE | adhE (*Escherichia coli*) |
| ADH06 | pC-Cth-adhE | adhE (*Clostridium thermocellum*) |

(4-4) Confirmation of Transgene Expression in *Hydrogenophilus thermoluteolus* Strains into which Ethanol Producing Gene has been Introduced Measurement of Pyruvate Decarboxylase Activity Strains PDC01, PDC02, PDC03, and PDC04 into which pyruvate decarboxylase genes (pdc genes) were introduced were inoculated using a platinum loop into test tubes containing 5 ml of A-liquid medium containing kanamycin at 50 μg/ml. The test tubes were filled with a mixed gas of $H_2:O_2:CO_2=7.5:1:1.5$, and subjected to shaking culture at 50° C. for 20 hours.

Bacterial cells that were proliferated by culturing were collected by centrifugation (4° C., 15,000 rpm, 1 minute). The bacterial cells were disrupted by sonication, and subsequently centrifuged (4° C., 15,000 rpm, 5 minutes) to obtain a cell disruption supernatant. The cell disruption supernatant was used as a crude enzyme solution to measure pyruvate decarboxylase activity by the following method. Crude enzyme solution, 250 mM sodium phosphate (pH 6.2), 1 mM $MgCl_2$, 1 mM thiamine pyrophosphate (TPP), 0.4 mM NADH, 100 mM pyruvic acid, and 0.02 mg/ml yeast alcohol dehydrogenase (Sigma-Aldrich Japan G.K.) were mixed, reacted at 50° C., and the decrease in absorbance at 340 nm coming from NADH was traced, and the initial rate of reaction was analyzed. Specific activity was calculated from the initial rate of reaction and protein concentration. The enzyme level for producing 1 μmol of acetaldehyde per minute was defined as 1 U (Unit).

As a result, 3.0 U/mg of intended pyruvate decarboxylase activity was detected in strain PDC01 into which *Gluconobacter oxydans* pdc gene was introduced.

On the other hand, no pyruvate decarboxylase activity was detected in strain PDC02 into which *Zymomonas mobilis* pdc gene was introduced, strain PDC03 into which *Zymobacter palmae* pdc gene was introduced, and strain PDC04 into which *Acetobacter pasteurianus* pdc gene was introduced.

In addition, no pyruvate decarboxylase activity was observed as a result of conducting the same experiment with regard to a wild-type strain of *Hydrogenophilus thermoluteolus* (strain TH-1 possessing only an empty vector (pCYK21)).

Measurement of Activity of Alcohol Dehydrogenase that Uses Acetaldehyde as a Substrate Each of *Hydrogenophilus thermoluteolus* strains ADH01, ADH02, ADH03, and ADH04, into which an alcohol dehydrogenase gene was introduced, was inoculated using a platinum loop into a test tube containing 5 ml of A-liquid medium containing kanamycin at 50 μg/ml. The test tubes were filled with a mixed gas of $H_2:O_2:CO_2=7.5:1:1.5$, and subjected to shaking culture at 50° C. for 20 hours.

Bacterial cells that were proliferated by culturing were each collected by centrifugation (4° C., 15,000 rpm, 1 minute). The bacterial cells were disrupted by sonication, and subsequently centrifuged (4° C., 15,000 rpm, 5 minutes) to obtain a cell disruption supernatant. The cell disruption supernatant was used as a crude enzyme solution to measure the activity of alcohol dehydrogenase that uses acetaldehyde as a substrate by the following method. Crude enzyme solution, 50 mM Tris-HCl (pH 8.0), 0.2 mM NADH, and 90 mM acetaldehyde were mixed, reacted at 50° C., and decrease in absorbance at 340 nm coming from NADH was traced, and the initial rate of reaction was analyzed. Specific activity was calculated from the initial rate of reaction and protein concentration. The enzyme level for producing 1 μmol of ethanol per minute was defined as 1 U (Unit).

As a result, intended alcohol dehydrogenase activity was detected in strains ADH01 to ADH04 as shown in Table 4. *Klebsiella pneumoniae*-derived adhP gene and *Geobacillus thermoglucosidasius*-derived adhP gene showed a particularly high activity. Alcohol dehydrogenase activity was also detected with regard to *Geobacillus thermocatenulatus*-derived adhP gene and *Geobacillus thermoglucosidasius*-derived adhA gene. No alcohol dehydrogenase activity was observed as a result of conducting the same experiment with regard to *Hydrogenophilus thermoluteolus* strain TH-1 into which an empty vector (pCYK21) was introduced.

The values of the activity of alcohol dehydrogenases that use acetaldehyde as a substrate, in *Hydrogenophilus thermoluteolus* strains into which adhP gene or adhA gene has been introduced are shown in Table

TABLE 4

| Strain | Plasmid | Transgene | Alcohol dehydrogenase activity (U/mg-protein) |
|---|---|---|---|
| ADH01 | pC-Kpn-adhP | adhP (*Klebsiella pneumoniae*) | 8.3 |
| ADH02 | pC-Gtc-adhP | adhP (*Geobacillus thermocatenulatus*) | 6.5 |
| ADH03 | pC-Gtg-adhP | adhP (*Geobacillus thermoglucosidasius*) | 7.8 |
| ADH04 | pC-Gtg-adhA | adhA (*Geobacillus thermoglucosidasius*) | 4.3 |
| pCYK21/ TH-1 | pCYK21 | none | ND (undetectable) |

(4-5) Site-Directed Mutagenesis into adhE Gene

Construction of Plasmid for Site-Directed Mutagenesis

The activity of the aldehyde-alcohol dehydrogenase encoded by adhE is inhibited under aerobic conditions. The above-described plasmid pC-Eco-adhE was used to prepare, by inverse PCR, a mutant of *Escherichia coli*-derived adhE (adhE(E568K)) in which the glutamic acid portion at position 568 (E568) was substituted by lysine (K), so that a high aldehyde-alcohol dehydrogenase activity would be shown even under aerobic conditions. The plasmid thus obtained by site-directed mutagenesis was named pC-Eco-E568K.

With regard to *Clostridium thermocellum*-derived adhE, the above-described plasmid pC-Cth-adhE was used to prepare, by inverse PCR, a mutant of *Clostridium thermocellum*-derived adhE (adhE(D575N)) in which the aspartic acid portion at position 575 (D575) was substituted by asparagine (N). The plasmid thus obtained by site-directed mutagenesis was named pC-Cth-D575N.

Inverse PCR was performed according to a conventional method using the primers described below and pC-Eco-adhE and pC-Cth-adhE as respective templates, using "DNA thermal cycler" manufactured by Life Technologies Inc., and using KOD FX Neo (manufactured by Toyobo Co., Ltd.) as a reaction reagent.
Primers for introducing E568K mutation of *Escherichia coli* adhE gene

```
(a-22)
                                       (SEQ ID NO: 84)
5'-GAAGCTGGCGCTGCGCTTTATGGATATCCGTAAAC-3'

(b-22)
                                       (SEQ ID NO: 85)
5'-TCGAAGTGAGTTTCCGGATGTTCGTACATAACCCA-3'
```

Primers for introducing D575N mutation of *Clostridium thermocellum* adhE gene

```
(a-23)
                                       (SEQ ID NO: 86)
5'-ATGGCAATGAGATTTATGGATATAAGAAAGAGAGT-3'

(b-23)
                                       (SEQ ID NO: 87)
5'-GTTCATAAAGTCAACTTCCGGATGTTCATACATCA-3'
```

The produced reaction solutions were subjected to electrophoresis using a 1% agarose gel, and DNA fragments of approximately 13-kb were detected for each of E568K mutant of *Escherichia coli*-derived adhE, and D575N mutant of *Clostridium thermocellum*-derived adhE.

Each of the amplified DNA fragments was phosphorylated using a T4 Polynucleotide Kinase (manufactured by Takara Bio Inc.) and then linked (by self-ligation) using a T4 DNA Ligase (manufactured by Takara Bio Inc.).

The obtained ligation solutions were used to transform *Hydrogenophilus thermoluteolus* NBRC 14978 by electric pulse method, and the obtained transformants were applied onto A-solid medium containing kanamycin at 50 μg/ml, and incubated at 50° C. for 60 hours in a chamber that was filled with a mixed gas of $H_2:O_2:CO_2=7.5:1:1.5$.

Each of the viable strains on the A-solid medium was inoculated using a platinum loop into a test tube containing 5 ml of A-liquid medium containing kanamycin at 50 μg/ml. The test tubes were filled with a mixed gas of $H_2:O_2:CO_2=7.5:1:1.5$, and subjected to shaking culture at 50° C., and plasmid DNAs were extracted from the culture medium. These plasmids were cleaved by restriction enzymes NdeI and BamHI in the case of E568K mutant gene of *Escherichia coli*-derived adhE, and cleaved by restriction enzymes NdeI and PstI in the case of D575N mutant gene of *Clostridium thermocellum*-derived adhE, respectively, and the inserted fragments were confirmed. As a result, inserted fragments of approximately 2.7-kb in length were observed for each mutant in addition to approximately 10.6-kb DNA fragments of plasmid pCYK21.

The plasmids possessed by *Hydrogenophilus thermoluteolus* recombinant strains into which mutant adhE gene was introduced are shown in Table 5.

TABLE 5

| Strain | Plasmid | Transgene |
|---|---|---|
| ADH07 | pC-Eco-E568K | adhE (E568K mutation) (*Escherichia coli*) |
| ADH08 | pC-Cth-D575N | adhE (D575N mutation) (*Clostridium thermocellum*) |

(4-6) Measurement of Activity of Aldehyde-Alcohol Dehydrogenase that Uses Acetaldehyde as a Substrate Transgenic strains of *Hydrogenophilus thermoluteolus* into which aldehyde-alcohol dehydrogenase genes were introduced (ADH05, ADH06) that were produced in item (4-3), and transgenic strains of *Hydrogenophilus* thermoluteolus into which mutant aldehyde-alcohol dehydrogenase genes were introduced (ADH07, ADH08) that were produced in item (4-5), were inoculated using a platinum loop into test tubes containing 5 ml of A-liquid medium containing kanamycin at 50 μg/ml. The test tubes were filled with a mixed gas of $H_2:O_2:CO_2=7.5:1:1.5$, and subjected to shaking culture at 50° C. for 20 hours.

Bacterial cells that were proliferated by culturing were collected by centrifugation (4° C., 15,000 rpm, 1 minute). The bacterial cells were disrupted by sonication, and subsequently centrifuged (4° C., 15,000 rpm, 5 minutes) to obtain a cell disruption supernatant. The cell disruption supernatant was used as a crude enzyme solution to measure the activity of alcohol dehydrogenase that uses acetaldehyde as a substrate, by the following method. Crude enzyme solution, 50 mM Tris-HCl (pH 8.0), 0.2 mM NADH, and 90 mM acetaldehyde were mixed, reacted at 50° C., and decrease in absorbance at 340 nm coming from NADH was traced, and the initial rate of reaction was analyzed. Specific activity was calculated from the initial rate of reaction and protein concentration. The enzyme level for producing 1 μmol of ethanol per minute was defined as 1 U (Unit).

As mentioned above, aldehyde-alcohol dehydrogenase encoded by adhE gene is a bifunctional enzyme that has both an aldehyde dehydrogenase activity which catalyzes the reaction of converting acetyl-CoA into acetaldehyde, and an alcohol dehydrogenase activity which catalyzes the reaction of converting acetaldehyde into ethanol. Here, the expression of adhE gene was evaluated using as an index, the reaction of producing ethanol in which acetaldehyde is used as a substrate. However, each of the above-described strains also had an aldehyde dehydrogenase activity which catalyzes the reaction of converting acetyl-CoA into acetaldehyde.

As a result, strains ADH07 and ADH08 into which mutated genes were introduced had 1.5-fold and 3.4-fold improved activity as compared to those of strains ADH05 and ADH06 into which wild-type genes were introduced, respectively, as shown in Table 6.

TABLE 6

| Strain | Plasmid | Transgene | Alcohol dehydrogenase activity (U/mg-protein) |
|---|---|---|---|
| ADH05 | pC-Eco-adhE | adhE (*Escherichia coli*) | 0.34 |
| ADH06 | pC-Cth-adhE | adhE (*Clostridium thermocellum*) | 0.26 |
| ADH07 | pC-Eco-E568K | adhE (E568K mutation) (*Escherichia coli*) | 0.52 |
| ADH08 | pC-Cth-D575N | adhE (D575N mutation) (*Clostridium thermocellum*) | 0.89 |
| pCYK21/ TH-1 | pCYK21 | None | ND (undetectable) |

(4-7) Production of Ethanol Producing Strain

The DNA fragment which contains adhP gene encoding the alcohol dehydrogenase of *Klebsiella pneumoniae* was amplified according to a conventional method using PCR, in which "DNA thermal cycler" manufactured by Life Technologies Inc. was used and KOD FX Neo (manufactured by Toyobo Co., Ltd.) was used as a reaction reagent. Plasmid pC-Kpn-adhP was used as a template DNA, and the following primer pair was used.
Primers for the Amplification of *Klebsiella pneumoniae* adhP Gene (a-24)
(SEQ ID NO: 88)
5'-CGC<u>GGTACC</u>GGATCTGGAGGAGAAACGCATATGAA-3'

(b-24)
(SEQ ID NO: 89)
5'-CGC<u>GGTACC</u>TTAACGGTTGACACCGATGGTTAAAA-3'

A KpnI restriction site has been added to primers (a-24) and (b-24).

The produced reaction solution was subjected to electrophoresis using a 1% agarose gel, and as a result, a DNA fragment of approximately 1.0-kb was detected which corresponds to *Klebsiella pneumoniae* derived adhP gene.

The approximately 1.0-kb DNA fragment of *Klebsiella pneumoniae* adhP gene that was amplified by the above-mentioned PCR, and the approximately 12.3-kb DNA fragment of plasmid pC-Gox-pdc that contains *Gluconobacter oxydans* pdc gene, were each cleaved by restriction enzyme KpnI. The cleaved DNA fragments were linked to each other using a T4 DNA Ligase (manufactured by Takara Bio Inc.).

The obtained ligation solution was used to transform *Hydrogenophilus thermoluteolus* NBRC 14978 by electric pulse method, and the obtained transformant was applied onto A-solid medium containing kanamycin at 50 μg/ml, and incubated at 50° C. for 60 hours in a chamber that was filled with a mixed gas of $H_2:O_2:CO_2=7.5:1:1.5$.

Viable strains on the A-solid medium were inoculated using a platinum loop into a test tube containing 5 ml of A-liquid medium containing kanamycin at 50 μg/ml. The test tube was filled with a mixed gas of $H_2:O_2:CO_2=7.5:1:1.5$, and subjected to shaking culture at 50° C., and plasmid DNA was extracted from the culture medium. The plasmid was cleaved by restriction enzyme KpnI, and the inserted fragment was confirmed. As a result, an approximately 1.0-kb inserted fragment of *Klebsiella pneumoniae* adhP gene was observed in addition to an approximately 12.3-kb DNA fragment of plasmid pC-Gox-pdc.

The plasmid containing *Klebsiella pneumoniae* adhP gene downstream of *Gluconobacter oxydans* pdc gene, was named pC-Gox-pdc&Kpn-adhP.

The strain possessing this plasmid was named *Hydrogenophilus thermoluteolus* strain ETH-1.

(4-8) Production of Ethanol

*Hydrogenophilus thermoluteolus* strain (strain ETH-1) into which an ethanol producing gene was introduced, which was obtained in the above item (4-7), was inoculated using a platinum loop into A-liquid medium containing kanamycin at 50 μg/ml, and subjected to shaking culture at 50° C. for 30 hours while supplying a mixed gas of $H_2:O_2:CO_2=7.5:1:1.5$ accompanying incubation.

Following incubation, the culture supernatant was obtained by centrifugation (4° C., 15,000 rpm, 1 minute), and as a result of quantification of the ethanol therein, production of 10 mM of ethanol was confirmed in the culture supernatant.

(5) Production of Transformant Having Alanine Producing Ability (5-1) Preparation of Genomic DNA Genomic DNA was extracted from *Geobacillus stearothermophilus* ATCC 12980 according to a conventional method. In addition, genomic DNA of *Thermus thermophilus* strain HB8 (ATCC 27634) was purchased from Takara Bio Inc.

(5-2) Cloning of DNA Fragment Containing alaD Gene

DNA fragments containing alanine dehydrogenase genes were amplified by PCR using each of the genomic DNA of *Geobacillus stearothermophilus* ATCC 12980 and the genomic DNA of *Thermus thermophilus* strain HB8 (ATCC 27634) as templates, and using the following primer pairs. PCR was performed according to a conventional method using "DNA thermal cycler" manufactured by Life Technologies Inc., and using KOD FX Neo (manufactured by Toyobo Co., Ltd.) as a reaction reagent.

Primers for the amplification of *Geobacillus stearothermophilus* alaD1 gene (a-25)
(SEQ ID NO: 90)
5'-TCCGGCGGG<u>CATATG</u>AAGATCGGCATTCCAAAAGA-3'

(b-25)
SEQ ID NO: 91)
5'-AA<u>GAATTC</u>CAGCGGCTCATATACGATACCGTTCGG-3'

An NdeI restriction site has been added to primer (a-25), and an EcoRI restriction site has been added to primer (b-25).
Primers for the amplification of *Geobacillus stearothermophilus* alaD2 gene (a-26)
(SEQ ID NO: 92)
5'-TCCGGCGGG<u>CATATG</u>ATTATTGGAGTGCCAAAGGA-3'

(b-26)
(SEQ ID NO: 93)
5'-AA<u>GAATTC</u>TTAGTTGGCAGCCAACGTTTTCCCGAG-3'

An NdeI restriction site has been added to primer (a-26), and an EcoRI restriction site has been added to primer (b-26).
Primers for the amplification of *Thermus thermophilus* alaD1 gene (a-27)
(SEQ ID NO: 94)
5'-CCGGCGGG<u>CATATG</u>GTGATCGGCGTGCCGAAGGAG-3'

(b-27)
(SEQ ID NO: 95)
5'-AA<u>GAATTC</u>TCACCCCCTCAAGGCCTCCTCGGGAGG-3'

An NdeI restriction site has been added to primer (a-27), and an EcoRI restriction site has been added to primer (b-27).
Primers for the amplification of *Thermus thermophilus* alaD2 gene (a-28)
(SEQ ID NO: 96)
5'-CGGCGGG<u>CATATG</u>gagttcggcgtgcccagagaac-3'

(b-28)
(SEQ ID NO: 97)
5'-AA<u>GAATTC</u>tcattctaggtggcctcctttctcgcc-3'

An NdeI restriction site has been added to primer (a-28), and an EcoRI restriction site has been added to primer (b-28).

The produced reaction solutions were subjected to electrophoresis using a 1% agarose gel, and a DNA fragment of approximately 1.6-kb was detected in the case of *Geobacillus stearothermophilus* alaD1 gene, and DNA fragments of approximately 1.1-kb were detected in each of the cases of Geobacillus stearothermophilus alaD2 gene, Thermus thermophilus alaD1 gene, and Thermus thermophilus alaD2 gene.

Each of the approximately 1.6-kb DNA fragment of Geobacillus stearothermophilus alaD1 gene, the approximately 1.1-kb DNA fragment of Geobacillus stearothermophilus alaD2 gene, the approximately 1.1-kb DNA fragment of Thermus thermophilus alaD1 gene, and the approximately 1.1-kb DNA fragment of Thermus thermophilus alaD2 gene, which was amplified by the above-described PCR, were cleaved by restriction enzymes NdeI and EcoRI. The approximately 10.6-kb DNA fragment of the above-described cloning vector pCYK21 was also cleaved by restriction enzymes NdeI and EcoRI. Each of the cleaved 1.6-kb or 1.1-kb DNA fragments and the 10.6-kb DNA fragment were linked to each other using a T4 DNA Ligase (manufactured by Takara Bio Inc.).

The obtained ligation solutions were used to transform Hydrogenophilus thermoluteolus NBRC 14978 by electric pulse method, and the obtained transformants were applied onto A-solid medium containing kanamycin at 50 μg/ml, and incubated at 50° C. for 60 hours in a chamber that was filled with a mixed gas of $H_2:O_2:CO_2=7.5:1:1.5$.

Each of the viable strains on the A-solid medium was inoculated using a platinum loop into a test tube containing 5 ml of A-liquid medium containing kanamycin at 50 μg/ml. The test tubes were filled with a mixed gas of $H_2:O_2:CO_2=7.5:1:1.5$, and subjected to shaking culture at 50° C., and plasmid DNAs were extracted from the culture solutions. These plasmids were each cleaved by restriction enzymes NdeI and EcoRI, and the inserted fragments were confirmed. As a result, an inserted fragment of approximately 1.6-kb in length in the case of Geobacillus stearothermophilus alaD1 gene, and inserted fragments of approximately 1.1-kb in length in each of the cases of Geobacillus stearothermophilus alaD2 gene, Thermus thermophilus alaD1 gene, and Thermus thermophilus alaD2 gene, were observed in addition to an approximately 10.6-kb DNA fragment of plasmid pCYK21.

The plasmid containing Geobacillus stearothermophilus alaD1 gene was named pC-Gst-alaD1, the plasmid containing Geobacillus stearothermophilus alaD2 gene was named pC-Gst-alaD2, the plasmid containing Thermus thermophilus alaD1 gene was named pC-Tth-alaD1, and the plasmid containing Thermus thermophilus alaD2 gene was named pC-Tth-alaD2. The plasmids that are possessed by these recombinant strains of Hydrogenophilus thermoluteolus are shown in Table 7.

TABLE 7

| Strain | Plasmid | Transgene |
|---|---|---|
| ALA01 | pC-Gst-alaD1 | alaD1 (Geobacillus stearothermophilus) |
| ALA02 | pC-Gst-alaD2 | alaD2 (Geobacillus stearothermophilus) |
| ALA03 | pC-Tth-alaD1 | alaD1 (Thermus thermophilus) |
| ALA04 | pC-Tth-alaD2 | alaD2 (Thermus thermophilus) |

(5-3) Measurement of Alanine Dehydrogenase Activity

Each of strains ALA01, ALA02, ALA03, and ALA04, which are Hydrogenophilus thermoluteolus strains into which alanine dehydrogenase gene has been introduced, was inoculated using a platinum loop into a test tube containing 5 ml of A-liquid medium containing kanamycin at 50 μg/ml. The test tubes were filled with a mixed gas of $H_2:O_2:CO_2=7.5:1:1.5$, and subjected to shaking culture at 50° C. for 20 hours.

Bacterial cells that were proliferated by culturing were each collected by centrifugation (4° C., 15,000 rpm, 1 minute). The bacterial cells were disrupted by sonication, and subsequently centrifuged (4° C., 15,000 rpm, 5 minutes) to obtain a cell disruption supernatant. The cell disruption supernatant was used as a crude enzyme solution to measure alanine dehydrogenase activity by the following method. Crude enzyme solution, 100 mM Tris-HCl (pH 8.5), 100 mM $NH_4Cl$, 0.1 mM NADH, and 60 mM pyruvic acid were mixed, reacted at 50° C., and decrease in absorbance at 340 nm coming from NADH was traced, and the initial rate of reaction was analyzed. Specific activity was calculated from the initial rate of reaction and protein concentration. The enzyme level for producing 1 μmol of alanine per minute was defined as 1 U (Unit).

The values of the activity of alanine dehydrogenases that were produced by the alaD gene-introduced strains of Hydrogenophilus thermoluteolus are shown in Table 8.

TABLE 8

| Strain | Plasmid | Transgene | Alanine dehydrogenase activity (U/mg-protein) |
|---|---|---|---|
| ALA01 | pC-Gst-alaD1 | alaD1 (Geobacillus stearothermophilus) | 15.5 |
| ALA02 | pC-Gst-alaD2 | alaD2 (Geobacillus stearothermophilus) | 35.1 |
| ALA03 | pC-Tth-alaD1 | alaD1 (Thermus thermophilus) | 3.7 |
| ALA04 | pC-Tth-alaD2 | alaD2 (Thermus thermophilus) | 0.5 |
| pCYK21/TH-1 | pCYK21 | None | ND (undetectable) |

As shown in Table 8, alanine dehydrogenase activity of interest was detected in strains ALA01, ALA02, ALA03, and ALA04. Geobacillus stearothermophilus-derived alaD2 gene showed a particularly high activity. On the other hand, no alanine dehydrogenase activity was observed as a result of conducting the same experiment with regard to Hydrogenophilus thermoluteolus strain TH-1 into which an empty vector (pCYK21) was introduced.

(5-4) Addition of Polypeptide to the N Terminus for the Improvement of Gene Expression Level Preparation of DNA Fragment Encoding Polypeptide to be Added Each of the following pairs of oligonucleotides was synthesized in order to prepare DNA fragments which encode polypeptides to be added. Sequences of each of the pair of oligonucleotides are complementary with one another.

Polypeptide of sequence MKIEEGKLVIH (SEQ ID NO: 37) (sequence of the N terminus of maltose-binding protein)

```
(a-29)
                                     (SEQ ID NO: 98)
5'-TATGAAAATCGAAGAAGGTAAACTGGTAATCCA-3'

(b-29)
                                     (SEQ ID NO: 99)
5'-TATGGATTACCAGTTTACCTTCTTCGATTTTCA-3'
```

Polypeptide of sequence MSKIKH (SEQ ID NO: 100) [Journal of Bioscience and Bioengineering, 123, 540-546 (2017)]

(a-30)
(SEQ ID NO: 101)
5'-TATGAGCAAGATCAAACA-3'

(b-30)
(SEQ ID NO: 102)
5'-TATGTTTGATCTTGCTCA-3'

Polypeptide of sequence MDFPVAEDRRH (SEQ ID NO: 103) (sequence of the N terminus of glutathione S-transferase)

(a-31)
(SEQ ID NO: 104)
5'-TATGTCGCCGATCCTCGGCTACTGGAAAATCCA-3'

(b-31)
(SEQ ID NO: 105)
5'-TATGGATTTTCCAGTAGCCGAGGATCGGCGACA-3'

Polypeptide of sequence MTENAEKFLWH (SEQ ID NO: 106) (sequence of the N terminus of β-glucosidase)

(a-32)
(SEQ ID NO: 107)
5'-TATGACCGAGAACGCCGAAAAATTCCTTTGGCA-3'

(b-32)
(SEQ ID NO: 108)
5'-TATGCCAAAGGAATTTTTCGGCGTTCTCGGTCA-3'

Equimolar (mol) amounts of each of the oligonucleotides (a-29) and (b-29), (a-30) and (b-30), (a-31) and (b-31), (a-32) and (b-32), were mixed, and the mixed solutions were gradually cooled from 98° C. to 20° C. As a result of annealing of the oligonucleotides, double-stranded DNA fragments encoding polypeptide sequences were prepared. Both ends of these DNA fragments are equivalent to the cohesive end generated from cleavage by restriction enzyme NdeI.

In addition, in order to prepare a DNA fragment which consists of a base sequence encoding the sequence of MGKDHLIHNVHKEEHAHAHNKH (SEQ ID NO: 109) (HAT sequence), PCR was performed using a primer pair described below, using "DNA thermal cycler" manufactured by Life Technologies Inc., and using KOD FX Neo (manufactured by Toyobo Co., Ltd.) as a reaction reagent. No template DNA was included since extension was carried out using each primer as the other's template.

Primers for preparing HAT sequence (a-33)
(SEQ ID NO: 110)
5'-CG<u>CATATG</u>GGCAAGGATCATCTCATCCACAATGTCCACAAAGAGG-3'

(b-33)
(SEQ ID NO: 111)
5'-CG<u>CATATG</u>CTTGTTGTGGGCATGAGCGTGCTCCTCTTTGTGGACA-3'

The base sequences of the 3' end of primers (a-33) and (b-33) are complementary to each other. An NdeI restriction site has been added to primers (a-33) and (b-33).

The produced reaction solution was subjected to electrophoresis using a 1% agarose gel, and as a result, a DNA fragment of approximately 0.1-kb which corresponds to the HAT sequence was detected. The approximately 0.1-kb DNA fragment of the HAT sequence that was amplified was cleaved by restriction enzyme NdeI.

Construction of Expression Vector for Polypeptide-Fused Protein

Plasmid pC-Gst-alaD2 which contains *Geobacillus stearothermophilus* alaD2 gene was cleaved by restriction enzyme NdeI. This plasmid and each of the above-described DNA fragments which have an overhang on both ends due to cleavage by restriction enzyme NdeI (the 5-kind double-stranded DNA fragments that were prepared in item "Preparation of DNA fragment encoding polypeptide to be added") were mixed, and were linked to each other using a T4 DNA Ligase (manufactured by Takara Bio Inc.).

The obtained ligation solutions were used to transform *Hydrogenophilus thermoluteolus* NBRC 14978 by electric pulse method, and the transformants were applied onto A-solid medium containing kanamycin at 50 μg/ml, and incubated at 50° C. for 60 hours in a chamber that was filled with a mixed gas of $H_2:O_2:CO_2=7.5:1:1.5$.

Each of the viable strains on the A-solid medium was inoculated using a platinum loop into a test tube containing 5 ml of A-liquid medium containing kanamycin at 50 μg/ml. The test tubes were filled with a mixed gas of $H_2:O_2:CO_2=7.5:1:1.5$, and subjected to shaking culture at 50° C. Plasmid DNAs were extracted from the culture solutions, and each of the plasmids were cleaved using restriction enzyme NdeI, and inserted fragments were confirmed.

The plasmid for adding the N terminus sequence of maltose-binding protein to generate a fusion peptide was named pMBP-Gst-alaD2, the plasmid for adding the sequence MSKIKH to generate a fusion peptide was named pSKIK-Gst-alaD2, the plasmid for adding the N terminus sequence of glutathione S-transferase to generate a fusion peptide was named pGST-Gst-alaD2, the plasmid for adding the N terminus sequence of β-glucosidase to generate a fusion peptide was named pGlu-Gst-alaD2, and the plasmid for adding the HAT tag sequence to generate a fusion peptide was named pHAT-Gst-alaD2.

The plasmids possessed by the recombinant strains are shown in Table 9.

TABLE 9

| Strain | Plasmid | N terminus-fused peptide |
|---|---|---|
| ALA02 | pC-Gst-alaD2 | None |
| ALA05 | pMBP-Gst-alaD2 | N terminus sequence of maltose-binding protein |
| ALA06 | pSKIK-Gst-alaD2 | Sequence MSKIKH |
| ALA07 | pGST-Gst-alaD2 | N terminus sequence of glutathione S-transferase |
| ALA08 | pGlu-Gst-alaD2 | N terminus sequence of β-glucosidase |
| ALA09 | pHAT-Gst-alaD2 | HAT tag sequence |

(5-5) Effect of Polypeptide Fusion at N Terminus Side on Expression of alaD2 Gene Transgenic strains of *Hydrogenophilus thermoluteolus* into which polypeptide-fused alanine dehydrogenase genes were introduced that were produced in item (5-4), were inoculated using a platinum loop into test tubes containing 5 ml of A-liquid medium containing kanamycin at 50 μg/ml. The test tubes were filled with a mixed gas of $H_2:O_2:CO_2=7.5:1:1.5$, and subjected to shaking culture at 50° C. for 20 hours.

Bacterial cells that were proliferated by culturing were each collected by centrifugation (4° C., 15,000 rpm, 1 minute). The bacterial cells were disrupted by sonication, and subsequently centrifuged (4° C., 15,000 rpm, 5 minutes) to obtain a cell disruption supernatant. The cell disruption supernatant was used as a crude enzyme solution to measure the alanine dehydrogenase activity by the following method. Crude enzyme solution, 100 mM Tris-HCl (pH 8.5), 100 mM $NH_4Cl$, 0.1 mM NADH, and 60 mM pyruvic acid were mixed, reacted at 50° C., and decrease in absorbance at 340 nm coming from NADH was traced, and the initial rate of reaction was analyzed. Specific activity was calculated from the initial rate of reaction and protein concentration. The enzyme level for producing 1 μmol of alanine per minute was defined as 1 U (Unit).

The activities of alanine dehydrogenases that were produced by alaD transgenic strains of *Hydrogenophilus thermoluteolus* are shown in Table 10.

TABLE 10

| Strain | Plasmid | N terminus-fused peptide | Alanine dehydrogenase activity (U/mg-protein) |
|---|---|---|---|
| ALA02 | pC-Gst-alaD2 | None | 35.1 |
| ALA05 | pMBP-Gst-alaD2 | N terminus sequence of maltose-binding protein | 144.6 |
| ALA06 | pSKIK-Gst-alaD2 | Sequence MSKIKH | 11.7 |
| ALA07 | pGST-Gst-alaD2 | N terminus sequence of glutathione S-transferase | 10.9 |
| ALA08 | pGlu-Gst-alaD2 | N terminus sequence of β-glucosidase | 2.7 |
| ALA09 | pHAT-Gst-alaD2 | HAT tag sequence | 31.2 |

As shown in Table 10, only strain ALA05 showed a higher alanine dehydrogenase activity as compared to that of the strain into which *Geobacillus stearothermophilus* alaD2 gene was introduced (strain ALA02).

(5-6) Production of Alanine

Transgenic strain ALA05 of *Hydrogenophilus thermoluteolus* into which an alanine dehydrogenase gene was introduced, was inoculated using a platinum loop into A-liquid medium containing kanamycin at 50 μg/ml, and subjected to shaking culture at 50° C. for 30 hours while supplying a mixed gas of $H_2:O_2:CO_2=7.5:1:1.5$ during incubation.

Following incubation, the culture supernatant was obtained by centrifugation (4° C., 15,000 rpm, 1 minute), and as a result of quantification of the alanine therein, production of 5 mM of alanine was confirmed in the culture supernatant.

(6) Deposited Strains

Each of the strains shown in the following Table 11 was deposited to NITE Patent Microorganisms Depositary, National Institute of Technology and Evaluation (2-5-8 Kazusakamatari, Kisarazu-shi, Chiba, Japan (postal code 292-0818)). The date of acceptance and the accession numbers are shown in Table 11. Accordingly, these strains are available to the public.

TABLE 11

| Deposited strain | Date of acceptance | Accession number |
|---|---|---|
| *Hydrogenophilus thermoluteolus* IBU-1 | Apr. 18, 2018 | NITE BP-02696 |
| *Hydrogenophilus thermoluteolus* ETH-1 | Apr. 18, 2018 | NITE BP-02697 |
| *Hydrogenophilus thermoluteolus* ADH05 | Apr. 18, 2018 | NITE P-02691 |
| *Hydrogenophilus thermoluteolus* ADH07 | Apr. 18, 2018 | NITE P-02692 |
| *Hydrogenophilus thermoluteolus* ADH08 | Apr. 18, 2018 | NITE P-02693 |
| *Hydrogenophilus thermoluteolus* ALA02 | Apr. 18, 2018 | NITE P-02694 |
| *Hydrogenophilus thermoluteolus* ALA05 | Apr. 18, 2018 | NITE BP-02695 |

Furthermore, all strains (including ATCC strains and NBRC strains) that are described in the present specification are internationally deposited under the Budapest Treaty, or are possessed by organizations that furnish the strains without any terms or conditions, or are marketed, and therefore, the strains are all available to the public.

INDUSTRIAL APPLICABILITY

The transformant of the present invention effectively produces isobutanol, ethanol, or alanine using carbon dioxide as a sole carbon source, and therefore, the two problems of global warming due to carbon dioxide increase and difficulty in securing food, feed, and fuel, can both be solved.

The invention claimed is:

1. A synthesized DNA encoding 2-keto-acid decarboxylase of (a1) or (a2):
   (a1) comprising a base sequence of SEQ ID NO: 1; or
   (a2) comprising a base sequence having 90% or more identity with SEQ ID NO: 1 and being configured to be expressed in bacteria of genus *Hydrogenophilus*.

2. A transformant obtained by introducing (a) the DNA according to claim 1, and (b) an alcohol dehydrogenase gene, into a bacterium of genus *Hydrogenophilus*.

3. The transformant according to claim 2, wherein the alcohol dehydrogenase gene (b) comprises a DNA of (b1), (b2), (b4), (b5), or (b6):
   (b1) a base sequence of SEQ ID NO: 2, 3, 4, or 5;
   (b2) a base sequence having 90% or more identity with SEQ ID NO: 2, 3, 4, or 5, the DNA encoding a polypeptide having alcohol dehydrogenase activity;
   (b4) DNA which encodes a polypeptide consisting of an amino acid sequence of SEQ ID NO: 6, 7, 8, or 9;
   (b5) DNA which encodes a polypeptide consisting of an amino acid sequence having 90% or more identity with SEQ ID NO: 6, 7, 8, or 9, the polypeptide having alcohol dehydrogenase activity; or
   (b6) DNA which encodes a polypeptide consisting of an amino acid sequence having a deletion, substitution, or addition of one or a plurality of amino acids in the amino acid sequence of SEQ ID NO: 6, 7, 8, or 9, the polypeptide having alcohol dehydrogenase activity.

4. The transformant according to claim 2, wherein the bacterium of the genus *Hydrogenophilus* is *Hydrogenophilus thermoluteolus*.

5. A method for producing isobutanol comprising culturing the transformant according to claim 2, while using carbon dioxide as a sole carbon source.

6. The transformant according to claim 3, wherein the alcohol dehydrogenase gene (b) comprises the DNA of (b1).

7. The transformant according to claim 3, wherein the alcohol dehydrogenase gene (b) comprises the DNA of (b2).

8. The synthesized DNA according to claim 1, wherein the synthesized DNA comprises a base sequence having 95% or more identity with SEQ ID NO: 1.

9. The synthesized DNA according to claim 1, wherein the synthesized DNA consists of the base sequence of SEQ ID NO: 1.

10. The transformant according to claim 2, wherein the alcohol dehydrogenase gene (b) comprises the DNA of (b4).

11. The transformant according to claim 3, wherein the alcohol dehydrogenase gene (b) comprises the DNA of (b5).

12. The transformant according to claim 3, wherein the alcohol dehydrogenase gene (b) comprises the DNA of (b6).

13. A synthesized DNA encoding 2-keto-acid decarboxylase comprising a base sequence of SEQ ID NO: 1.

14. A synthesized DNA for recombinant expression of 2-keto-acid decarboxylase in a bacterium of genus *Hydrogenophilus*, comprising a base sequence having 90% or more identity with SEQ ID NO: 1.

15. A vector comprising the synthesized DNA according to claim 14.

16. A transformant comprising the vector according to claim 15, wherein the transformant is a bacterium of genus *Hydrogenophilus*.

17. The transformant according to claim 16, further comprising a vector comprising an alcohol dehydrogenase gene.

18. A cell transformed with the synthesized DNA according to claim 14, wherein the cell is a bacterium of genus *Hydrogenophilus*.

19. A method of producing isobutanol comprising culturing the transformant according to claim 16.

* * * * *